US008383802B2

(12) United States Patent
Fung et al.

(10) Patent No.: US 8,383,802 B2
(45) Date of Patent: *Feb. 26, 2013

(54) NUCLEIC ACIDS ENCODING ANTIBODIES THAT BIND FACTOR D

(75) Inventors: Michael S. C. Fung, Gaithersburg, MD (US); William N. C. Sun, Shanghai (CN); Cecily R. Y. Sun, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/540,275

(22) Filed: Jul. 2, 2012

(65) Prior Publication Data

US 2012/0322975 A1 Dec. 20, 2012

Related U.S. Application Data

(60) Continuation of application No. 13/351,845, filed on Jan. 17, 2012, now Pat. No. 8,236,317, which is a continuation of application No. 13/081,203, filed on Apr. 6, 2011, now Pat. No. 8,124,090, which is a continuation of application No. 11/478,088, filed on (Continued)

(51) Int. Cl.
*C12N 15/13* (2006.01)
*C12N 15/00* (2006.01)
*C12N 5/10* (2006.01)

(52) U.S. Cl. .................. 536/23.53; 536/23.5; 435/69.6; 435/252.3; 435/320.1; 435/326; 435/337

(58) Field of Classification Search .......................... None
See application file for complete search history.

(56) References Cited

U.S. PATENT DOCUMENTS

| 5,456,909 | A  | 10/1995 | Marsh et al. |
| 5,624,837 | A  | 4/1997 | Fordor et al. |
| 5,627,264 | A  | 5/1997 | Fodor et al. |
| 5,679,564 | A  | 10/1997 | Pace et al. |
| 5,851,528 | A  | 12/1998 | Ko et al. |
| 5,853,722 | A  | 12/1998 | Rollins et al. |
| 5,856,297 | A  | 1/1999 | Fearon et al. |
| 5,856,300 | A  | 1/1999 | Rittershaus et al. |
| 5,858,969 | A  | 1/1999 | Marsh et al. |
| 5,861,156 | A  | 1/1999 | George et al. |
| 6,956,107 | B2 | 10/2005 | Fung et al. |
| 7,112,327 | B2 | 9/2006 | Fung et al. |
| 7,439,331 | B2 | 10/2008 | Fung et al. |
| 7,943,135 | B2 | 5/2011 | Fung et al. |
| 8,124,090 | B2 | 2/2012 | Fung et al. |
| 8,236,317 | B2 | 8/2012 | Fung et al. |

FOREIGN PATENT DOCUMENTS

| WO | WO 95/29697 | 11/1995 |
| WO | WO 99/42133 | 8/1999 |

OTHER PUBLICATIONS

Amersterdam et al., 1995, "Limitation of reperfusion injury by a monoclonal antibody to C5a during myocardial infarction in pigs." Am. J. Physiol. 268(1 Pt 2): H448-57.

Bertozzi et al., 1997, "An ELISA for selectins based on binding to a physiological ligand." J. Immunol. Methods 203(2):157-65.

Brown et al., 2007, "Mechanisms of disease: the complement system in renal injury—new ways of looking at an old foe." Nat Clin Pract Nephrol. 3(5):277-86.

Evans et al., "Rapid Expression of an Anti-Human C5 Chimeric Fab Utilizing a Vector that Replicates in COS and 293 Cells," J. Immunol., 184: 123-138 (1995).

Fung, M. et al., 2000, "Inhibition of Complement, Neutrophil, and Platelet Activation by an Anti-Factor D Antibody During Extracorporeal Circulation". Presented in the 18th Annual Houston Conference on Biomedical Engineering Research, Houston, Texas. Feb. 10-11, 2000 (Abstract).

Gao et al., 1995, "An enzyme-linked immunosorbent assay to identify inhibitors of activation of platelet integrin alpha IIb beta 3" J. Immunol. Methods. 181(1):55-64.

Holers, 1996, "Principles and Practices." Clinical Immunol. R.R. Rich Rich Edition, Mosby Press pp. 363-391.

Homeister et al., 1993, "Soluble complement receptor type 1 prevents human complement-mediated damage of the rabbit isolated heart" J. Immunol. 150(3):1055-64.

Houghten et al., 1992, "The use of synthetic peptide combinatorial libraries for the identification of bioactive peptides." Biotechniques 13(3):412-21.

Huber-Lang et al., "Role of C5a in Multiorgan Failure During Sepsis" J. of Immunology, 166:1193-1198 (2001).

Inagi et al., 1993, "Decreased Activity of Complement-Mediated Immune Complex Clearance in Hemodialysis Patients," Clin. Immune & Immunopath. 68(3):333-339.

Janeway et al., 1997,*Immunobiology* (13-5 to 13-7) 3rd edition, London, Eng Current Biology ltd.

Klohs et al., 1997, "Inhibitors of tyrosine kinase." Curr. Opin. Oncol. 19 9(6):562-8.

Kostavasilli et al., 1997, "Mechanism of complement inactivation by glycoprotein c of herpes simplex virus." Immunol. 158(4): 1763-71.

Kroshus et al., 1995, "Complement inhibition owith an anti-05 monoclonal antibody prevents acute cardiac tissue injry in an ex vivo model of pig-to-human xenotransplatation." Transplantation 60(11):1194-202.

(Continued)

*Primary Examiner* — Phillip Gambel
(74) *Attorney, Agent, or Firm* — Jones Day

(57) ABSTRACT

The invention relates to factor D inhibitors, which bind to factor D and block the functional activity of factor D in complement activation. The inhibitors include antibody molecules, as well as homologues, analogues and modified or derived forms thereof, including immunoglobulin fragments like Fab, F(ab')$_2$ and Fv, small molecules, including peptides, oligonucleotides, peptidomimetics and organic compounds. A monoclonal antibody which bound to factor D and blocked its ability to activate complement was generated and designated 166-32. The hybridoma producing this antibody was deposited at the American Type Culture Collection, 10801 University Blvd., Manassas, Va. 20110-2209, under Accession Number HB-12476.

8 Claims, 52 Drawing Sheets

Related U.S. Application Data

Jun. 29, 2006, now Pat. No. 7,943,135, which is a division of application No. 11/139,447, filed on May 27, 2005, now Pat. No. 7,112,327, which is a division of application No. 09/821,255, filed on Mar. 29, 2001, now Pat. No. 6,956,107, which is a continuation-in-part of application No. 09/253,689, filed on Feb. 20, 1999, now abandoned.

(60) Provisional application No. 60/075,328, filed on Feb. 20, 1998.

(56) References Cited

OTHER PUBLICATIONS

Lam et al., 1997, "Application of combinatorial library methods in cancer research and drug discovery." Anticancer Drug Des 12(3): 145-67.
Laubser et al., "Inhibition of Complement, Neutrophil, and Platelet Activation by an Anti-Factor D Antibody During Extracorporeal Circulation", Presented at the Annual Meeting of American Society of Anesthesiologists, San Francisco, California, Oct. 14-18, 2000 (Abstract A-657).
Leseavre and Eberhard, 1978 ,"Mechanism of action of factor D of the alternative complement pathway," J Exp. Med. 148(6):1498-509.
Loubser et al., 2000, "Inhibition of Complement, Neutrophil, Platelet, and Cytokine Activation by Anti-factor D Antibody During Extracorporeal Circulation," Presented in the American Society of Anesthesiologists 2000 Annual Meeting. San Francisco, California (poster presentation).
Matson et al., 2000, "Evolving concepts of therapy for sepsis and septic shock and the use of hyperpermeable memberanes", Current Opinion in Critical Care 6:431-436.
Morgan, 1994, "Clinical complementology: recent progress and future trends." Eur J. Clin Invest 24(4):219-28.
Mulligan et al., "Protective Effects of Soluble CR1 in Complement and Neutrophil-Medicated Tissue Injury", J. Immunol., 148(5):1479-1485 (1992).
Narayana et al., "Structure of Human Factor D:A Complement System Protein at 20.degree. Resolution", J. Mol. Biol., 235: 695-708 (1994).
Niemann et al., "The Use of Monoclonal Antibodies as Probes of the Three Dimensional Structure of Human Complement Factor D", J. Immunol., 132(2): 809-815 (1984).
Omer et al., 1997, "CA1A2X-competitive inhibitors of farnesyltransferase as anti-cancer agents" Trends Pharmacol Sci. 18(11):434-44.
Pascual et al., 1990, "A monoclonal which antibody which blocks the function of factor D of human complement." J Immunol. Methods 127(2)263-9.
Pascual et al., 1993, "Inhibition of complement alternative pathway in mice with Fab antibody to recombinant adipsin/factor D." Eur J. Immunol. 23(6): 1389-92.
Rabinovici et al., 1992, "Role of compleent in endotoxin/platelet-activating factor-induced lung injyr." J. Immunol. 149(5):1744-50.
Ray et al., 1997, "Thrombin receptor: a novel target for antiplatelet drug development" Thromb Res. 87 (1): 37-50.
Ricklin and Lambris, 2007, "Complement-targeted therapeutics." Nat Biotechnol. 25(11):1265-75.
Rinder et al., 1995, "Blockade of C5a and C5b-9 generation inhibits leukocyte and platelet activation during extracorporeal circulation." J. clin. Invest. 96(3):1564-72.
Sahu et al., 1993, "Identification of multiple sites of interaction between heparin and the complement system" Mol. Immunol. 30(7): 679-84.
Sato et al., 1997, "A new method for studying the binding of human IgE to CD23 and the inhibition of this binding." J Immunol. Methods 209(1): 59-66.
Sim et al., "Serine Proteases of the Complement System", Biochemical Society Transactions, vol. 28, Pt.5, pp. 545-550 (2000).
Stadel et al., 1997, "Orphan G protein-coupled receptors: a neglected opportunity for pioneer drug discovery" Trends Pharmacol. Sci 18(11): 430-7.
Strawn et al., 1996, "FLK-1 as a Target Tumor Growth Inhibition." Cancer Resarch. 56:3540-3545.
Tanhehco et al., 1999. "The anti-factor D antibody, MAb 166-32, inhibits the alternative pathway of the human complement system." Transplant Proc. 31(5):2168-71.
Ündar et al., "Novel Anti-Factor D Monoclonal Antibody Inhibits Complement, Neutrophil, and Platelet Activation in a Simulated Pediatric Cardioplumonary Bypass Circuit"., Presented in the 46th Annual Conference of the American Society for Artificial Internal Organs, New York, N.Y., Jun. 28-Jul. 1, 2000, (Abstract).
Undar et al., 2000 "Novel Anti-Factor D Monoclonal Antibody Inhibits Complement, Neutrophil, and Platelet Activation in a Simulated Pediatric Cardiopulmonary Bypass Circuit." Presented in the 46th Annual Conference of the American Society for Artificial Internal Organs. New York, NY (Abstract only).
Volanakis et al., "Complement Enzymes", In: *The Human Complement System in Health & Disease*, Chapter 4, pp. 49-81, Eds., J. Volonakis & M. M. Frank, Published by Marcel Dekker, Inc. New York (1998).
Volanakis et al., "Complement Factor D, A Novel Serine Protease", Protein Science, 5:553-564 (1996).
Wang et al., 1995, "Anti-CS monoclonal antibody therapy prevents collage-induced arthritis and ameliorate established disease." Proc. Nalt. Acad Sci. 92(19):8955-9.
Wang et al., 1996, "Amelioration of Lupus-like Autoimmune Disease in NZB/W $F_1$ Mice After Treatment with a Blocking Monoclonal Antibody Specific for Complement Component C5" Proc. Natl Acad Sci 94:8563-8568.
Weisman et al., 1990, "Soluble human complement receptor type 1: in vivo inhibitor of complement suppressing post-ischemic myocardial inflammation and necrosis." Science 249(4965):146-51.
White et al., "Human Adipsin is Identical to Complement Factor D and is Expressed at High Levels in Adipose Tissue", J. Bio. Chem, 267(13): 9210-9213 (1992).
Wilson et al., 1993, "A competitive inhibition ELISA for the quantification of human interferon-gamma" J. Immunol. Methods 162(2):247-55.

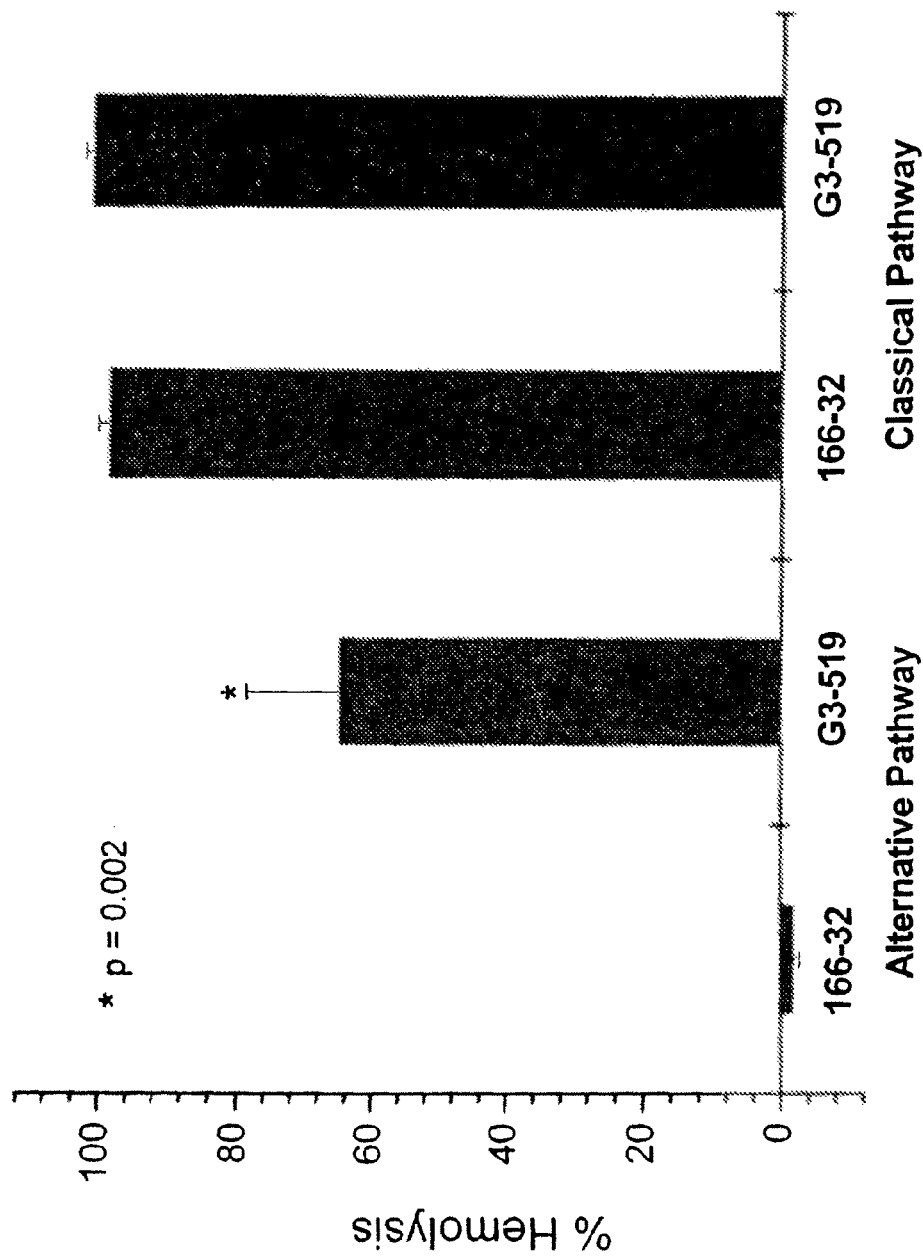
Fig. 26 Selective inhibition of the alternative complement pathway by anti-factor D MAb 166-32

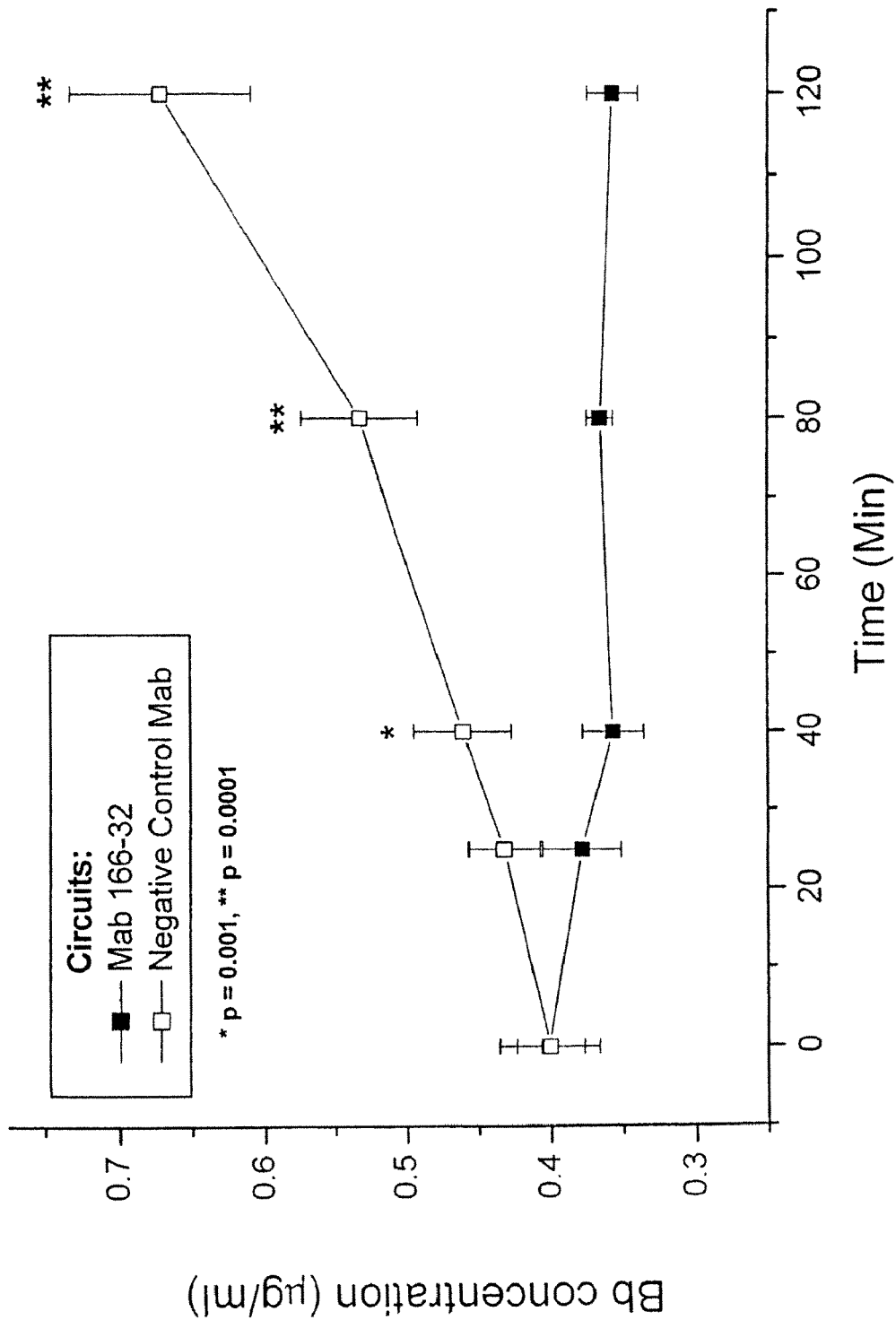
Fig. 27 Bb production in extracorporeal circuits

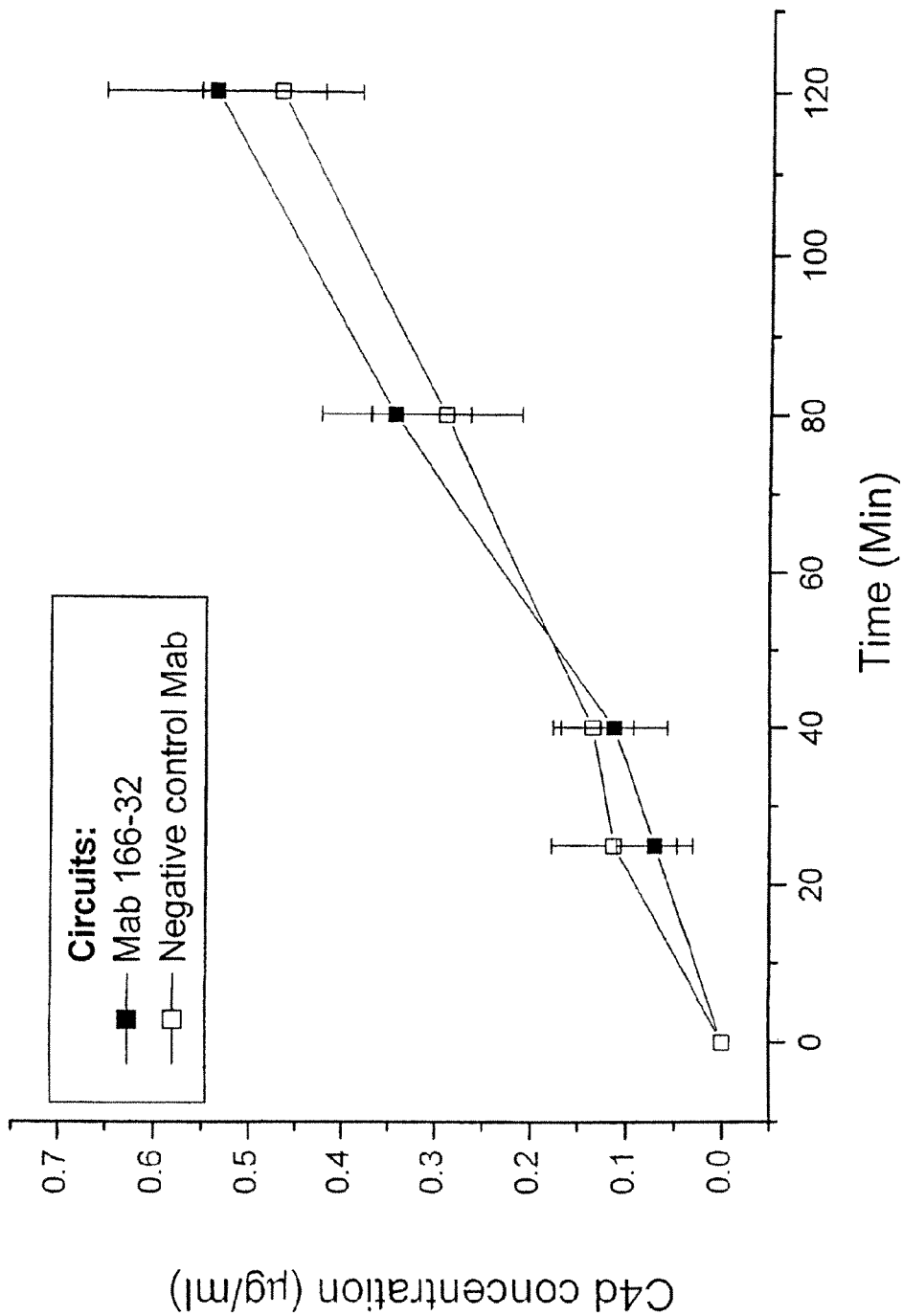

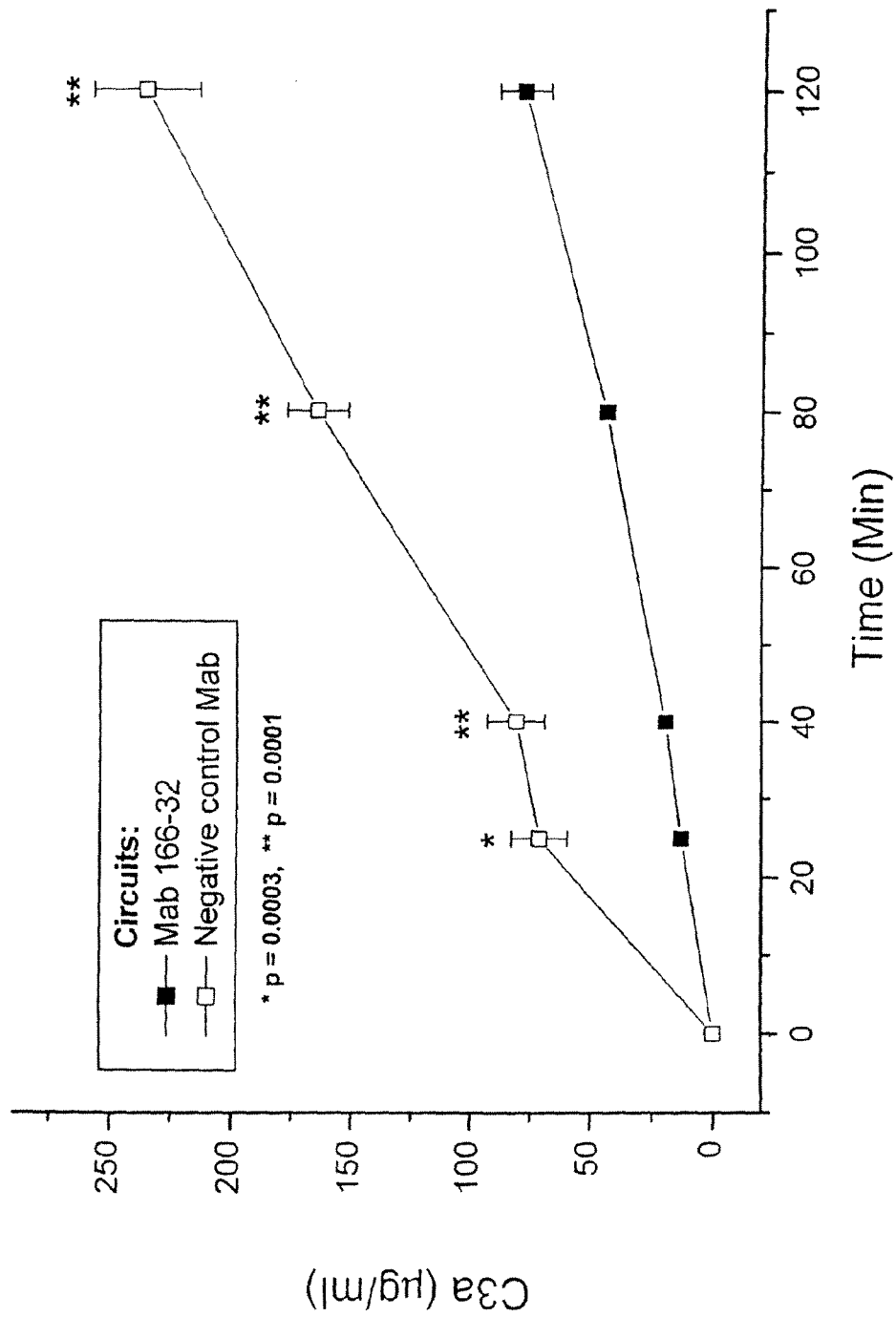
Fig. 29 C3a production in extracorporeal circuits

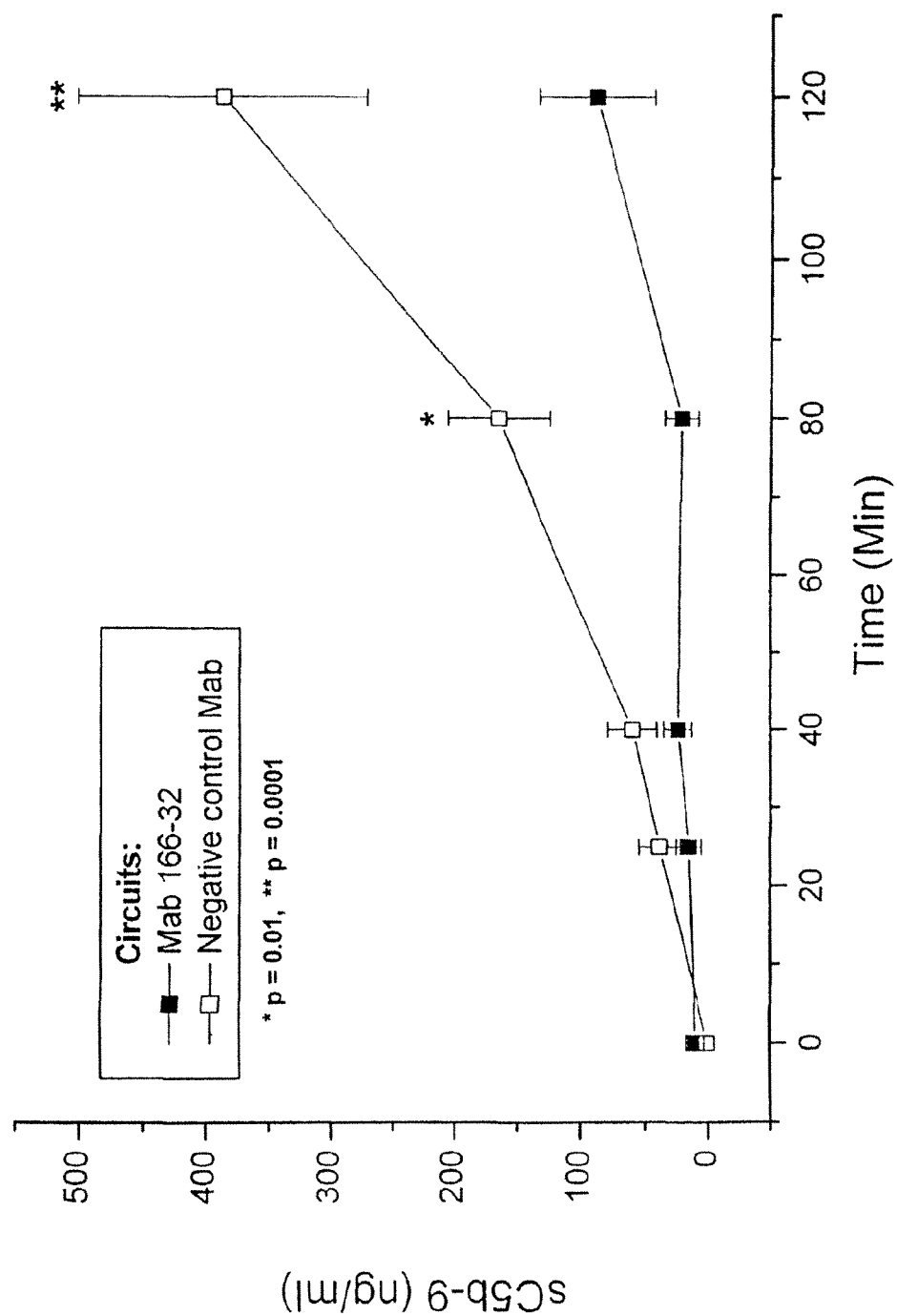

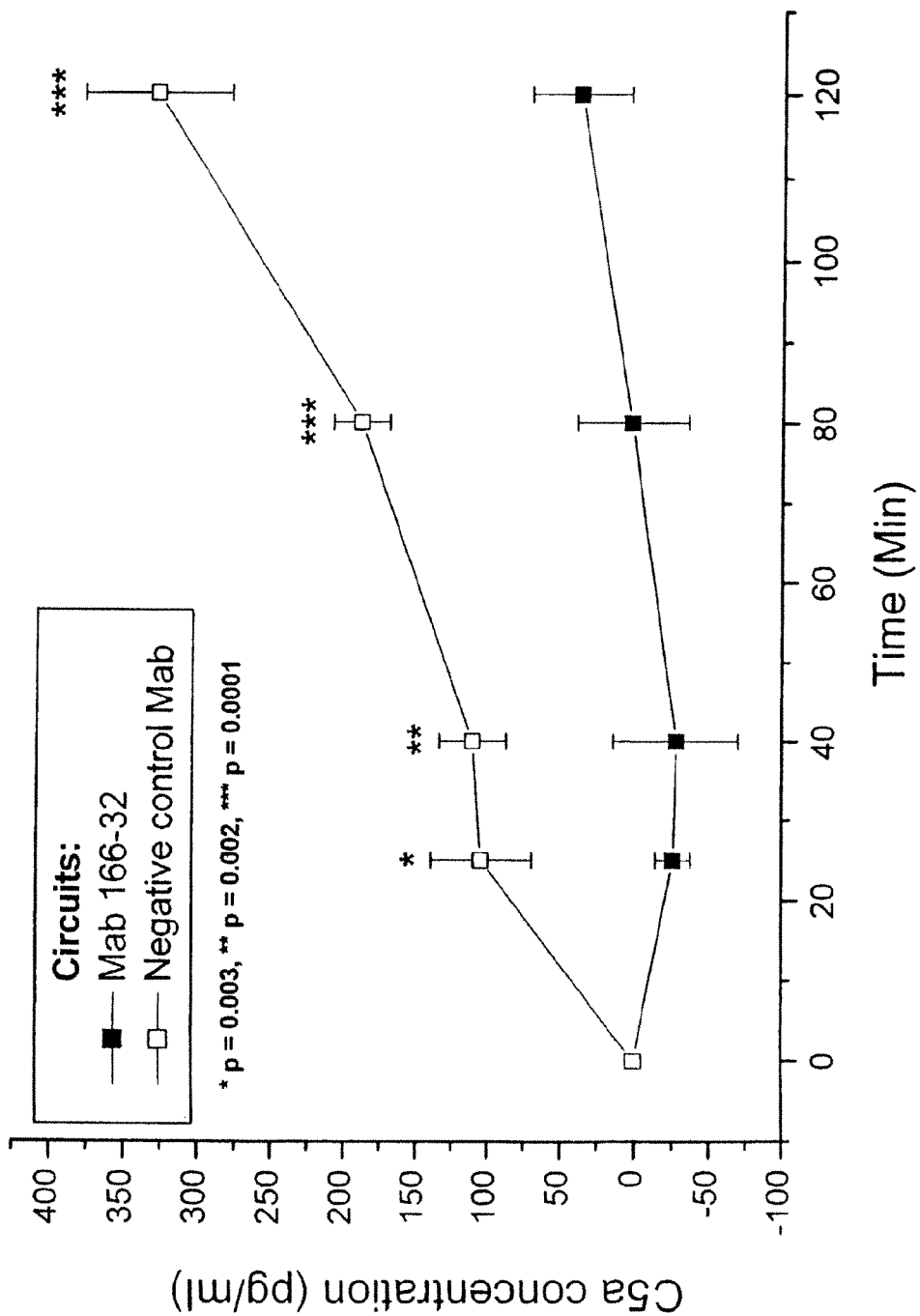
Fig. 31 C5a production in extracorporeal circuits

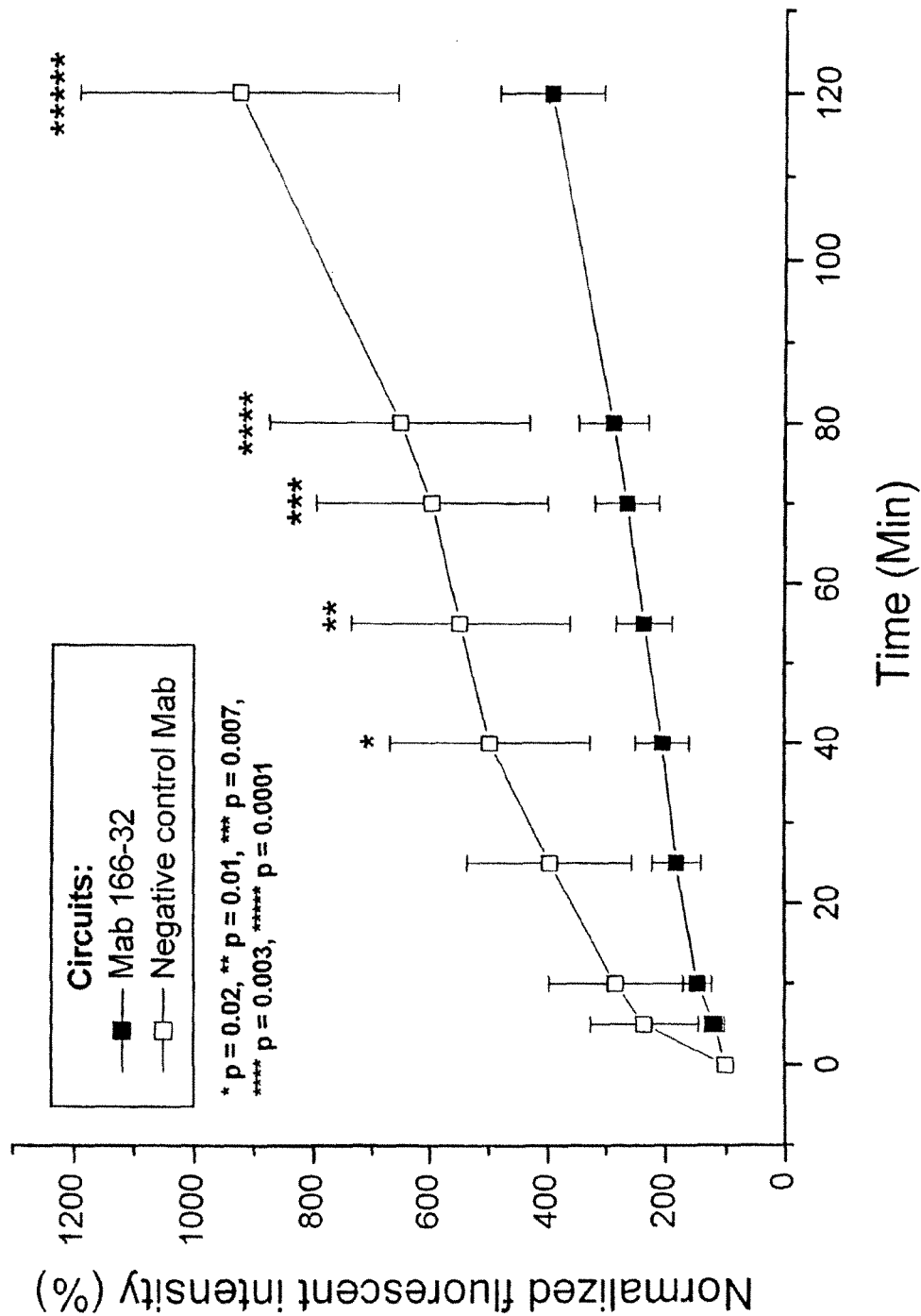
Fig. 32  CD11b expression on neutrophils in extracorporeal circuits

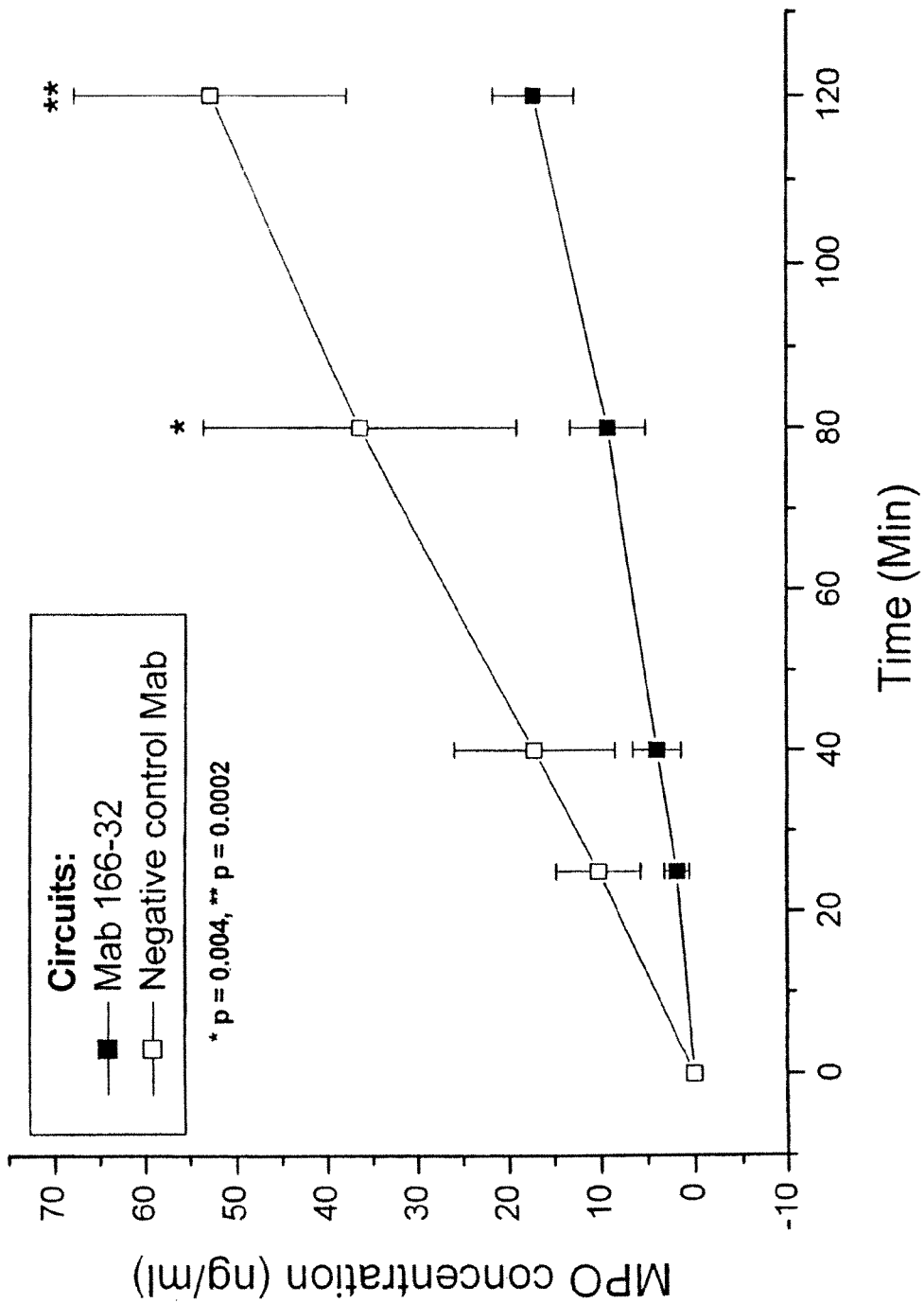
Fig. 33 Myeloperoxidase production in extracorporeal circuits

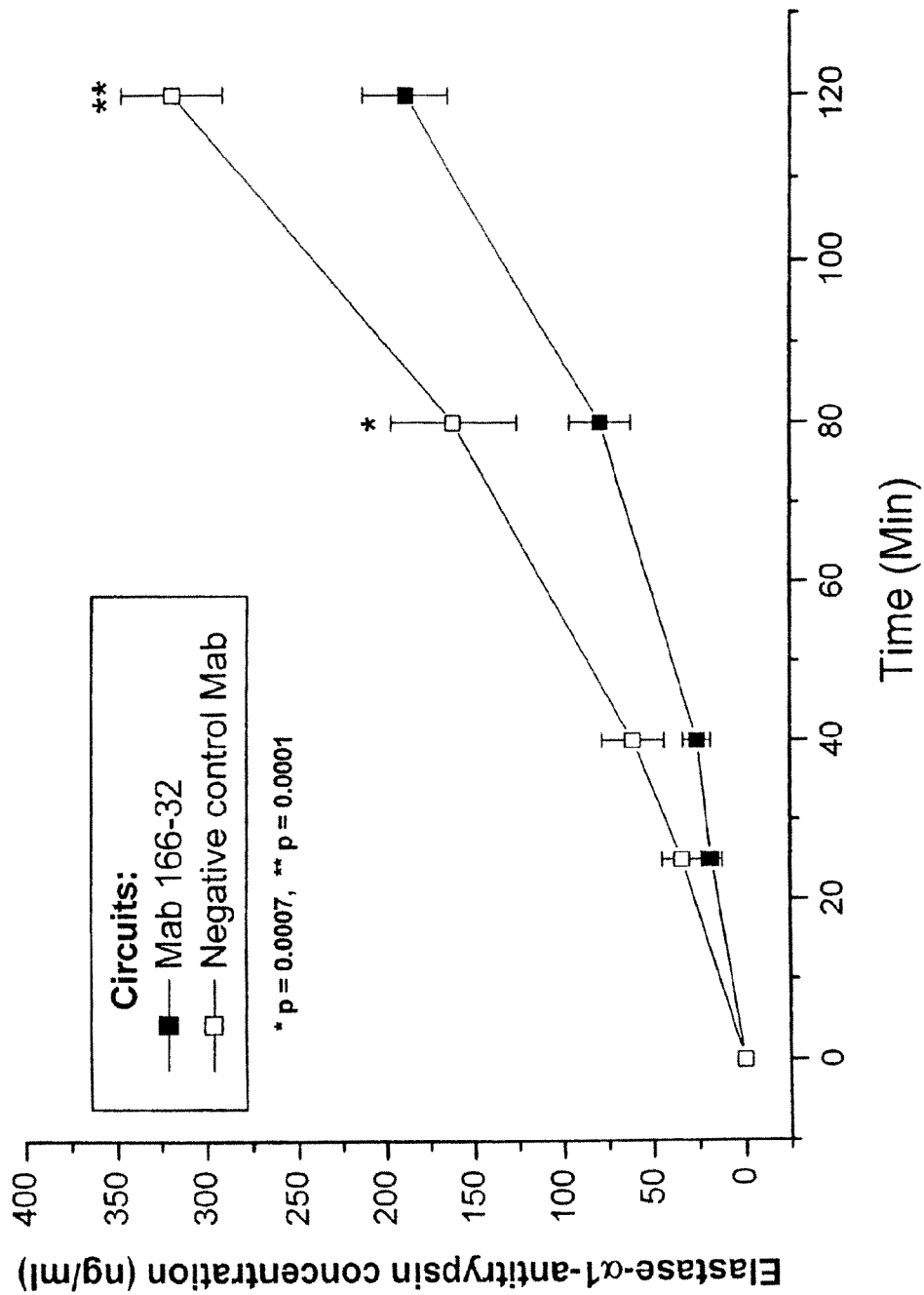

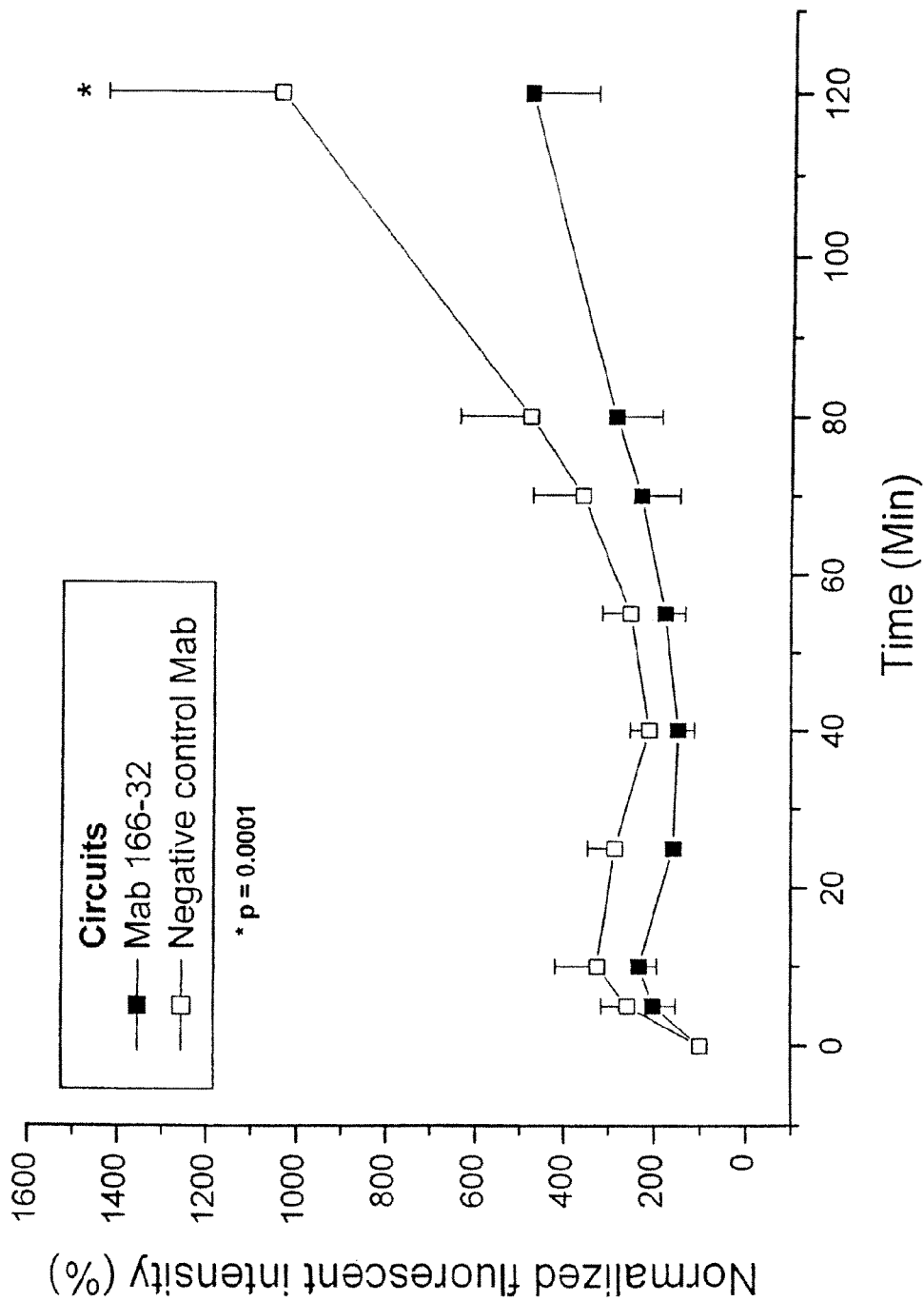

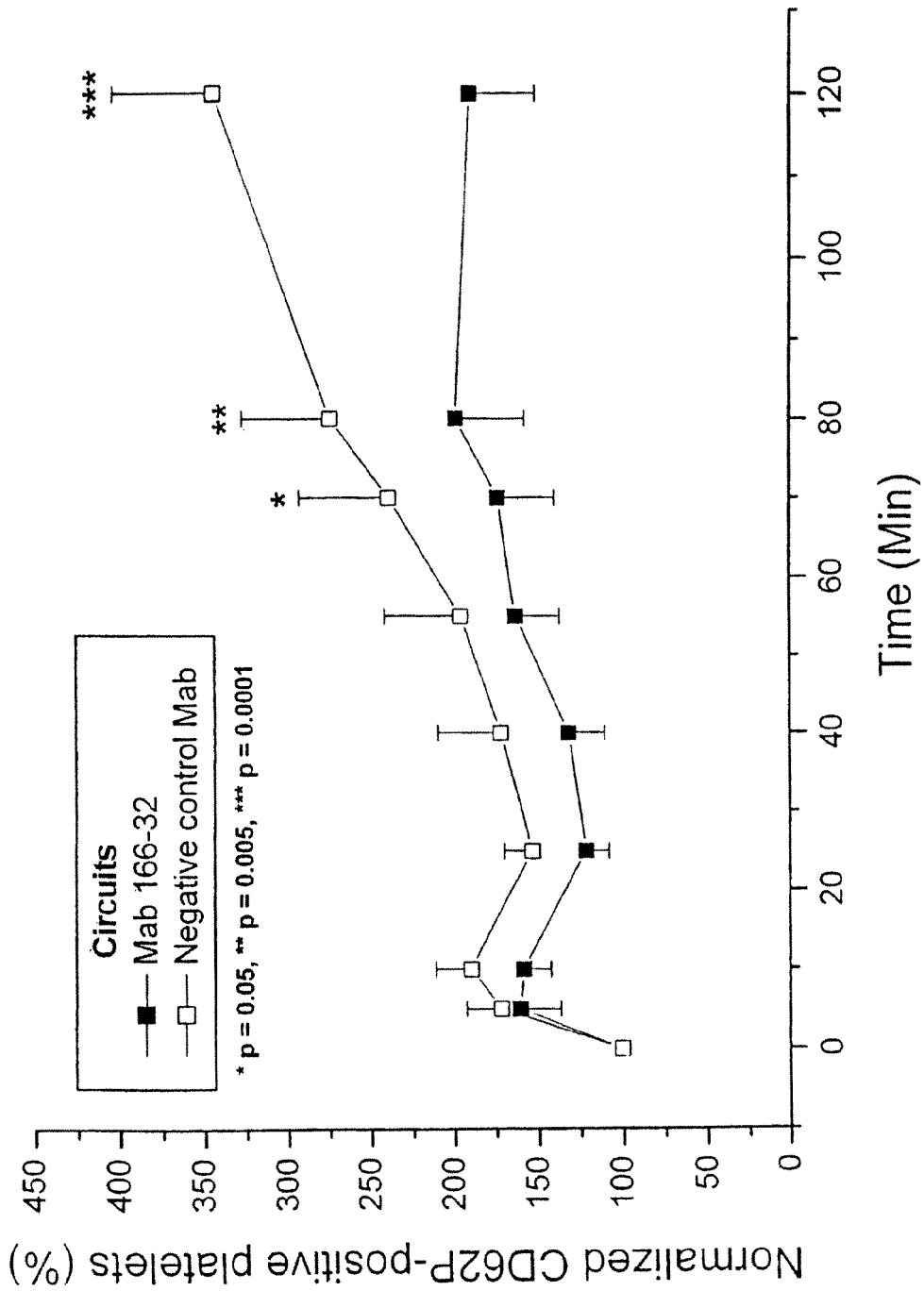

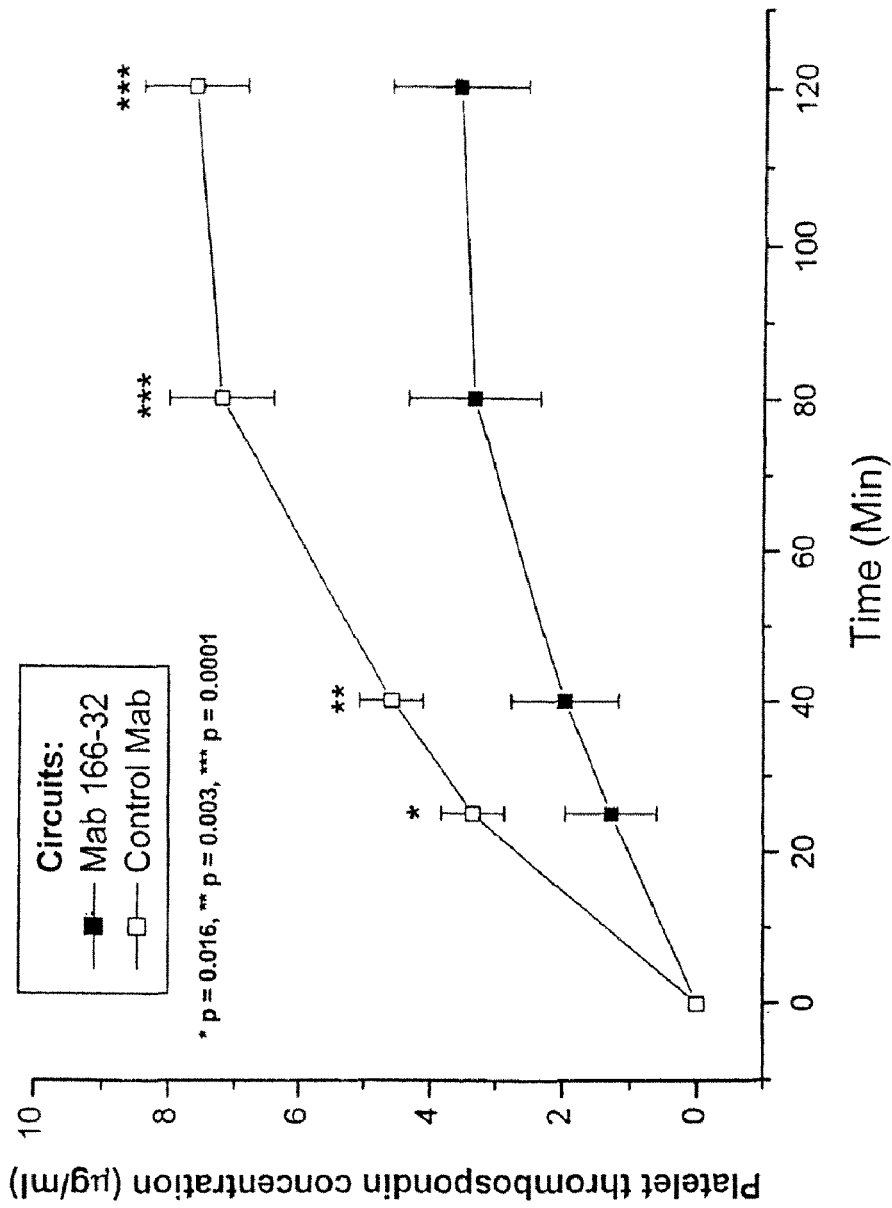
Fig. 37 Platelet thrombospondin production in extracorporeal circuits

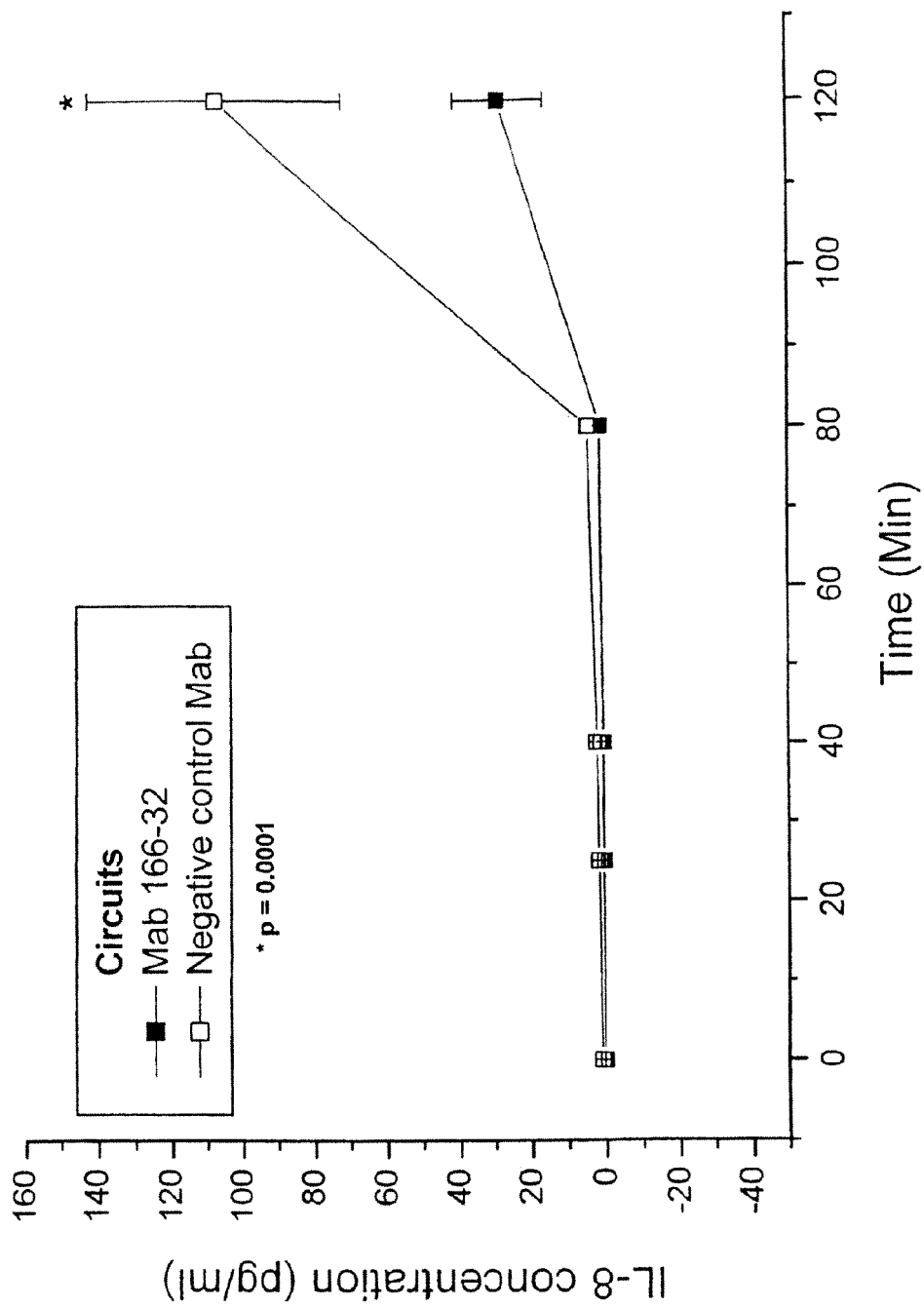
Fig. 38 IL-8 production in extracorporeal circuits

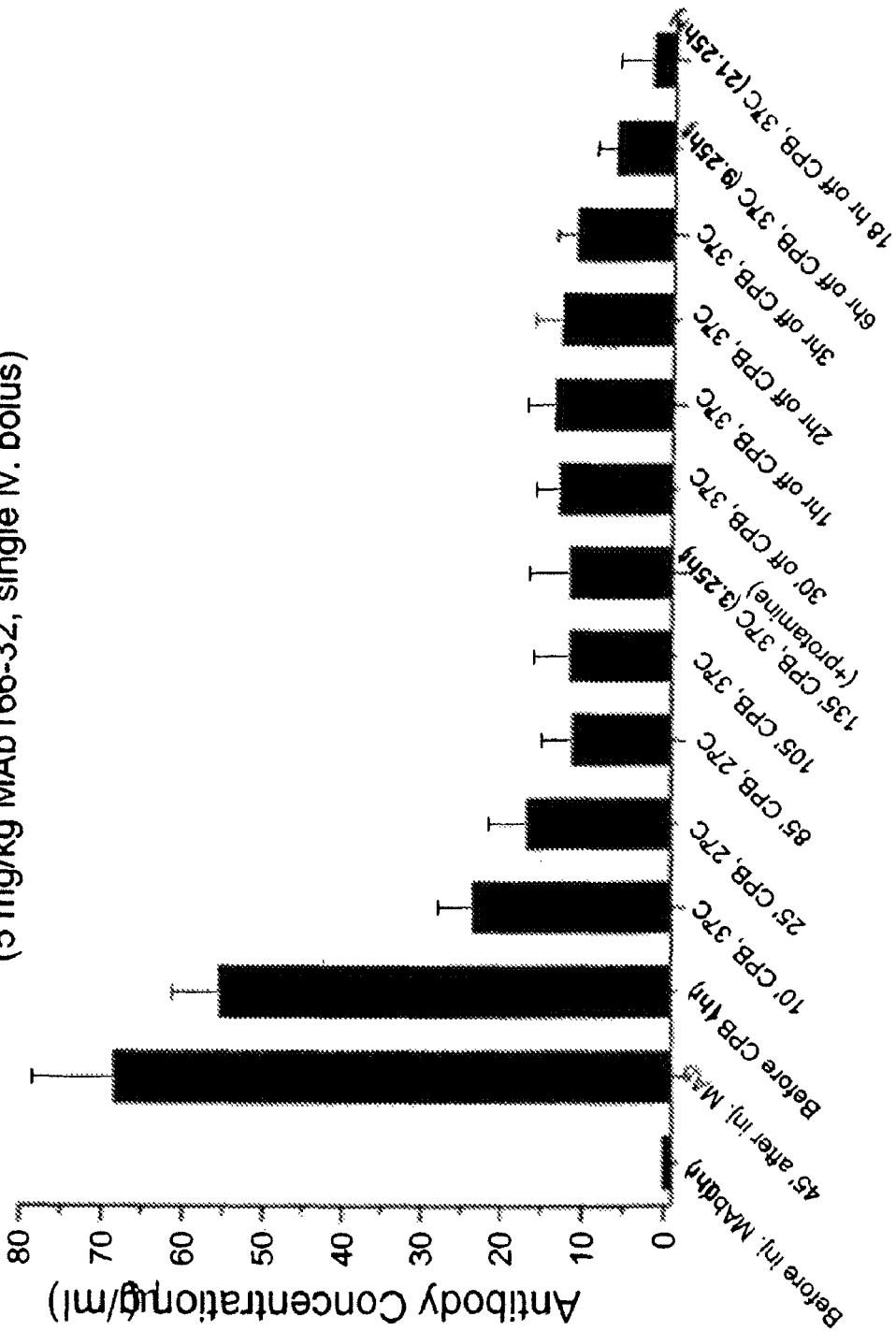
Fig. 39 Pharmacokinetics of MAb166-32 in Baboon CPB

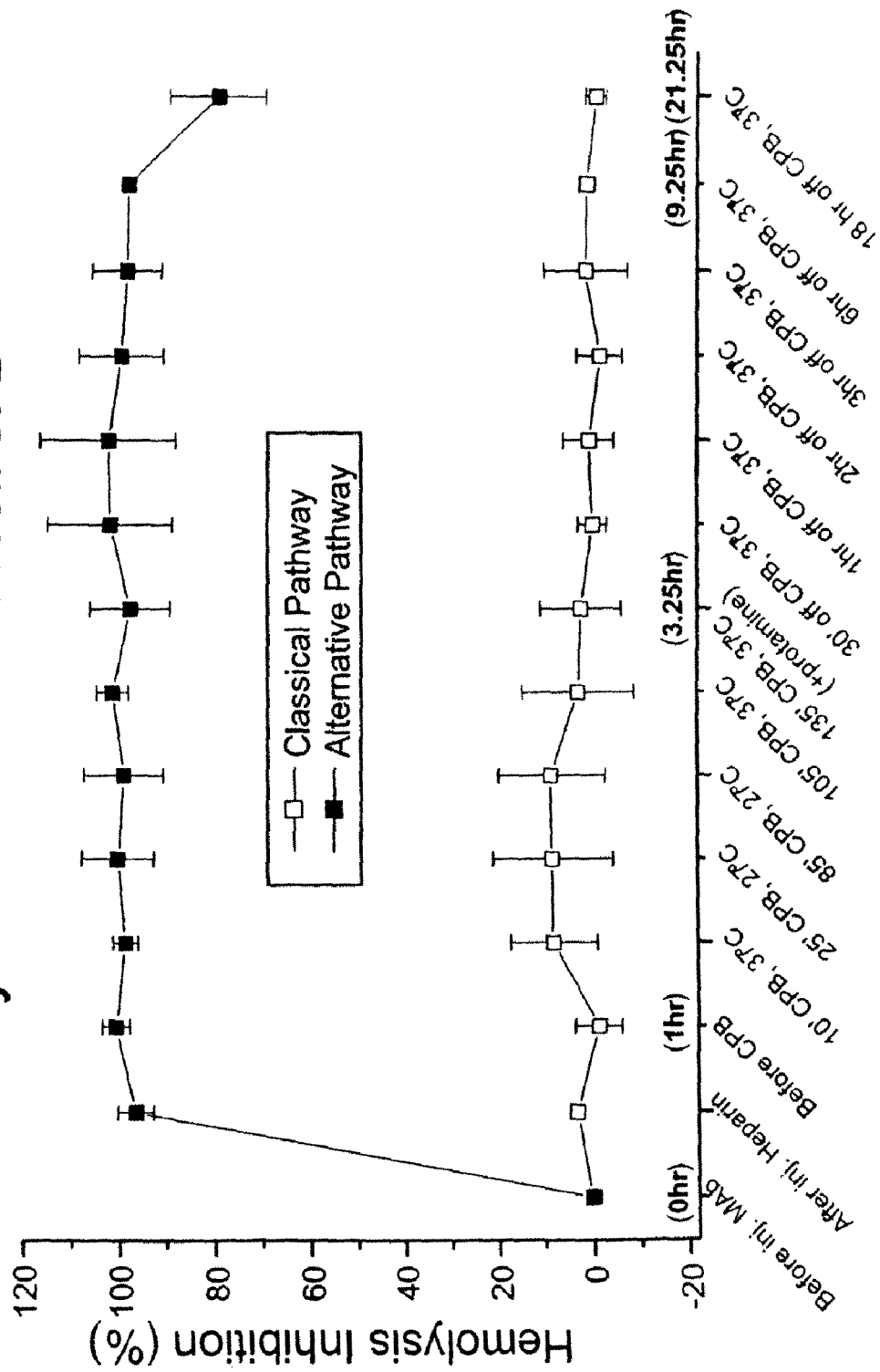

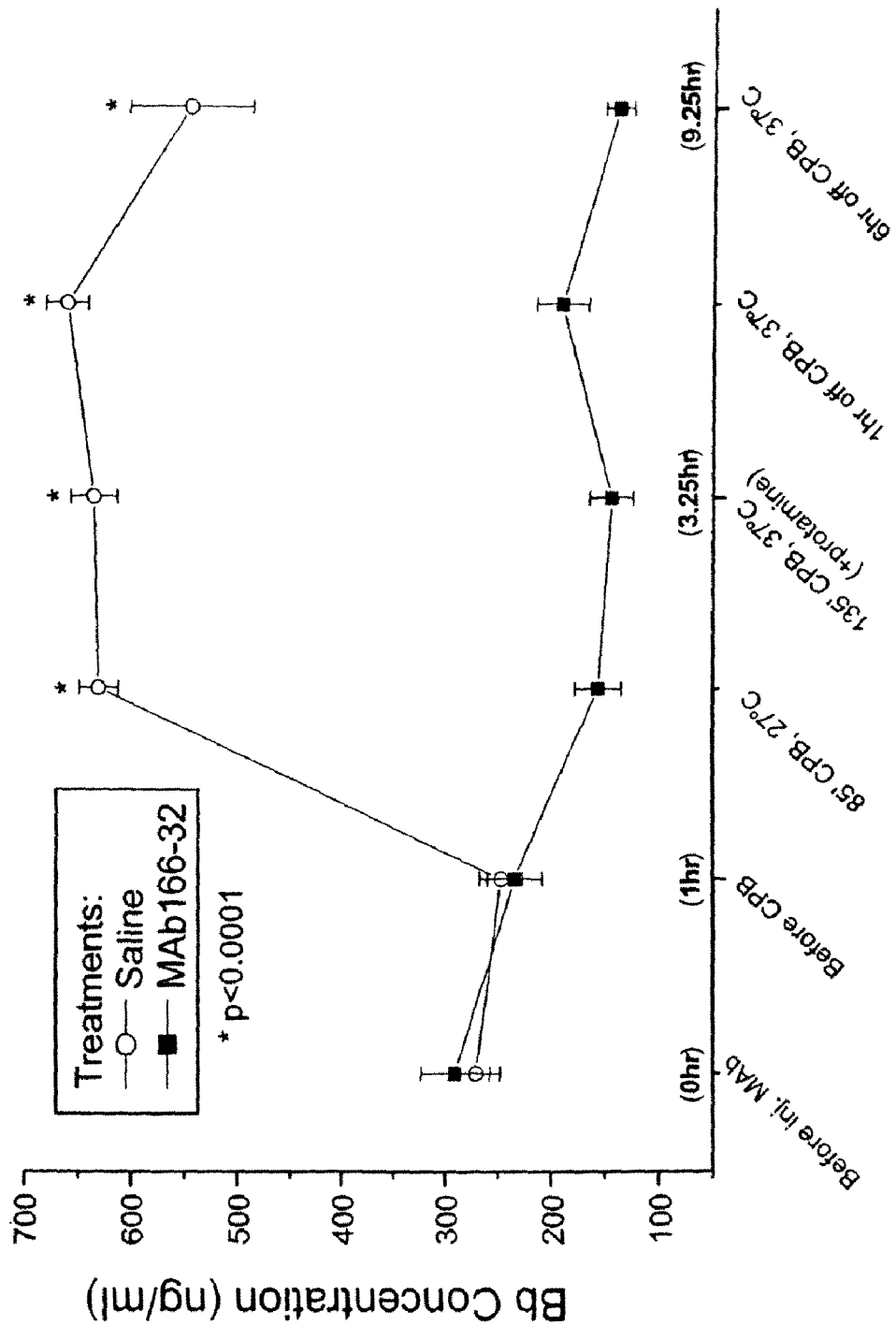
Fig. 41 Bb in Baboon CPB

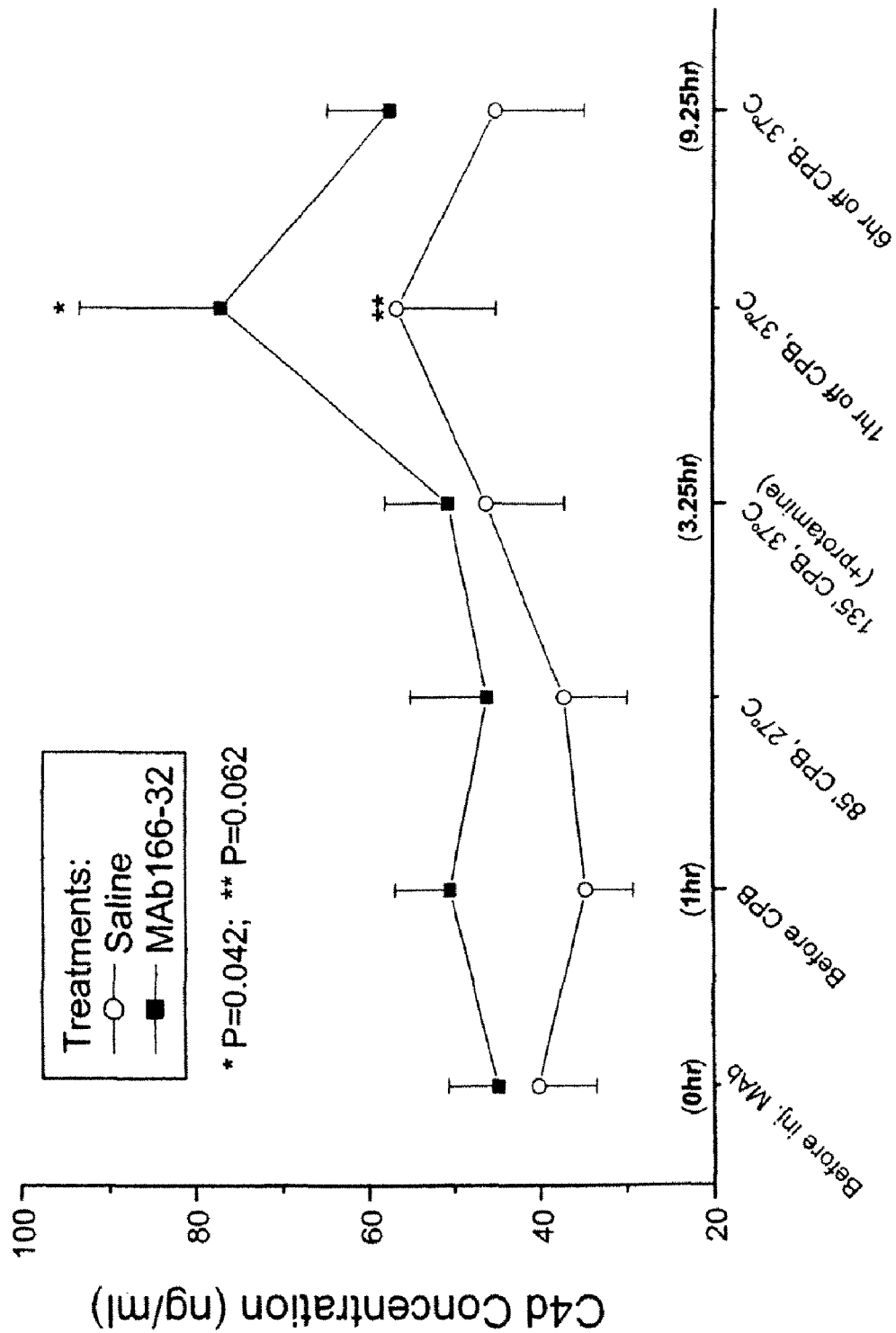
Fig. 42 C4d in Baboon CPB

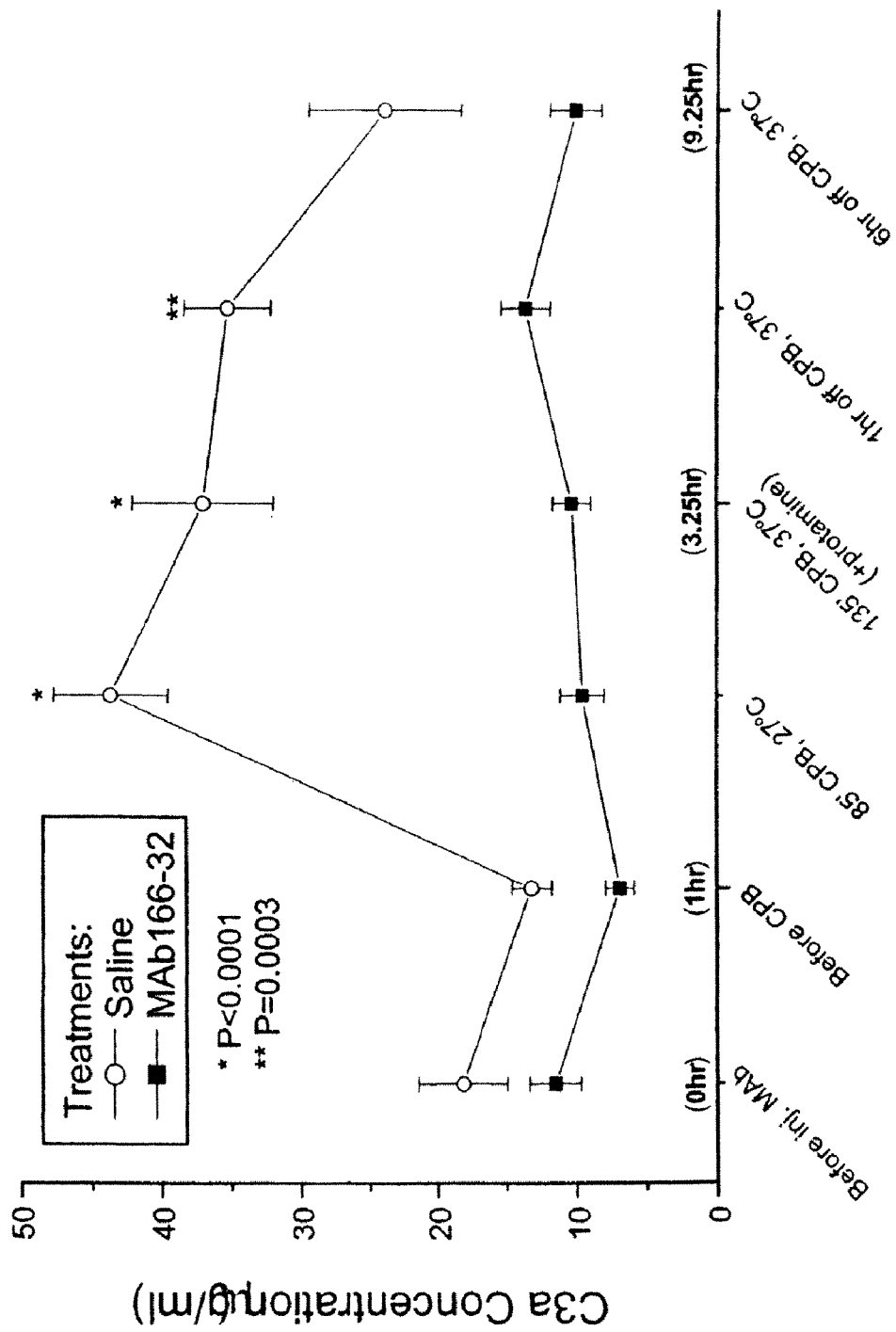

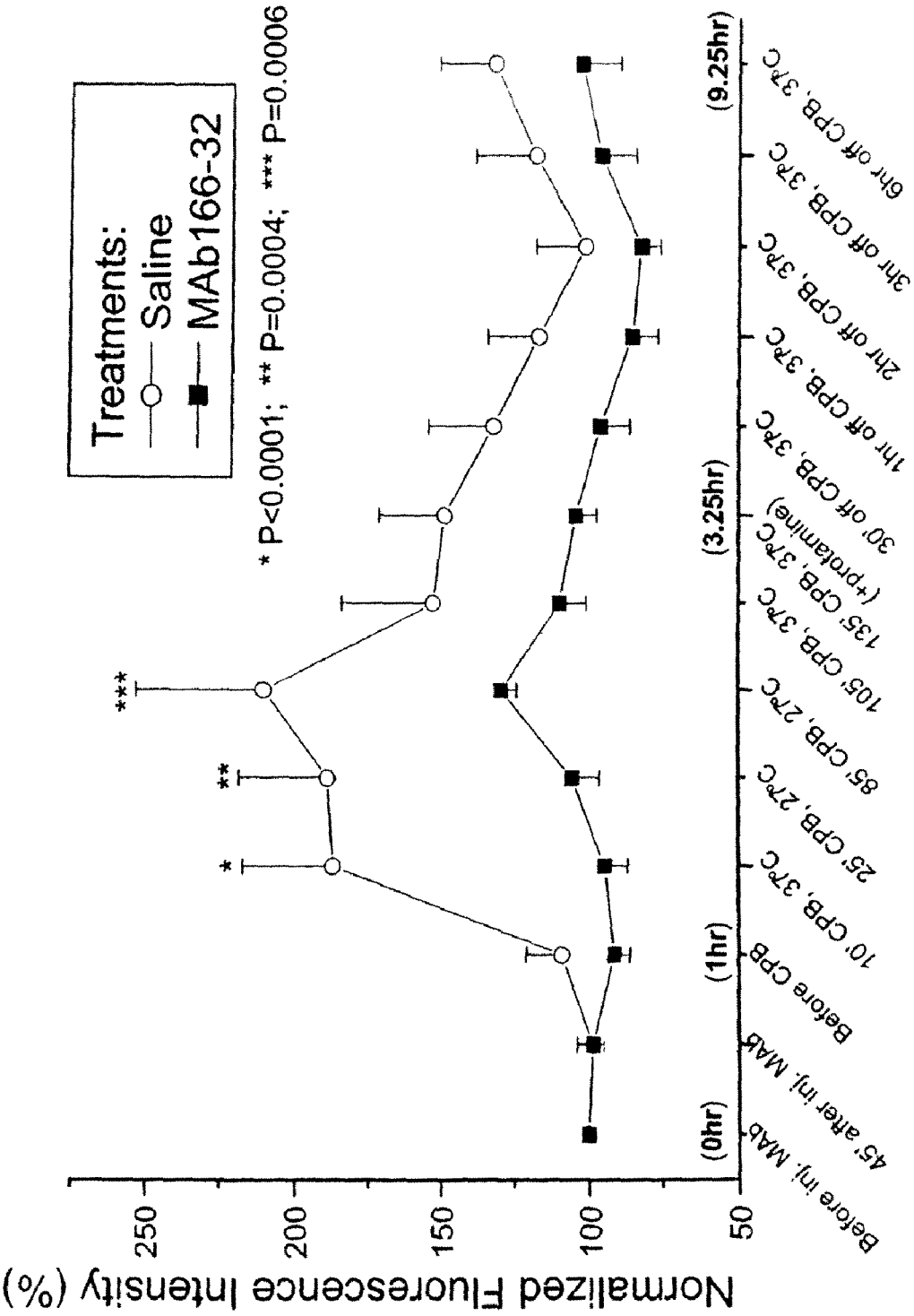
Fig. 44 CD11b Expression on Neutrophils in Baboon CPB

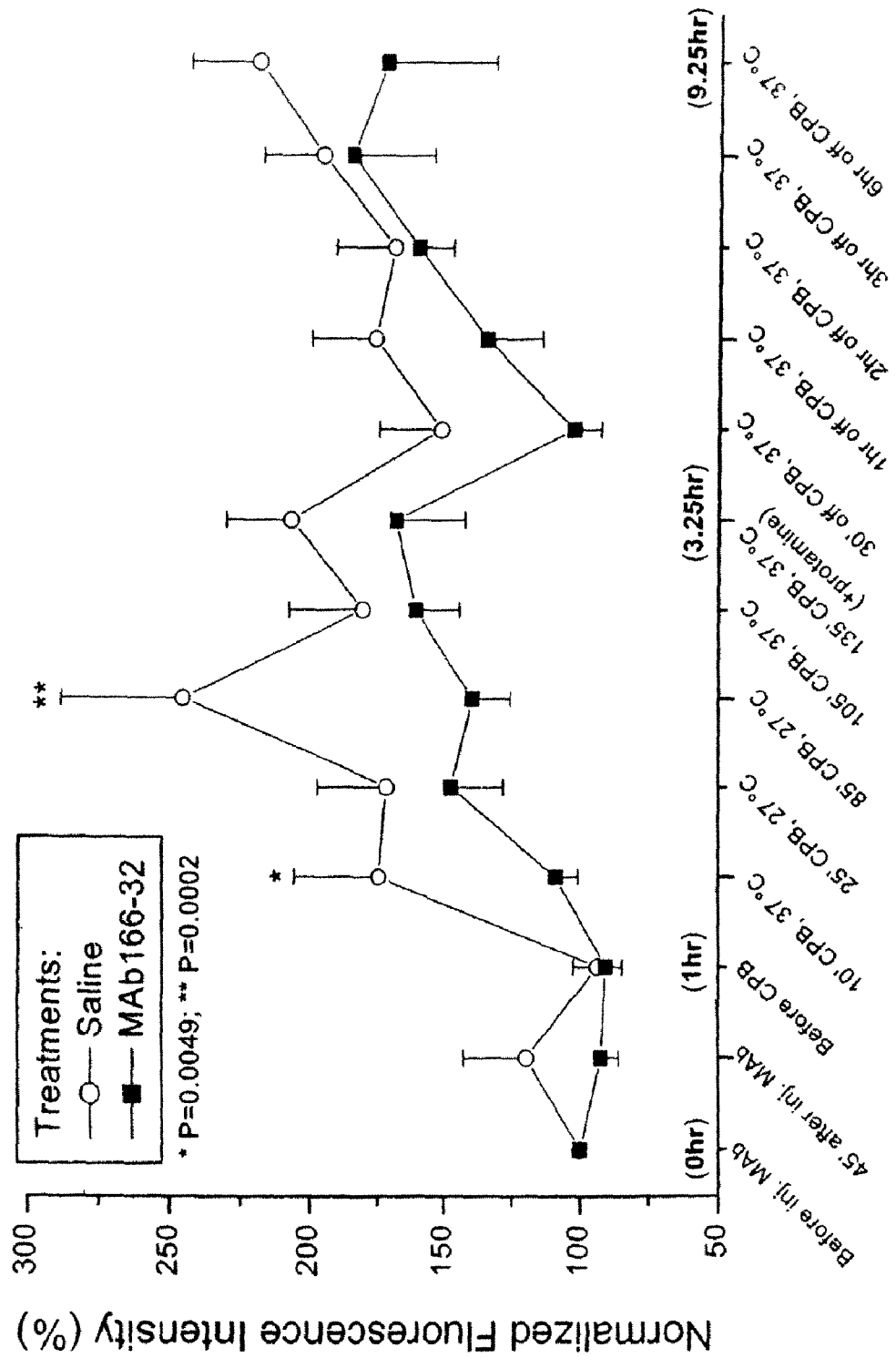

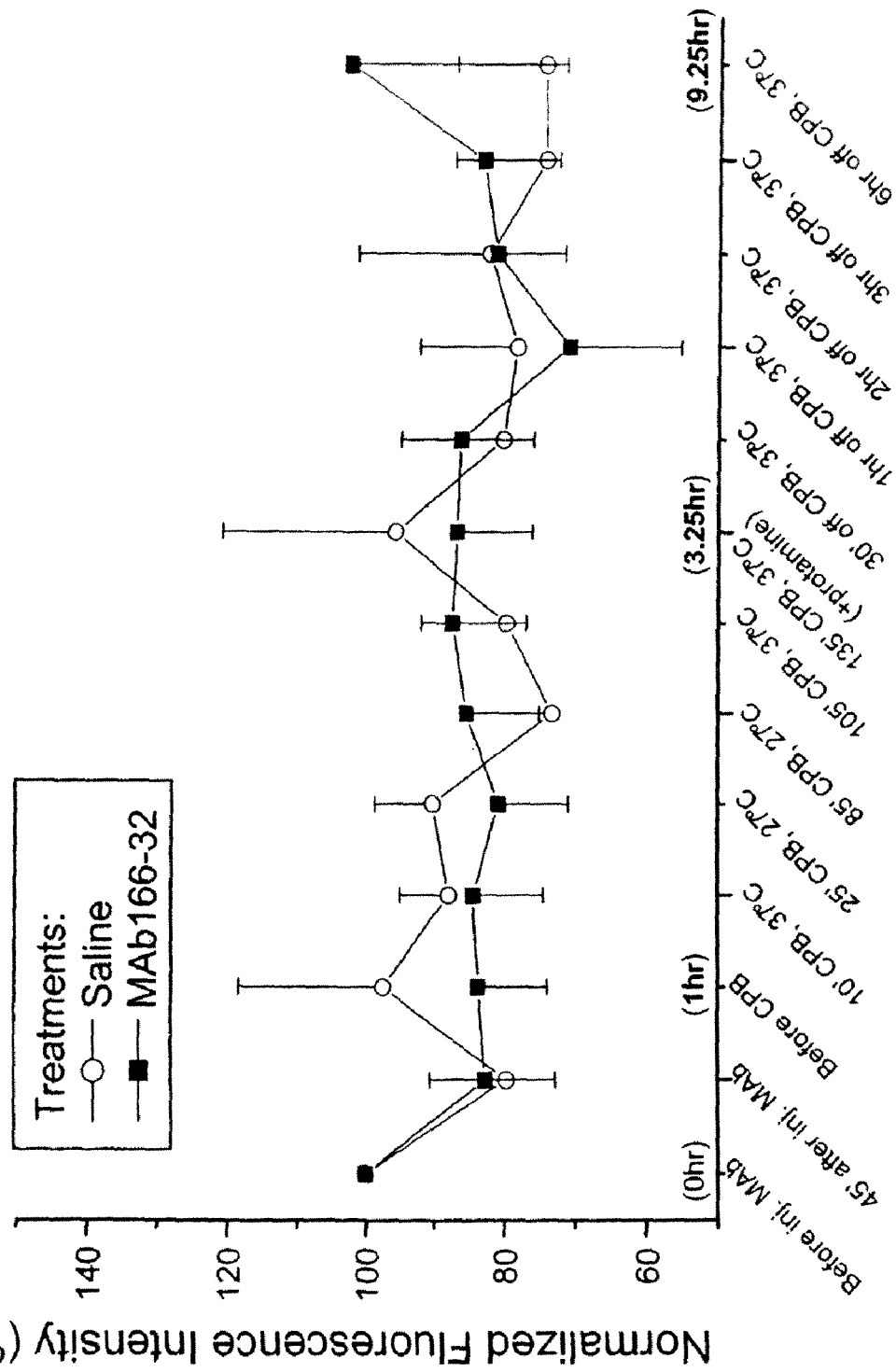
Fig. 4b CD62P Expression on Platelets in Baboon CPB

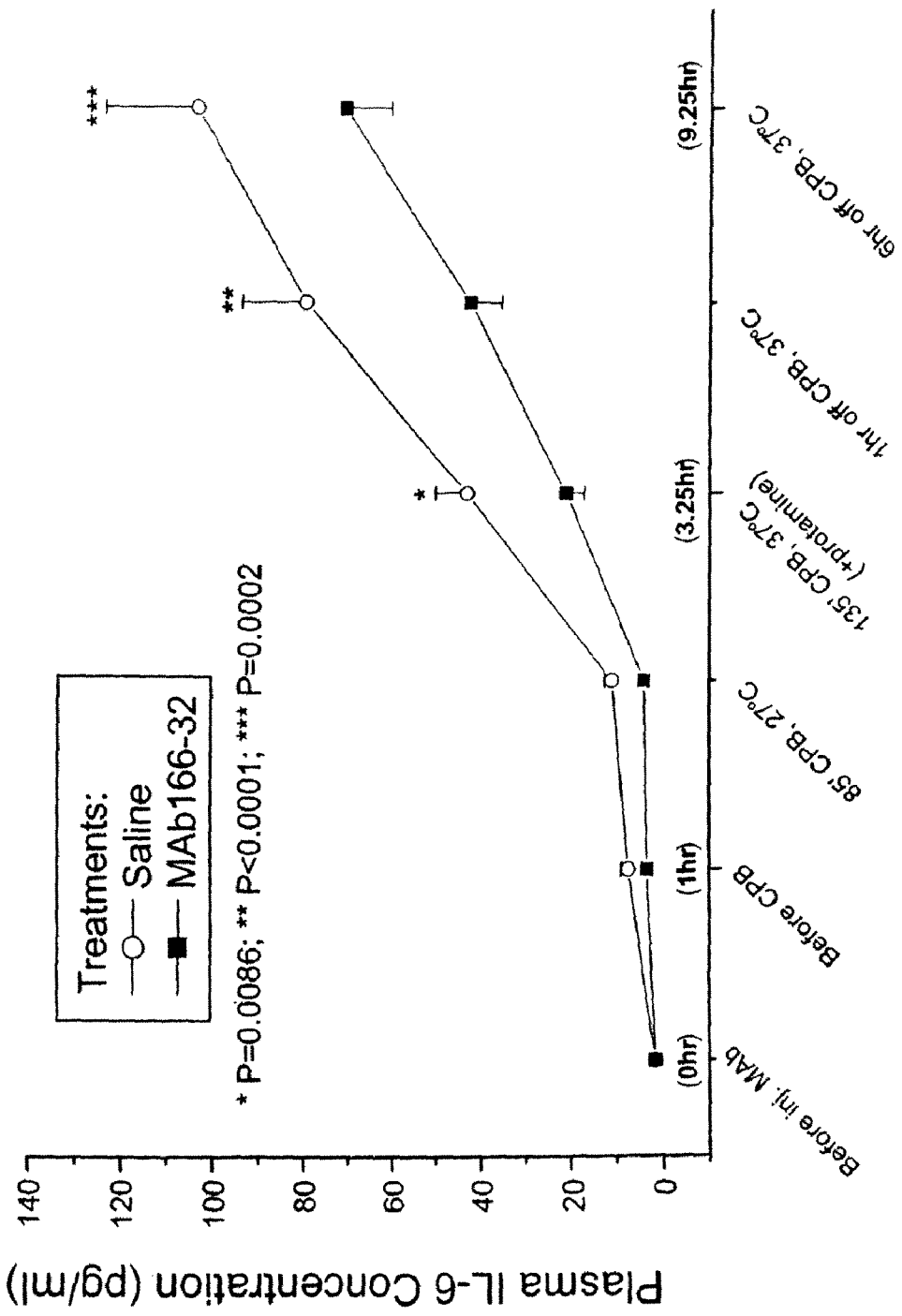

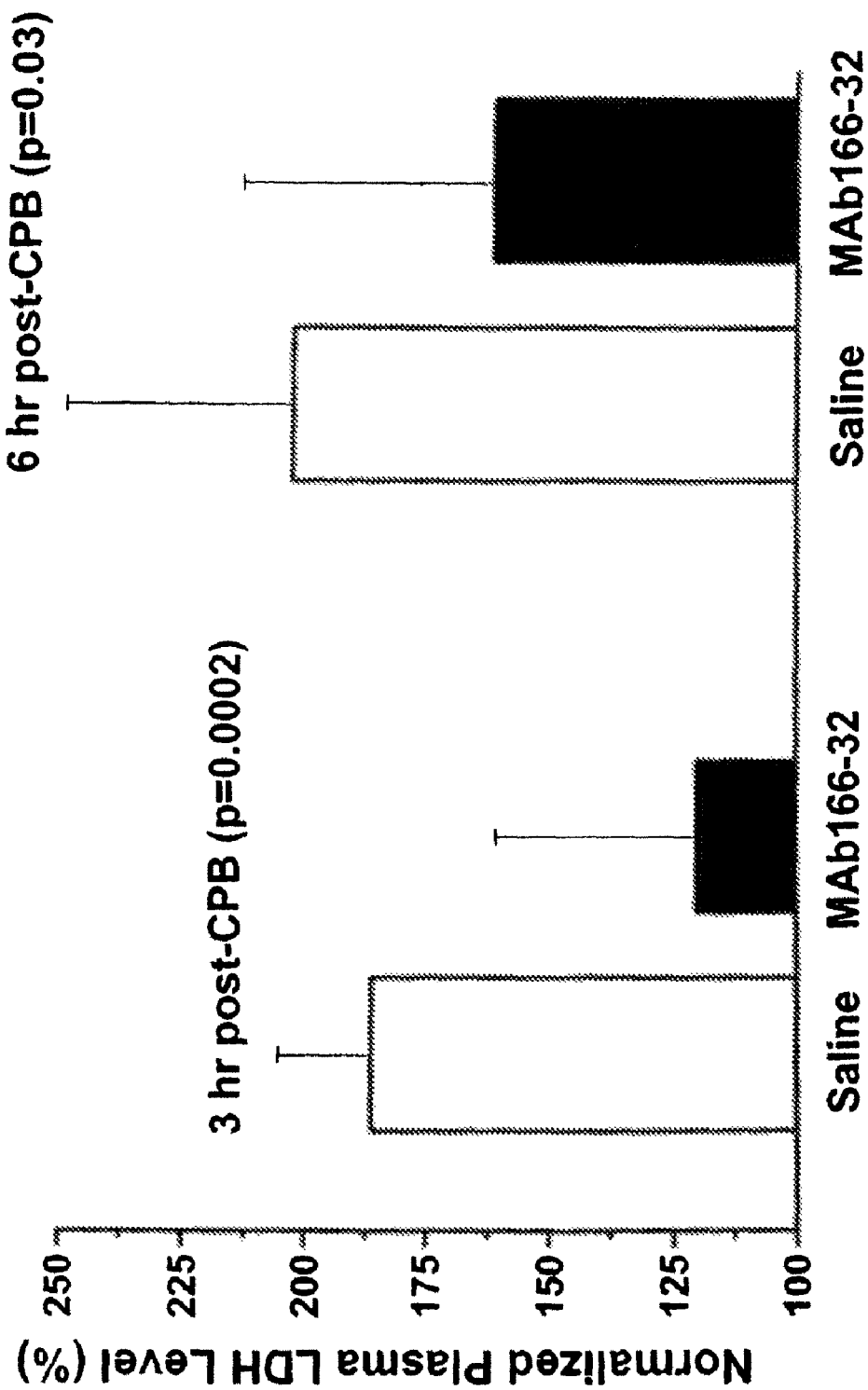
Fig. 48 Plasma LDH Level in Baboon CPB

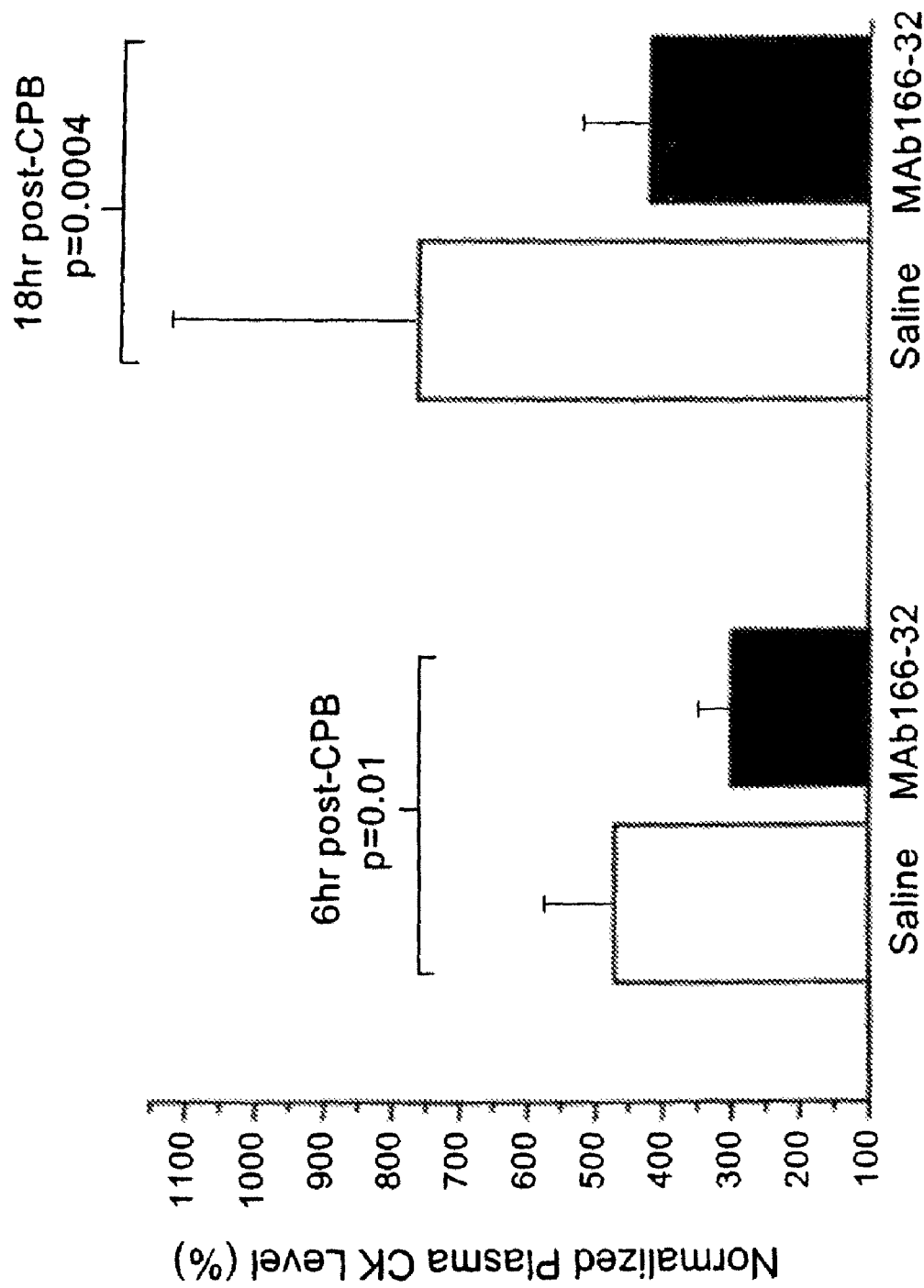
Fig. 49 Plasma Creatine Kinase (CK) Level in Baboon CPB

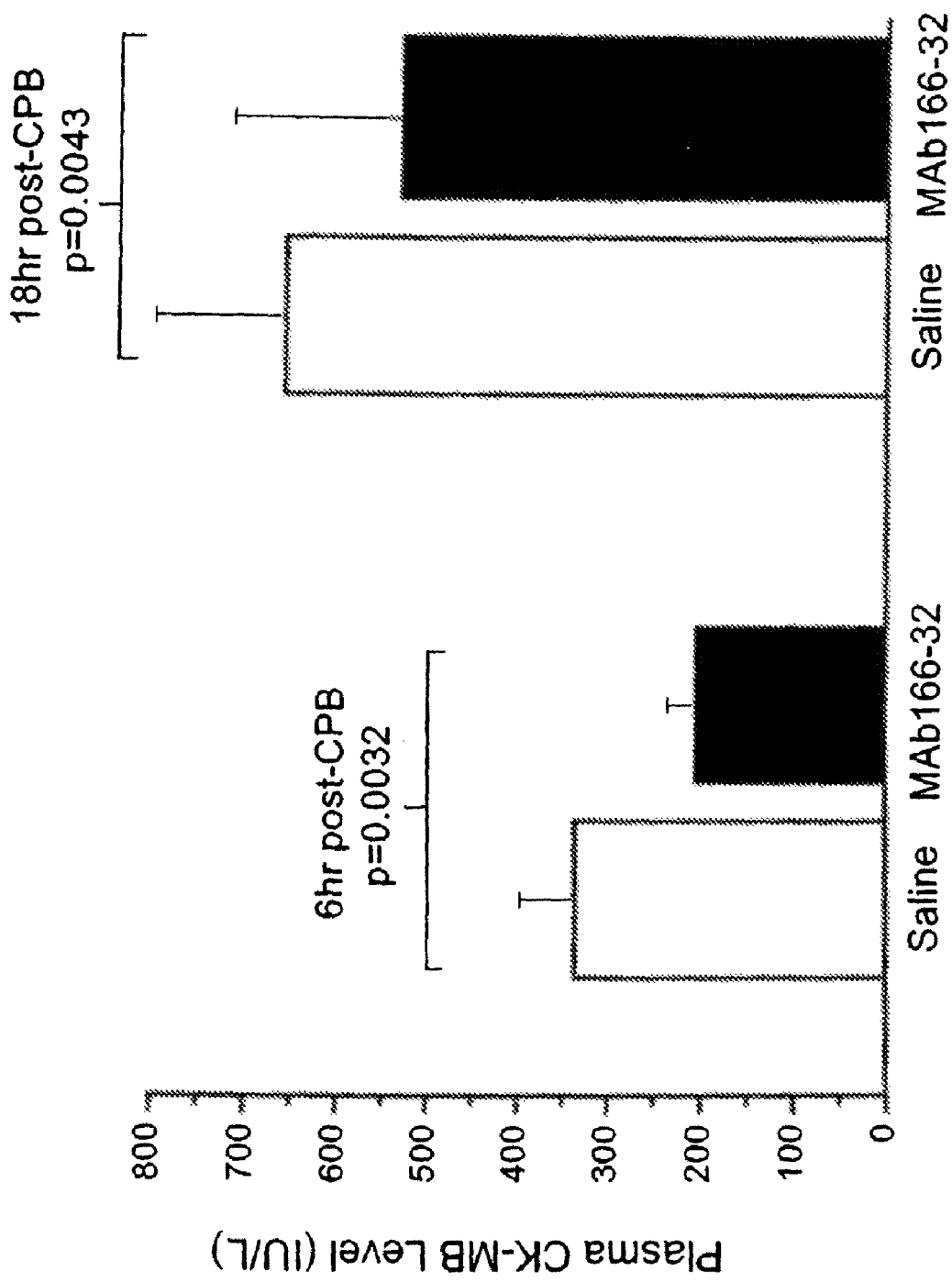

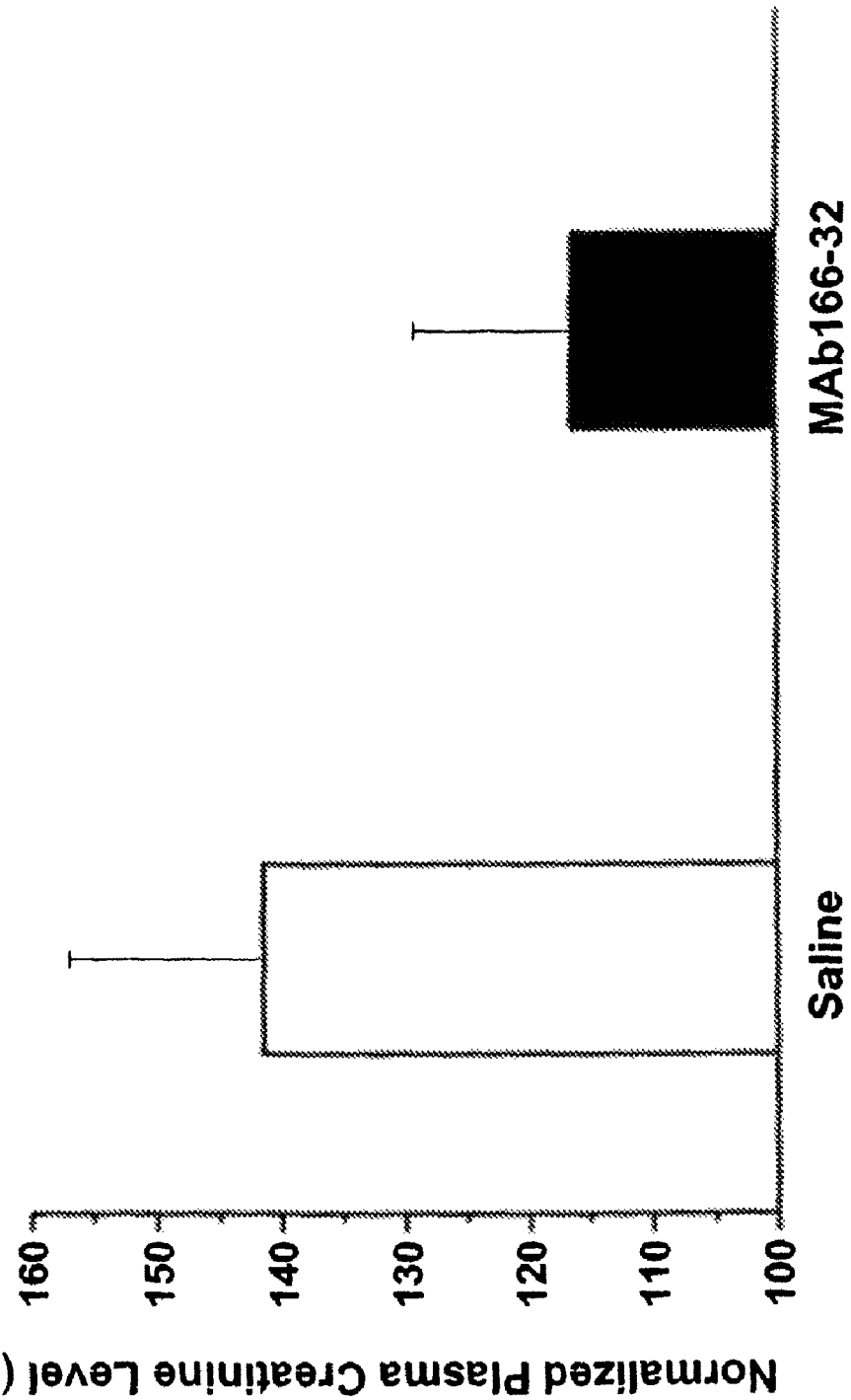
Fig. 51 Plasma Creatinine Level in Baboon CPB

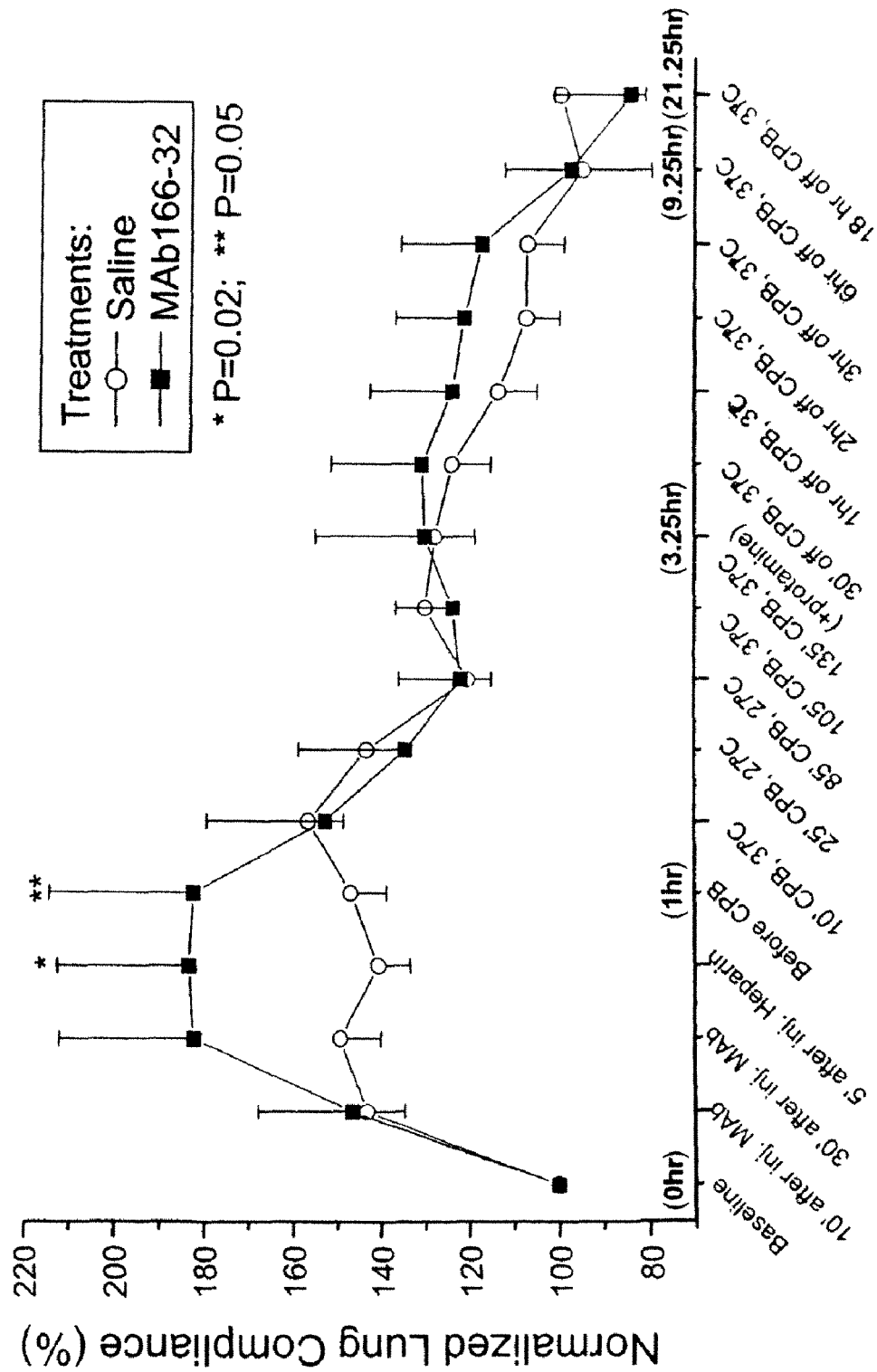

SEQUENCE LISTING

<160> NUMBER OF SEQ ID NOS: 15

<210> SEQ ID NO 1
<211> LENGTH: 699
<212> TYPE: DNA
<213> ORGANISM: Homo sapiens

<400> SEQUENCE: 1

```
cggatcctgg gcggcagaga ggccgaggcg cacgcgcggc cctacatggc gtcggtgcag      60
ctgaacggcg cgcacctgtg cggcggcgtc ctggtggcgg agcagtgggt gctgagcgcg     120
gcgcactgcc tggaggacgc ggccgacggg aaggtgcagg ttctcctggg cgcgcactcc     180
ctgtcgcagc cggagccctc caagcgcctg tacgacgtgc tccgcgcagt gccccacccg     240
gacagccagc ccgacaccat cgaccacgac ctcctgctgc tacagctgtc ggagaaggcc     300
acactgggcc ctgctgtgcg cccctgccc tggcagcgcg tggaccgcga cgtggcaccg     360
ggaactctct gcgacgtggc cggctgggc atagtcaacc acgcgggccg ccgcccggac     420
agcctgcagc acgtgctctt gccagtgctg gaccgcgcca cctgcaaccg gcgcacgcac     480
cacgacggcg ccatcaccga gcgcttgatg tgcgcggaga gcaatcgccg ggacagctgc     540
aagggtgact ccgggggccc gctggtgtgc ggggcgtgc tcgagggcgt ggtcacctcg     600
ggctcgcgcg tttgcggcaa ccgcaagaag cccgggatct acacccgcgt ggcgagctat     660
gcggcctgga tcgacagcgt cctggcctag taggaattc                           699
```

<210> SEQ ID NO 2
<211> LENGTH: 228
<212> TYPE: PRT
<213> ORGANISM: Homo sapiens

<400> SEQUENCE: 2

```
Ile Leu Gly Gly Arg Glu Ala Glu Ala His Ala Arg Pro Tyr Met Ala
1               5                   10                  15
```

```
Ser Val Gln Leu Asn Gly Ala His Leu Cys Gly Val Leu Val Ala
             20                  25                  30
Glu Gln Trp Val Leu Ser Ala Ala His Cys Leu Glu Asp Ala Ala Asp
         35                  40                  45
Gly Lys Val Gln Val Leu Leu Gly Ala His Ser Leu Ser Gln Pro Glu
 50                  55                  60
Pro Ser Lys Arg Leu Tyr Asp Val Leu Arg Ala Val Pro His Pro Asp
 65                  70                  75                  80
Ser Gln Pro Asp Thr Ile Asp His Asp Leu Leu Leu Leu Gln Leu Ser
                 85                  90                  95
Glu Lys Ala Thr Leu Gly Pro Ala Val Arg Pro Leu Pro Trp Gln Arg
            100                 105                 110
Val Asp Arg Asp Val Ala Pro Gly Thr Leu Cys Asp Val Ala Gly Trp
        115                 120                 125
Gly Ile Val Asn His Ala Gly Arg Arg Pro Asp Ser Leu Gln His Val
130                 135                 140
Leu Leu Pro Val Leu Asp Arg Ala Thr Cys Asp Arg Arg Thr His His
145                 150                 155                 160
Asp Gly Ala Ile Thr Glu Arg Leu Met Cys Ala Glu Ser Asn Arg Arg
                165                 170                 175
Asp Ser Cys Lys Gly Asp Ser Gly Pro Leu Val Cys Gly Gly Val
            180                 185                 190
Leu Glu Gly Val Val Thr Ser Gly Ser Arg Val Cys Gly Asn Arg Lys
        195                 200                 205
Lys Pro Gly Ile Tyr Thr Arg Val Ala Ser Tyr Ala Ala Trp Ile Asp
    210                 215                 220
Ser Val Leu Ala
225
```

<210> SEQ ID NO 3
<211> LENGTH: 714
<212> TYPE: DNA
<213> ORGANISM: Sus scrofa

<400> SEQUENCE: 3

```
cggatcctgg gtggccagga ggccaagtcc cacgagagac cctacatggc atcggtgcag      60
gtgaacggca agcacgtgtg cggaggcttc ctggtgtctg agcagtgggt gctgagtgca     120
gcacactgcc tggaggacgt ggccgagggg aagctgcagg ttctcctggg tgcgcactcc     180
ctgtcacagc ccgagccctc gaagcgcctg tacgacgtgc tccgcgccgt gccccaccca     240
gacagccagc ctgacaccat cgaccatgat ctcctcctgc tgaagctctc cgagaaggcc     300
gagctgggcc ctgccgtgca gccccttgcc tggcaacgag aggaccacga ggttccggca     360
ggcacgctct gcgacgtggc cggctgggga gtggtcagtc acactggccg ccggcccgac     420
cgtctgcagc acctgctcct accggtgctg accgcacca cctgcaacct gcacatac     480
cacgatggca ccatcaccga gcgcatgatg tgcgcggaga gcaaccgtcg ggacagctgc     540
aagggcgact ccgaggcccc gctggtgtgc ggggtgtgg ccgagggagt ggttacctca     600
ggctcccgag tctgcggcaa ccgcaagaaa cccggcatct acacgcgctt ggcgagctac     660
gtggcctgga tcgacggagt gatggctgac agcgcagccg cctagtagga attc           714
```

<210> SEQ ID NO 4
<211> LENGTH: 233
<212> TYPE: PRT
<213> ORGANISM: Sus scrofa

<400> SEQUENCE: 4

```
Ile Leu Gly Gly Gln Glu Ala Lys Ser His Glu Arg Pro Tyr Met Ala
1               5                   10                  15

Ser Val Gln Val Asn Gly Lys His Val Cys Gly Gly Phe Leu Val Ser
            20                  25                  30

Glu Gln Trp Val Leu Ser Ala Ala His Cys Leu Glu Asp Val Ala Glu
        35                  40                  45

Gly Lys Leu Gln Val Leu Leu Gly Ala His Ser Leu Ser Gln Pro Glu
    50                  55                  60

Pro Ser Lys Arg Leu Tyr Asp Val Leu Arg Ala Val Pro His Pro Asp
65                  70                  75                  80

Ser Gln Pro Asp Thr Ile Asp His Asp Leu Leu Leu Leu Lys Leu Ser
                85                  90                  95

Glu Lys Ala Glu Leu Gly Pro Ala Val Gln Pro Leu Ala Trp Gln Arg
            100                 105                 110

Glu Asp His Glu Val Pro Ala Gly Thr Leu Cys Asp Val Ala Gly Trp
        115                 120                 125

Gly Val Val Ser His Thr Gly Arg Arg Pro Asp Arg Leu Gln His Leu
    130                 135                 140

Leu Leu Pro Val Leu Asp Arg Thr Thr Cys Asn Leu Arg Thr Tyr His
145                 150                 155                 160

Asp Gly Thr Ile Thr Glu Arg Met Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Ala Glu Gly Val Val Thr Ser Gly Ser Arg Val Cys Gly Asn Arg Lys
        195                 200                 205

Lys Pro Gly Ile Tyr Thr Arg Leu Ala Ser Tyr Val Ala Trp Ile Asp
    210                 215                 220

Gly Val Met Ala Asp Ser Ala Ala Ala
225                 230
```

<210> SEQ ID NO 5
<211> LENGTH: 25
<212> TYPE: DNA
<213> ORGANISM: ARTIFICIAL
<220> FEATURE:
<223> OTHER INFORMATION: PRIMER FOR VK CHAIN OF 166-32

<400> SEQUENCE: 5
tgcggccgct gtaggtgctg tcttt                                       25

<210> SEQ ID NO 6
<211> LENGTH: 23
<212> TYPE: DNA
<213> ORGANISM: ARTIFICIAL
<220> FEATURE:
<223> OTHER INFORMATION: PRIMER FOR VK GENE OF 166-32

<400> SEQUENCE: 6
ggaattcact cgttattctc gga                                         23

<210> SEQ ID NO 7
<211> LENGTH: 17
<212> TYPE: DNA
<213> ORGANISM: ARTIFICIAL
<220> FEATURE:
<223> OTHER INFORMATION: ANNEALED ADAPTOR FOR CLONING VK GENE OF 166-32

<400> SEQUENCE: 7

```
tccgagaata acgagtg                                              17

<210> SEQ ID NO 8
<211> LENGTH: 29
<212> TYPE: DNA
<213> ORGANISM: ARTIFICIAL
<220> FEATURE:
<223> OTHER INFORMATION: PRIMER OF VH GENE OF 166-32

<400> SEQUENCE: 8
cattgaaagc tttggggtag aagttgttc                                 29

<210> SEQ ID NO 9
<211> LENGTH: 27
<212> TYPE: DNA
<213> ORGANISM: ARTIFICIAL
<220> FEATURE:
<223> OTHER INFORMATION: PRIMER FOR THE VH GENE OF 166-32

<400> SEQUENCE: 9
cgcggccgca gctgctcaga gtgtaga                                   27

<210> SEQ ID NO 10
<211> LENGTH: 28
<212> TYPE: DNA
<213> ORGANISM: ARTIFICIAL
<220> FEATURE:
<223> OTHER INFORMATION: PRIMER FOR CLONING THE VH GENE OF 166-32

<400> SEQUENCE: 10
cggtaagctt cactggctca gggaaata                                  28

<210> SEQ ID NO 11
<211> LENGTH: 37
<212> TYPE: DNA
<213> ORGANISM: ARTIFICIAL
<220> FEATURE:
<223> OTHER INFORMATION: PRIMER FOR THE FD REGION OF 166-32

<400> SEQUENCE: 11
aagaagcttg ccgccaccat ggattggctg tggaact                        37

<210> SEQ ID NO 12
<211> LENGTH: 31
<212> TYPE: DNA
<213> ORGANISM: ARTIFICIAL
<220> FEATURE:
<223> OTHER INFORMATION: PRIMER FOR THE FD REGION OF 166-32

<400> SEQUENCE: 12
cgggatcctc aaactttctt gtccaccttg g                              31

<210> SEQ ID NO 13
<211> LENGTH: 36
<212> TYPE: DNA
<213> ORGANISM: ARTIFICIAL
<220> FEATURE:
<223> OTHER INFORMATION: PRIMER FOR THE FD REGION OF 166-32

<400> SEQUENCE: 13
aagaaagctt gccgccacca tgttctcact agctct                         36

<210> SEQ ID NO 14
<211> LENGTH: 26
<212> TYPE: DNA
<213> ORGANISM: ARTIFICIAL
```

```
<220> FEATURE:
<223> OTHER INFORMATION: PRIMER FOR THE FD REGION OF 166-32

<400> SEQUENCE: 14
cgggatcctt ctccctctaa cactct                                              26

<210> SEQ ID NO 15
<211> LENGTH: 9
<212> TYPE: PRT
<213> ORGANISM: ARTIFICIAL
<220> FEATURE:
<223> OTHER INFORMATION: ADDITIONAL AMINO ACIDS ADDED TO FD TO OBTAIN
      FAB OF 166-32

<400> SEQUENCE: 15

Glu Pro Lys Ser Cys Asp Lys Thr His
1               5
```

NUCLEIC ACIDS ENCODING ANTIBODIES THAT BIND FACTOR D

CROSS REFERENCE TO RELATED APPLICATIONS

This application is a continuation of U.S. application Ser. No. 13/351,845, filed Jan. 17, 2012, now U.S. Pat. No. 8,236,317, which is a continuation of U.S. application Ser. No. 13/081,203, filed Apr. 6, 2011, now U.S. Pat. No. 8,124,090, which is a continuation of U.S. application Ser. No. 11/478,088, filed Jun. 29, 2006, now U.S. Pat. No. 7,943,135, which is a division of U.S. application Ser. No. 11/139,447, filed May 27, 2005, now U.S. Pat. No. 7,112,327, which is a division of U.S. application Ser. No. 09/821,255, filed Mar. 29, 2001, now U.S. Pat. No. 6,956,107, which is a continuation-in-part of U.S. application Ser. No. 09/253,689, filed Feb. 20, 1999, now abandoned, which claims the benefit of U.S. Provisional Application No. 60/075,328, filed Feb. 20, 1998, the disclosure of each of which is incorporated herein by its entirety.

FIELD OF THE INVENTION

This invention relates to inhibitors specific to factor D and the use of such inhibitors in inhibiting complement system activation and inhibiting alternative pathway complement activation.

BACKGROUND OF THE INVENTION

The complement system plays a central role in the clearance of immune complexes and the immune response to infectious agents, foreign antigens, virus-infected cells and tumor cells. However, complement is also involved in pathological inflammation and in autoimmune diseases. Therefore, inhibition of excessive or uncontrolled activation of the complement cascade could provide clinical benefit to patients with such diseases and conditions.

The complement system encompasses two distinct activation pathways, designated the classical and the alternative pathways (V. M. Holers, In *Clinical Immunology: Principles and Practice*, ed. R. R. Rich, Mosby Press; 1996, 363-391). The classical pathway is a calcium/magnesium-dependent cascade which is normally activated by the formation of antigen-antibody complexes. The alternative pathway is magnesium-dependent cascade which is activated by deposition and activation of C3 on certain susceptible surfaces (e.g. cell wall polysaccharides of yeast and bacteria, and certain biopolymer materials). Activation of the complement pathway generates biologically active fragments of complement proteins, e.g. C3a, C4a and C5a anaphylatoxins and C5b-9 membrane attack complexes (MAC), which mediate inflammatory activities involving leukocyte chemotaxis, activation of macrophages, neutrophils, platelets, mast cells and endothelial cells, vascular permeability, cytolysis, and tissue injury.

Factor D is a highly specific serine protease essential for activation of the alternative complement pathway. It cleaves factor B bound to C3b, generating the C3b/Bb enzyme which is the active component of the alternative pathway C3/C5 convertases. Factor D may be a suitable target for inhibition, since its plasma concentration in humans is very low (1.8 µg/ml), and it has been shown to be the limiting enzyme for activation of the alternative complement pathway (P. H. Lesavre and H. J. Mailer-Eberhard. *J. Exp. Med.*, 1978; 148: 1498-1510; J. E. Volanakis et al., *New Eng. J. Med.*, 1985; 312: 395-401).

The down-regulation of complement activation has been demonstrated to be effective in treating several disease indications in animal models and in ex vivo studies, e.g. systemic lupus erythematosus and glomerulonephritis (Y. Wang et al., *Proc. Natl. Acad. Sci.;* 1996, 93: 8563-8568), rheumatoid arthritis (Y. Wang et al., *Proc. Natl. Acad. Sci.,* 1995; 92: 8955-8959), cardiopulmonary bypass and hemodialysis (C. S. Rinder, *J. Clin. Invest.,* 1995; 96: 1564-1572), hypercute rejection in organ transplantation (T. J. Kroshus et al., *Transplantation,* 1995; 60: 1194-1202), myocardial infarction (J. W. Homeister et al., *J. Immunol.,* 1993; 150: 1055-1064; H. F. Weisman et al., *Science,* 1990; 249: 146-151), reperfusion injury (E. A. Amsterdam et al., *Am. J. Physiol.,* 1995; 268: H448-H457), and adult respiratory distress syndrome (R. Rabinovici et al., *J. Immunol.,* 1992; 149: 1744-1750). In addition, other inflammatory conditions and autoimmune/immune complex diseases are also closely associated with complement activation (V. M. Holers, ibid, B. P. Morgan. *Eur. J. Clin. Invest,* 1994:24:219-228), including thermal injury, severe asthma, anaphylactic shock, bowel inflammation, urticaria, angioedema, vasculitis, multiple sclerosis, myasthenia gravis, psoriasis, dermatomyositis, membranoproliferative glomerulonephritis, and Sjögren's syndrome.

SUMMARY OF THE INVENTION

The invention includes factor D inhibitors, which bind to factor D and block the functional activity of factor D complement activation, including in alternative pathway complement activation. The inhibitors include antibody molecules, as well as homologues, analogues and modified or derived forms thereof, including immunoglobulin fragments like Fab, F(ab')₂ and Fv. Small molecules including peptides, oligonucleotides, peptidomimetics and organic compounds which bind to factor D and block its functional activity are also included. The invention also includes an inhibitor of complement activation which specifically binds factor D which at a molar ratio of about 1.5:1 (inhibitor:factor D) can substantially inhibit complement activation.

A monoclonal antibody which bound to factor D and blocked its ability to activate complement was generated and designated 166-32. The hybridoma producing this antibody was deposited at the American Type Culture Collection, 10801 University Blvd., Manassas, Va. 20110-2209, under Accession Number HB-12476, on Feb. 24, 1998.

DESCRIPTION OF THE DRAWINGS

FIG. 26 shows the complete, selective inhibition of the alternative complement activity in plasma obtained from the extracorporeal circuits treated with MAb 166-32 as compared to the negative control MAb G3-519. MAb 166-32 did not inhibit the classical complement activity of the human plasma in the circuits. The number of paired circuits is 5. Mean±S.E.M.; P=0.002 (paired T test) between MAb 166-32 and MAb G3-519 circuits.

FIG. 27 shows that MAb 166-32 (closed squares) inhibits the production of Bb in the extracorporeal circuits as compared to the negative control MAb G3-519 (open squares). The number of paired circuits is 5. Mean±S.E.M.; P=0.001 (*) and P=0.0001 (**) by two-factor ANOVA.

FIG. 28 shows that MAb 166-32 (closed squares) inhibits the production of C4d in the extracorporeal circuits as compared to the negative control MAb G3-519 (open squares). The number of paired circuits is 5. Mean±S.E.M. No significant difference between the two groups by two-factor ANOVA.

FIG. 29 shows that MAb 166-32 (closed squares) inhibits the production of C3a in the extracorporeal circuits as compared to the negative control MAb G3-519 (open squares). The number of paired circuits is 5. Mean±S.E.M.; P=0.0003 (*) and P=0.0001 (**) by two-factor ANOVA.

FIG. 30 shows that MAb 166-32 (closed squares) inhibits the production of sC5b-9 in the extracorporeal circuits as compared to the negative control MAb G3-519 (open squares). The number of paired circuits is 5. Mean±S.E.M.; P=0.01(*) and P=0.0001(**) by two-factor ANOVA.

FIG. 31 shows that MAb 166-32 (closed squares) inhibits the production of C5a in the extracorporeal circuits as compared to the negative control MAb G3-519 (open squares). The number of paired circuits is 5. Mean±S.E.M.; P=0.003 (*), P=0.002 () and P=0.0001 (*) by two-factor ANOVA.

FIG. 32 shows that MAb 166-32 (closed squares) inhibits the expression of CD11b in the extracorporeal circuits as compared to the negative control MAb G3-519 (open squares). The level of CD11b expression is expressed as fluorescent intensity normalized with reference to the value at time 0 (100%). The number of paired circuits is 5. Mean±S.E.M.; P=0.02 (*), P=0.01 (), P=0.007 (*), P=0.003 (*) and P=0.0001 (**) by two-factor ANOVA.

FIG. 33 shows that MAb 166-32 (closed squares) inhibits the production of myeloperoxidase in the extracorporeal circuits as compared to the negative control MAb G3-519 (open squares). The number of paired circuits is 5. Mean±S.E.M.; P=0.004 (*) and P=0.0002 (**) by two-factor ANOVA.

FIG. 34 shows that MAb 166-32 (closed squares) inhibits the production of elastase-$\alpha$1-antitrypsin in the extracorporeal circuits as compared to the negative control MAb G3-519 (open squares). The number of paired circuits is 5. Mean±S.E.M.; P=0.0007 (*) and P=0.0001 (**) by two-factor ANOVA.

FIG. 35 shows that MAb 166-32 (closed squares) inhibits the expression of CD62P on platelets in the extracorporeal circuits as compared to the negative control MAb G3-519 (open squares). The level of CD62P expression is expressed as fluorescence intensity normalized with reference to the value at time 0 (100%). The number of paired circuits is 5. Mean±S.E.M.; P=0.0001 (*) by two-factor ANOVA.

FIG. 36 shows that MAb 166-32 (closed squares) reduces the percentage of platelets expressing CD62P as compared to the negative control MAb G3-519 (open squares). The number of paired circuits is 5. Mean±S.E.M.; P=0.05 (*), P=0.005 () and P=0.0001 (*) by two-factor ANOVA.

FIG. 37 shows that MAb 166-32 (closed squares) inhibits the production of platelet thrombospondin in the extracorporeal circuits as compared to the negative control MAb G3-519 (open squares). The number of paired circuits is 5. Mean±S.E.M.; P=0.016 (*), P=0.003 () and P=0.0001 (*) by two-factor ANOVA.

FIG. 38 shows that MAb 166-32 (closed squares) inhibits the production of IL-8 in the extracorporeal circuits as compared to the negative control MAb G3-519 (open squares). The number of paired circuits is 5. Mean±P=0.0001 (*) by two-factor ANOVA.

FIG. 39 shows the pharmacokinetics of Mab 166-32 in a baboon model of cardiopulmonary bypass (CPB).

FIG. 40 shows the inhibition of alternative complement activation by Mab 166-32 in baboon CPB.

FIG. 41 shows the Bb concentration as affected by Mab 166-32.

FIG. 42 shows the C4d concentration as affected by Mab 166-32.

FIG. 43 shows the C3a concentration as affected by Mab 166-32.

FIG. 44 shows CD11b expression on neutrophils as affected by Mab 166-32.

FIG. 45 shows CD11b expression on monocytes as affected by Mab 166-32.

FIG. 46 shows CD62P expression on platelets as affected by Mab 166-32.

FIG. 47 shows plasma IL-6 levels as affected by Mab 166-32.

FIG. 48 shows plasma LDH levels as affected by Mab 166-32.

FIG. 49 shows plasma creatine kinase levels as affected by Mab 166-32.

FIG. 50 shows plasma creatine kinase levels as affected by Mab 166-32.

FIG. 51 shows plasma creatinine levels as affected by Mab 166-32.

FIG. 52 shows dynamic lung compliance of baboons in CPB as affected by Mab 166-32.

DESCRIPTION OF THE SEQUENCE LISTING

Figure 1:
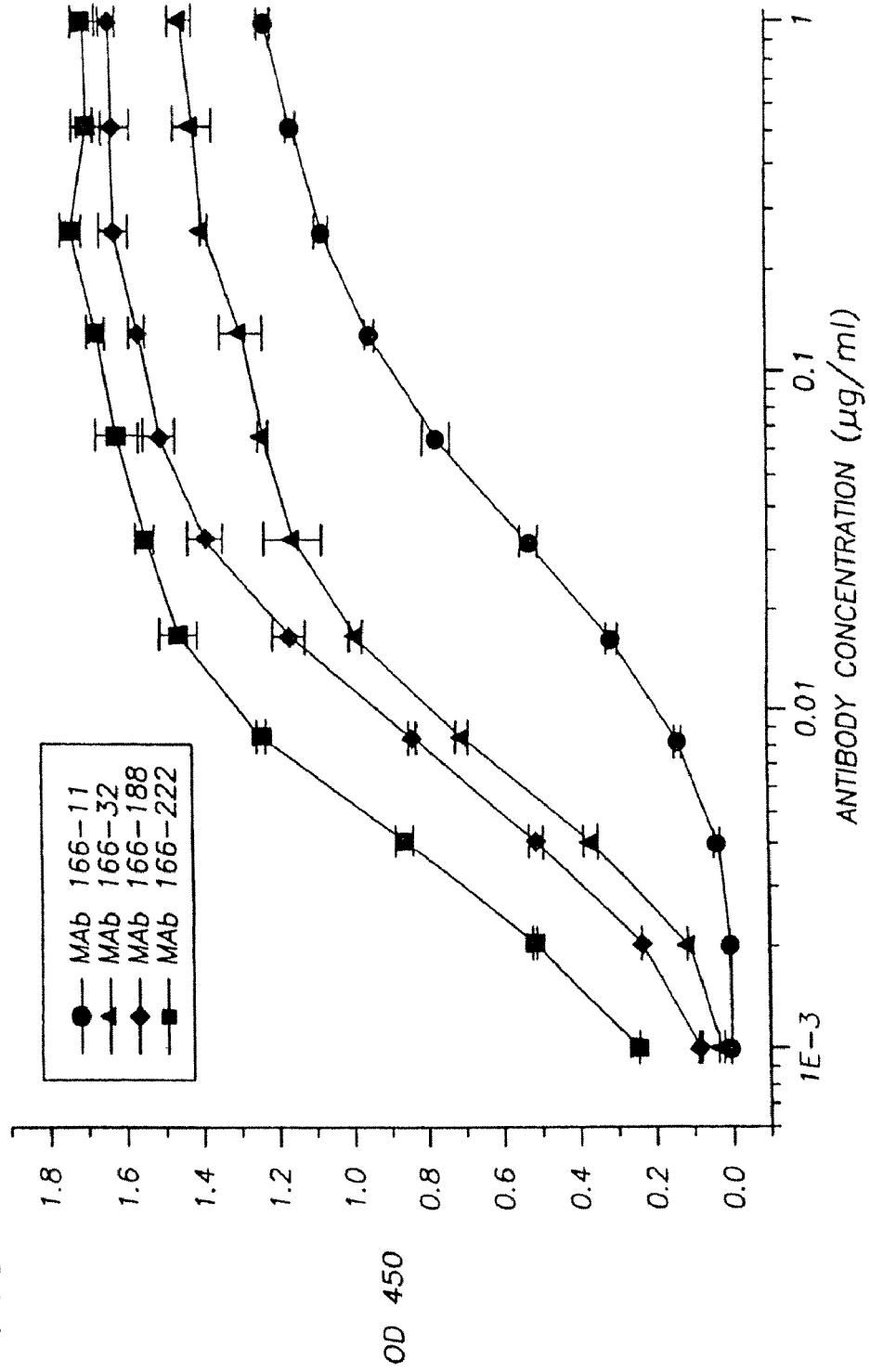
FIG. 1 shows the binding of anti-factor D monoclonal antibodies (MAbs) to purified human factor D in ELISA. The line marked with filled circles represents MAb 166-11. The line marked with filled triangles represents MAb 166-32. The line marked with filled diamonds represents MAb 166-188. The line marked with filled squares represents MAb 166-222. The Y-axis represents the reactivity of the MAbs with factor D expressed as optical density (OD) at 450 nm and the X-axis represents the concentration of the MAbs.

SEQ ID NO:1 shows the nucleotide sequence of human factor D.

SEQ ID NO:2 shows the amino acid sequence of human factor D.

SEQ ID NO:3 shows the nucleotide sequence of pig factor D.

SEQ ID NO:4 shows the amino acid sequence of pig factor D.

SEQ ID NO:5 is the primer used for cloning the $V_K$ gene of MAb 166-32.

SEQ ID NO:6 was used as an anealed adaptor for cloning the $V_K$ gene of MAb 166-32, as described below, and as a primer.

SEQ ID NO:7 was also used as an anealed adaptor for cloning the $V_K$ gene of MAb 166-32, as described below.

SEQ ID NO:8 was used as a 3' primer for cloning the $V_H$ gene of MAb 166-32, as described below.

SEQ ID NO:9 was a primer used for cloning the $V_H$ gene of MAb 166-32.

SEQ ID NO: 10 was used as a primer for cloning the $V_H$ gene of MAb 166-32.

SEQ ID NO: 11 was the 5' primer for the PCR of the Fd gene of MAb 166-32.

SEQ ID NO: 12 was the 3' primer for the PCR of the Fd gene of MAb 166-32. SEQ ID NO: 13 was the 5' primer for the Fd gene PCR of MAb 166-32

SEQ ID NO: 14 was the 3' primer for the Fd gene PCR of MAb 166-32.

SEQ ID NO: 15 is the sequence for additional amino acids added to Fd to obtain recombinant Fab.

Making and Using the Invention

A. Generation of Monoclonal Antibodies (MAbs) to Human Factor D

In one embodiment of the invention, anti-factor D MAbs can be raised by immunizing rodents (e.g. mice, rats, hamsters and guinea pigs) with either native factor D purified from human plasma or urine, or recombinant factor D or its fragments expressed by either eukaryotic or prokaryotic systems. Other animals can be used for immunization, e.g. non-human primates, transgenic mice expressing human immunoglobulins and severe combined immunodeficient (SCID) mice transplanted with human B lymphocytes. Hybridomas can be generated by conventional procedures by fusing B lymphocytes from the immunized animals with myeloma cells (e.g. Sp2/0 and NS0), as described by G. Köhler and C. Milstein (*Nature,* 1975:256:495-497). In addition, anti-factor D antibodies can be generated by screening of recombinant single-chain Fv or Fab libraries from human B lymphocytes in phage-display systems. The specificity of the MAbs to human factor D can be tested by enzyme linked immunosorbent assay (ELISA), Western immunoblotting, or other immunochemical techniques. The inhibitory activity of the antibodies on complement activation can be assessed by hemolytic assays using unsensitized rabbit or guinea pig red blood cells (RBCs) for the alternative pathway, and using sensitized chicken or sheep RBCs for the classical pathway. The hybridomas in the positive wells are cloned by limiting dilution. The antibodies are purified for characterization for specificity to human factor D by the assays described above.

If used in treating inflammatory or autoimmune diseases in humans, the anti-factor D antibodies would preferably be used as chimeric, deimmunized, humanized or human antibodies. Such antibodies can reduce immunogenicity and thus avoid human anti-mouse antibody (HAMA) response. It is preferable that the antibody be IgG4, IgG2, or other genetically mutated IgG or IgM which does not augment antibody-dependent cellular cytotoxicity (S. M. Canfield and S. L. Morrison, *J. Exp. Med.,* 1991:173:1483-1491) and complement mediated cytolysis (Y. Xu et al., *J. Biol. Chem.,* 1994: 269:3468-3474; V. L. Pulito et al., *J. Immunol.,* 1996; 156: 2840-2850).

Chimeric antibodies are produced by recombinant processes well known in the art, and have an animal variable region and a human constant region. Humanized antibodies have a greater degree of human peptide sequences than do chimeric antibodies. In a humanized antibody, only the complementarity determining regions (CDRs) which are responsible for antigen binding and specificity are animal derived and have an amino acid sequence corresponding to the animal antibody, and substantially all of the remaining portions of the molecule (except, in some cases, small portions of the framework regions within the variable region) are human derived and correspond in amino acid sequence to a human antibody. See L. Riechmann et al., *Nature,* 1988; 332: 323-327; G. Winter, U.S. Pat. No. 5,225,539; C. Queen et al., U.S. Pat. No. 5,530,101.

Deimmunized antibodies are antibodies in which the T and B cell epitopes have been eliminated, as described in International Patent Application PCT/GB98/01473. They have no or reduced immunogenicity when applied in vivo.

Human antibodies can be made by several different ways, including by use of human immunoglobulin expression libraries (Stratagene Corp., La Jolla, Calif.) to produce fragments of human antibodies (VH, VL, Fv, Fd, Fab, or F(ab')$_2$, and using these fragments to construct whole human antibodies using techniques similar to those for producing chimeric antibodies. Human antibodies can also be produced in transgenic mice with a human immunoglobulin genome. Such mice are available from Abgenix, Inc., Fremont, Calif., and Medarex, Inc., Annandale, N.J.

One can also create single peptide chain binding molecules in which the heavy and light chain Fv regions are connected. Single chain antibodies ("ScFv") and the method of their construction are described in U.S. Pat. No. 4,946,778. Alternatively, Fab can be constructed and expressed by similar means (M. J. Evans et al. *J. Immunol. Meth.,* 1995; 184: 123-138). All of the wholly and partially human antibodies are less immunogenic than wholly murine MAbs, and the fragments and single chain antibodies are also less immunogenic. All these types of antibodies are therefore less likely to evoke an immune or allergic response. Consequently, they are better suited for in vivo administration in humans than wholly animal antibodies, especially when repeated or long-term administration is necessary. In addition, the smaller size of the antibody fragment may help improve tissue bioavailability, which may be critical for better dose accumulation in acute disease indications.

Based on the molecular structures of the variable regions of the anti-factor D antibodies, one could use molecular modeling and rational molecular design to generate and screen small molecules which mimic the molecular structures of the binding region of the antibodies and inhibit the activities of factor D. These small molecules can be peptides, peptidomimetics, oligonucleotides, or organic compounds. The mimicking molecules can be used as inhibitors of complement activation in inflammatory indications and autoimmune diseases. Alternatively, one could use large-scale screening procedures commonly used in the field to isolate suitable small molecules form libraries of combinatorial compounds.

In one preferred embodiment of the invention, a chimeric Fab, having animal (mouse) variable regions and human constant regions is used therapeutically. The Fab is preferred because:

it is smaller than a whole immunoglobulin and may provide better tissue permeation;

as monovalent molecule, there is less chance of immunocomplexes and aggregates forming; and it can be produced in a microbial system, which can more easily be scaled-up than a mammalian system.

B. Applications of the Anti-Factor D Molecules

The anti-factor D binding molecules, antibodies, and fragments of this invention, can be administered to patients in an appropriate pharmaceutical formulation by a variety of routes, including, but not limited, intravenous infusion, intravenous bolus injection, and intraperitoneal, intradermal, intramuscular, subcutaneous, intranasal, intratracheal, intraspinal, intracranial, and oral routes. Such administration enables them to bind to endogenous factor D and thus inhibit the generation of C3b, C3a and C5a anaphylatoxins, and C5b-9.

The estimated preferred dosage of such antibodies and molecules is between 10 and 500 µg/ml of serum. The actual dosage can be determined in clinical trials following the conventional methodology for determining optimal dosages, i.e., administering various dosages and determining which is most effective.

The anti-factor D molecules can function to inhibit in vivo complement activation and/or the alternative complement pathway and inflammatory manifestations that accompany it, such as recruitment and activation of macrophages, neutrophils, platelets, and mast cells, edema, and tissue damage. These inhibitors can be used for treatment of diseases or conditions that are mediated by excessive or uncontrolled activation of the complement system. These include, but are not limited to: (1) tissue damage due to ischemia-reperfusion following acute myocardial infarction, aneurysm, stroke, hemorrhagic shock, crush injury, multiple organ failure, hypovolemic shock and intestinal ischemia; (2) inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis and pancreatitis; (3) transplant rejection, e.g., hyperacute xenograft rejection; and (4) adverse drug reactions, e.g., drug allergy, IL-2 induced vascular leakage syndrome and radiographic contrast media allergy. Autoimmune disorders including, but not limited to, systemic lupus erythematosus, myasthenia gravis, rheumatoid arthritis, Alzheimer's disease and multiple sclerosis, may also be treated with the inhibitors of the invention.

The anti-factor D molecules can also be used diagnostically to ascertain the presence of, or to quantify, factor D in a tissue specimen or a body fluid sample, such as serum, plasma, urine or spinal fluid. In this application, well-known assay formats can be used, such as immunohistochemistry or ELISA, respectively. Such diagnostic tests could be useful in determining whether certain individuals are either deficient in or overproduce factor D.

C. Animal Models of the Therapeutic Efficacy of Factor D Inhibitors

The therapeutic activity of factor D inhibitors in various disease indications described above can be confirmed by using available animal models for various inflammatory and autoimmune manifestations. The in vitro tests described below in the examples are adequate to establish their efficacy.

Animal models relevant to various complement-related clinical diseases in humans can also be used to confirm the in vivo efficacy of factor D inhibitors. These include, but not limited to: myocardial ischemia/reperfusion injury (H. F. Weisman et al., *Science*, 1990; 249: 146-151); myocardial infarction (J. W. Homeister et al., *J. Immunol.* 1993; 150: 1055-1064), systemic lupus erythematosus and glomerulonephritis (S. K. Datta. *Meth. Enzymol.*, 1988; 162: 385-442; D. J. Salvant and A. V. Cybulsky, *Meth. Enzymol.*, 1988; 162: 421-461), rheumatoid arthritis (Y. Wang et al., *Proc. Natl. Acad. Sci.*, 1995; 92: 8955-8959), adult respiratory distress syndrome (R. Rabinovici et al., *J. Immunol.*, 1992; 149: 1744-1750), hyperacute rejection in organ transplantation (T. J. Kroshus et al., *Transplantation*, 1995; 60: 1194-1202), burn injury (M. S. Mulligan et al., *J. Immunol.*, 1992; 148: 1479-1485), cardiopulmonary bypass (C. S. Rinder et al., *J. Clin. Invest.*, 1995; 96: 1564-1572).

Exemplification of how to make and use the invention, and verification of its utility, appear below.

Example 1

Generation of Anti-Factor D MAbs

Male A/J mice (Harlan, Houston, Tex.), 8-12 weeks old, were injected subcutaneously with 25 µg of factor D purified from human serum (Advanced Research Technologies, San Diego, Calif.) in complete Freund's adjuvant (Difco Laboratories, Detroit, Mich.) in 200 µl of phosphate-buffered saline (PBS) pH7.4. The factor D preparation were tested to be >95% pure by sodium dodecylsulphate (SDS)-polyacrylamide gel electrophoresis (PAGE). The factor D was tested and found to be biologically active in hemolysis as described below. At two-week intervals the mice were twice injected subcutaneously with 25 µg of human factor D in incomplete Freund's adjuvant. Then two weeks later and three days prior to sacrifice, the mice were again injected intraperitoneally with 25 µg of the same antigen in PBS. For each fusion, single cell suspensions were prepared from the spleen of an immunized mouse and used for fusion with Sp2/0 myeloma cells. $5 \times 10^8$ of the Sp2/0 and $5 \times 10^8$ spleen cells were fused in a medium containing 50% polyethylene glycol (M.W. 1450) (Kodak, Rochester, N.Y.) and 5% dimethylsulfoxide (Sigma Chemical Co., St. Louis, Mo.). The cells were then adjusted to a concentration of $1.5 \times 10^5$ spleen cells per 200 µl of the suspension in Iscove medium (Gibco, Grand Island, N.Y.), supplemented with 10% fetal bovine serum, 100 units/ml of penicillin, 100 µg/ml of streptomycin, 0.1 mM hypoxanthine, 0.4 µM aminopterin, and 16 µM thymidine. Two hundred microliters of the cell suspension were added to each well of about twenty 96-well microculture plates. After about ten days culture supernatants were withdrawn for screening for reactivity with purified factor D in ELISA.

Wells of Immulon 2 (Dynatech Laboratories, Chantilly, Va.) microtest plates were coated by adding 50 µl of purified human factor at 50 µg/ml overnight at room temperature. The low concentration of factor D for coating enabled the selection of high-affinity antibodies. After the coating solution was removed by flicking of the plate, 200 µl of BLOTTO (non-fat dry milk) in PBS was added to each well for one hour to block the non-specific sites. An hour later, the wells were then washed with a buffer PBST (PBS containing 0.05% Tween 20). Fifty microliters of culture supernatants from each fusion well were collected and mixed with 50 µl of BLOTTO and then added to the individual wells of the microtest plates. After one hour of incubation, the wells were washed with PBST. The bound murine antibodies were then detected by reaction with horseradish peroxidase (HRP) conjugated goat anti-mouse IgG (Fc specific) (Jackson ImmunoResearch Laboratories, West Grove, Pa.) and diluted at 1:2,000 in BLOTTO. Peroxidase substrate solution containing 0.1% 3,3,5,5 tetramethyl benzidine (Sigma, St. Louis, Mo.) and 0.0003% hydrogen peroxide (sigma) was added to the wells for color development for 30 minutes. The reaction was terminated by addition of 50 µl of 2M $H_2SO_4$ per well. The OD at 450 nm of the reaction mixture was read with a BioTek ELISA Reader (BioTek Instruments, Winooski, Vt.).

The culture supernatants from the positive wells were then tested by two assays: i) inhibition of alternative pathway hemolysis of unsensitized rabbit RBCs by pre-titered human serum by the method described below; and ii) inhibition of formation of C3a by zymosan treated with human serum as described below. The cells in those positive wells were cloned by limiting dilution. The MAbs were tested again for reactivity with factor D in the ELISA. The selected hybridomas were grown in spinner flasks and the spent culture supernatant collected for antibody purification by protein A affinity chromatography. Four MAbs were tested to be strongly reactive with human factor D in ELISA. These MAbs are designated 166-11, 166-32, 166-188, and 166-222 (FIG. 1). Among them, MAb 166-32 (IgG1) strongly inhibited the alternative pathway hemolysis of unsensitized rabbit RBCs as described below.

Example 2

Determination the Kinetic Constants of the Anti-Factor D MAbs by Surface Plasmon Resonance Method The kinetic constants for the binding of MAbs 166-11, 166-32, 166-188, and 166-22 to human factor D were determined by surface plasmon resonance-based measurements using the BIAcore instrument (Pharmacia Biosensor AB, Uppsala, Sweden). All the binding measurements were performed in HEPES-buffered saline (HBS) (10 mM HEPES, pH 7.4, 150 mM NaCl, 3.4 mM EDTA, 0.005% Surfactant P20) at 25° C. To measure the binding rate constants of factor D to the MAbs, a rabbit anti-mouse IgG (H+L) was immobilized onto a CM5 sensorchip by amine coupling using N-hydroxysuccinimide and N-ethyl-N'-(3-diethylaminopropyl) carbodimide. Each individual MAb was then captured onto the coated sensorchip before the injection of factor D at different concentrations. To measure the association rate constants ($k_{assoc}$), five dilutions of factor D (2.5 nM, 5 nM, 10 nM, 15 nM and 20 nM) were made based on the concentration indicated by the manufacturer, and were injected to the flowcell at the flow rate of 5 µl/min. To measure the dissociation rate constants ($k_{assoc}$), 100 nM factor D was injected into the flowcell at the flow rate of 5 µl/min. The data, in the form of sensorgrams, was analyzed using the data-fitting programs implemented in the BIAcore system. Since MAb 166-32 has a very fast $k_{assoc}$ which is beyond the reliability limit of the assay format due to the limitation of the mass transport effect, an additional binding format was also used to measure its kinetic rate constants. Factor D was immobilized onto the sensorchip by amine coupling as described above while MAb 166-32 of different dilutions (5 nM, 10 nM, 15 nM, 20 nM and 25 nM for the measurement of $k_{assoc}$ and 200 nM for the measurement of $k_{dissoc}$ flowed to the sensorchip at the flow rate of 5 µl/min. The data, in the form of sensorgrams, was analyzed as described above. The kinetic constants of factor D binding to the MAbs on BIAcore is shown in Table 1 below. MAbs 166-32 and 166-222 have very high affinity to factor D, with equilibrium dissociation constant ($K_D$) less than 0.1 nM.

TABLE 1

Kinetic Constants of Factor D Binding to MAbs on BIAcore

| MAbs | $k_{assoc}(\times 10^5 \, M^{-1}s^{-1})$ | $k_{dissoc}(\times 10^{-4}s^{-1})$ | $K_D(\times 10^{-10}M)^c$ |
|---|---|---|---|
| 166-32[a] | >10 | 1.1 | <11 |
| 166-32[b] | 4.6 | 0.76 | 1.6 |
| 166-188[a] | 8.75 | 2.1 | 2.4 |
| 166-11[a] | 8.0 | 1.0 | 1.24 |
| 166-222[a] | >10 | 0.8 | <1 |

[a]Factor D was used as the analyte which flowed onto the sensorchip coated with anti-factor D MAb captured by rabbit anti-mouse IgG during the determination.
[b]MAb 166-32 was used as the analyte and factor D was crosslinked to the sensorchip by the amine-coupling method.
[c]$K_D$, equilibrium dissociation constant, = $k_{dissoc}/k_{assoc}$ Example 3

Inhibition of Complement-Activated Hemolysis

To study the functional activity of the anti-factor D MAbs in inhibiting complement activation in vitro, two hemolytic assays were used.

For the alternative pathway, unsensitized rabbit RBCs were washed three times with gelatin/veronal-buffered saline (GVB/Mg-EGTA) containing 2 mM $MgCl_2$ and 1.6 mM EGTA. EGTA at a concentration of 10 mM was used to inhibit the classical pathway (K. Whaley et al., in A. W. Dodds (Ed.), Complement: A Practical Approach. Oxford University Press, Oxford, 1997, pp. 19-47). The washed cells were resuspended in the same buffer at $1.7 \times 10^8$ cells/ml. In each well of a round-bottom 96-well microtest plate, 50 µl of normal human serum (20%) was mixed with 50 µl of GVB/Mg-EGTA or serially diluted test MAb then 30 µl of the washed rabbit RBCs suspension were added to the wells containing the mixtures. Fifty microliters of normal human serum (20%) was mixed with 80 µl of GVB/Mg-EGTA to give the serum color background. For negative control, an isotype-matched anti-HIV-1 gp120 MAb, G3-519, was used. The final mixture was incubated at 37° C. for 30 minutes. The plate was then shaken on a micro-test plate shaker for 15 seconds. The plate was then centrifuged at 300×g for 3 minutes. Supernatants (80 µl) were collected and transferred to wells on a flat-bottom 96-well microtest plates for measurement of OD at 405 nm. The percent inhibition of hemolysis is defined as 100×[(OD without MAb−OD serum color background)−(OD with MAb−OD serum color background)]/(OD without MAb−OD serum color background).

Figure 2:
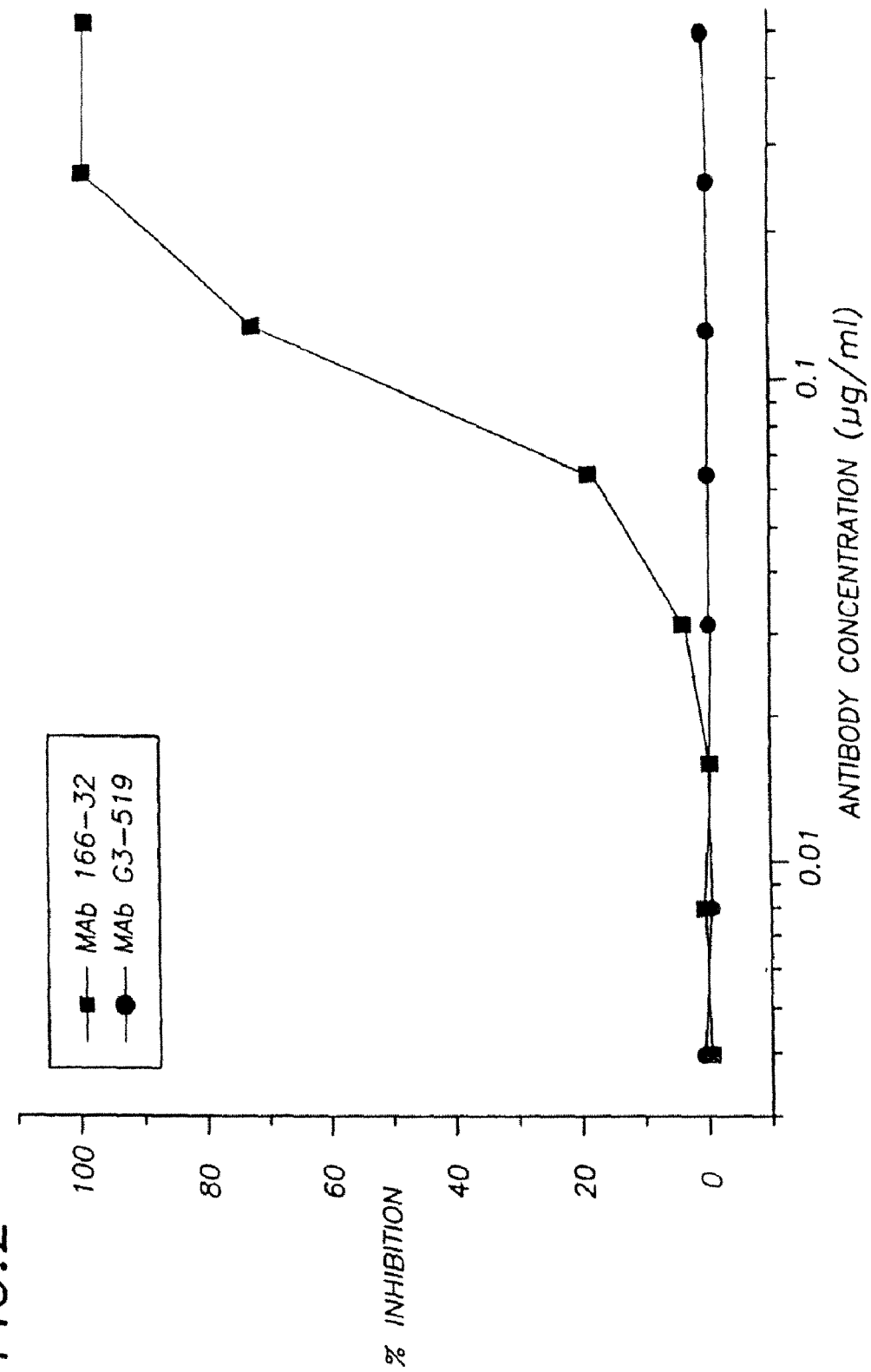
FIG. 2 shows the inhibition of alternative pathway (AP) hemolysis of unsensitized rabbit red blood cells (RBCs) by MAb 166-32 in the presence of 10% human serum. The line marked with filled squares represents MAb 166-32. The line marked with filled circles represents the irrelevant isotype-matched control MAb G3-519, which is specific to HIV envelope glycoprotein gp120. The Y-axis represents the % hemolysis inhibition, as further described in the text. The X-axis represents the concentration of the MAbs.

FIG. 2 shows the data that MAb 166-32 strongly inhibits in a dose-dependent manner the alternative pathway hemolysis of unsensitized rabbit RBCs in the presence of 10% human serum, whereas the irrelevant isotype-matched control MAb G3-519 does not. MAb G3-519 is specific to HIV envelope glycoprotein gp120.

Figure 3:
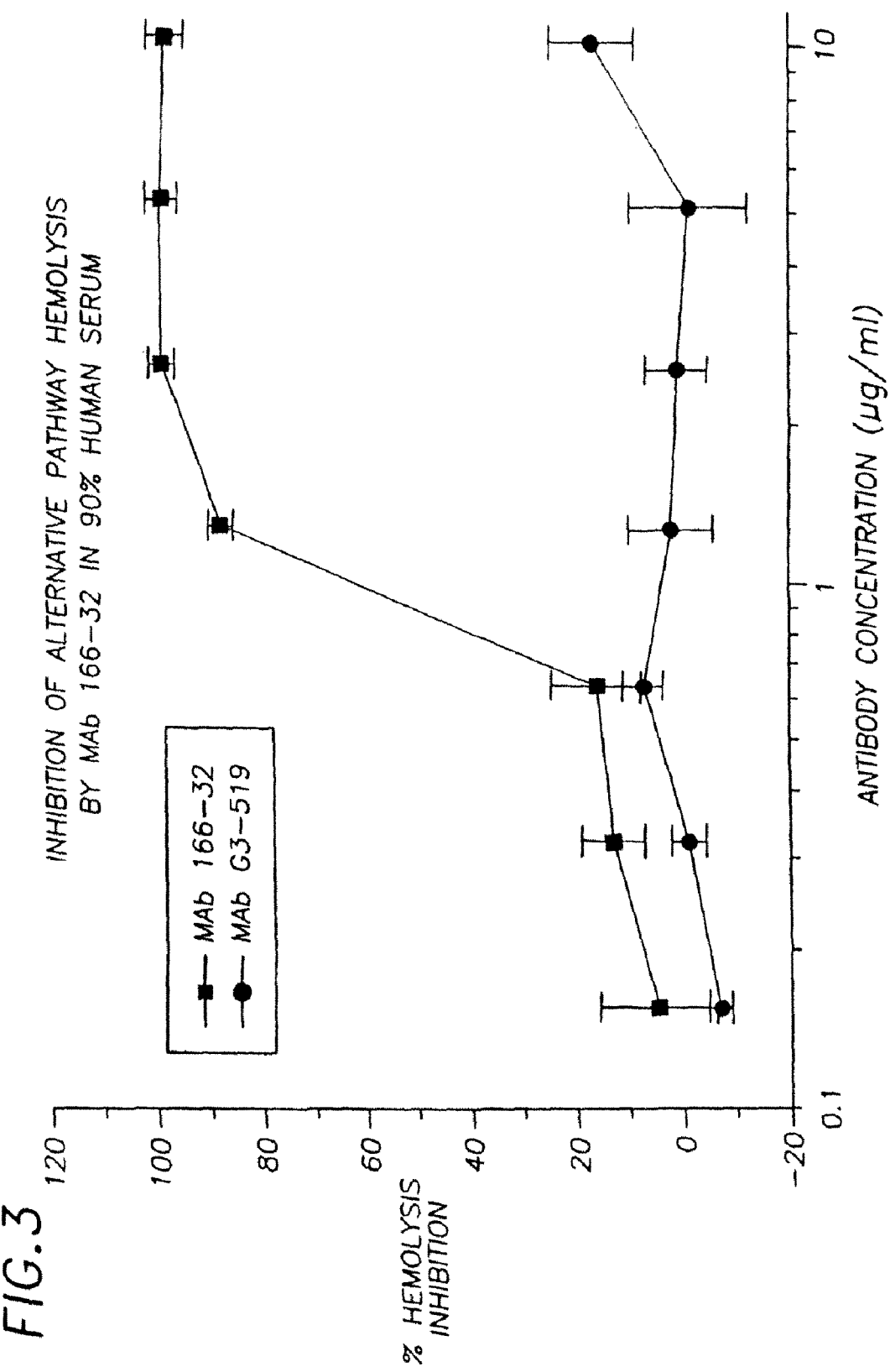
FIG. 3 shows the inhibition of alternative pathway (AP) hemolysis of unsensitized rabbit red blood cells (RBCs) by MAb 166-32 in the presence of 90% human serum. The line marked with filled squares represents MAb 166-32. The line marked with filled circles represents the irrelevant isotype-matched control MAb G3-519, which is specific to HIV envelope glycoprotein gp120. The Y-axis represents the % hemolysis inhibition, as further described in the text. The X-axis represents the concentration of the MAbs.

In assays to test the inhibitory activity of MAb166-32 in 90% human serum, frozen human serum was thawed and pre-treated with EGTA at a final concentration of 10 mM. Ten microliters of serially diluted MAb 166-32 or G3-519 were added to 90 μl of EGTA-treated human serum in duplicate wells of a 96-well microtest plate for 15 minutes at room temperature. Thirty microliters of the washed rabbit RBC's were added to each well. The plate was incubated at 37° C. for 30 minutes. The plate was shaken on a plate-shaker for 15 seconds and then centrifuged at 300×g for 3 minutes. Supernatants (80 μl) were collected and transferred to wells on a flat-bottom 96-well microtest plate for measurement of OD at 405 nm. Each plate contained two wells containing 100 μl of 90% human serum and 30 μl of the buffer as serum color background and also two wells containing the RBCs lysed with 100 μl of 90% human serum, in the absence of monoclonal antibody, to represent total lysis. FIG. 3 shows the data that MAb 166-32 strongly inhibits in a dose-dependent manner the alternative pathway hemolysis of unsensitized rabbit RBCs even in the presence of 90% human serum.

For the classical pathway, chicken RBCs ($5 \times 10^7$ cells/ml) in gelatin/veronal-buffered saline (GVB$^{++}$) containing 0.5 mM MgCl$_2$ and 0.15 mM CaCl$_2$ were sensitized with purified rabbit anti-chicken RBC immunoglobulins at 8 μg/ml (Inter-Cell Technologies, Hopewell, N.J.) for 15 minutes at 4° C. The cells were then washed with GVB$^{++}$. The final human serum concentration used was 2%.

Figure 4:
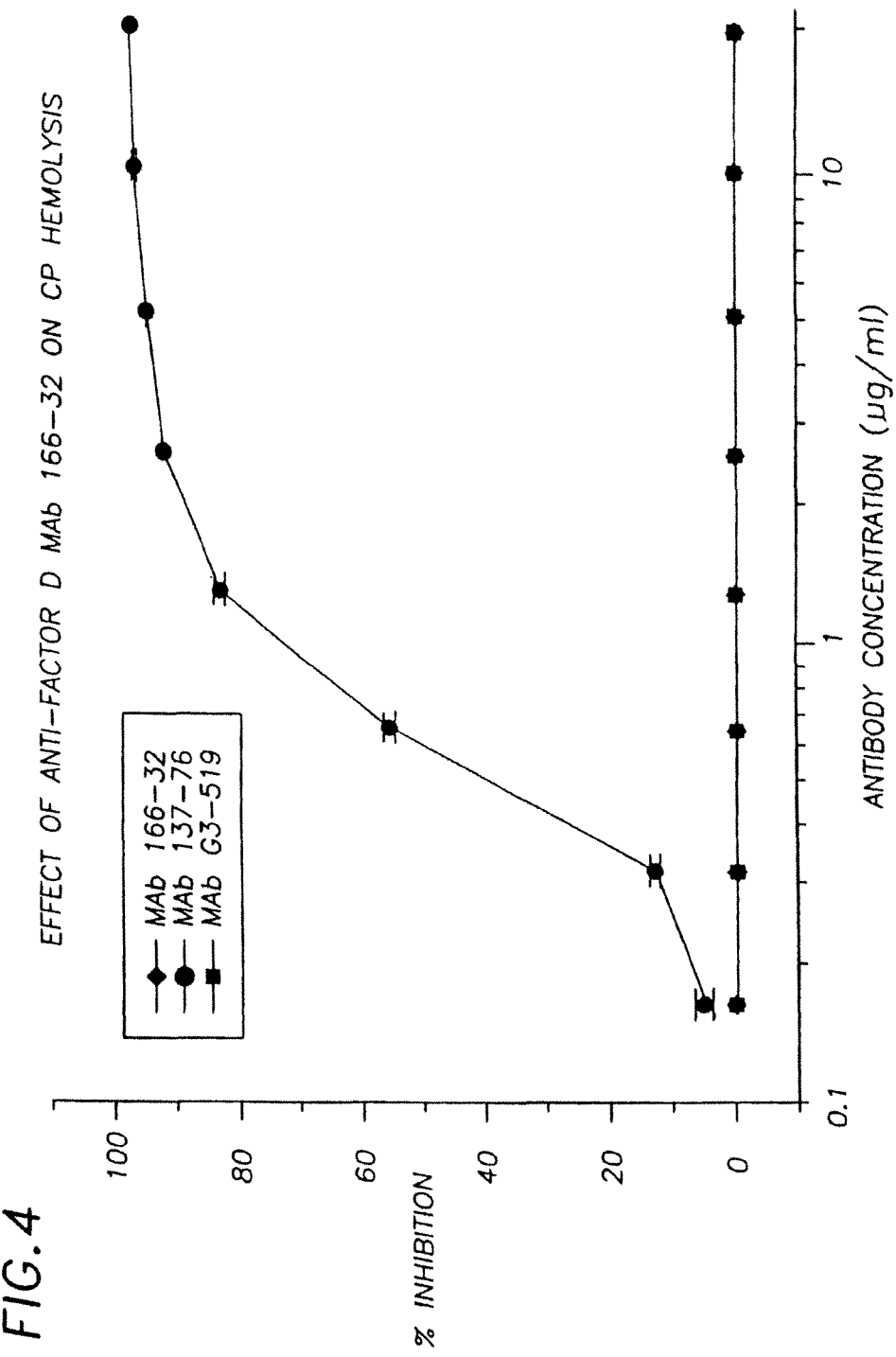
FIG. 4 shows that MAb 166-32 does not inhibit classical pathway (CP) hemolysis of sensitized chicken RBCs, whereas the positive control anti-human C5 MAb 137-76 does. The line marked with filled circles represents MAb 137-76. The line marked with filled diamonds and with filled squares represents MAb 166-32 and the negative control MAb G3-519, respectively. The Y-axis represents the % hemolysis inhibition. The X-axis represents the concentration of the MAbs.

FIG. 4 shows the data that MAb 166-32 and the irrelevant control G3-519 do not inhibit the classical pathway hemolysis of sensitized chicken RBCs, whereas the positive control anti-human C5 MAb 137-76 does. The data from FIGS. 2, 3 and 4 indicate that MAb 166-32 is specific to the inhibition of the alternative pathway of complement activation.

Example 4

Specificity of MAb 166-32 to Factor D

Two hemolytic assays, as described below, were used to demonstrate the specificity of MAb166-32 to human factor D.

Figure 5:
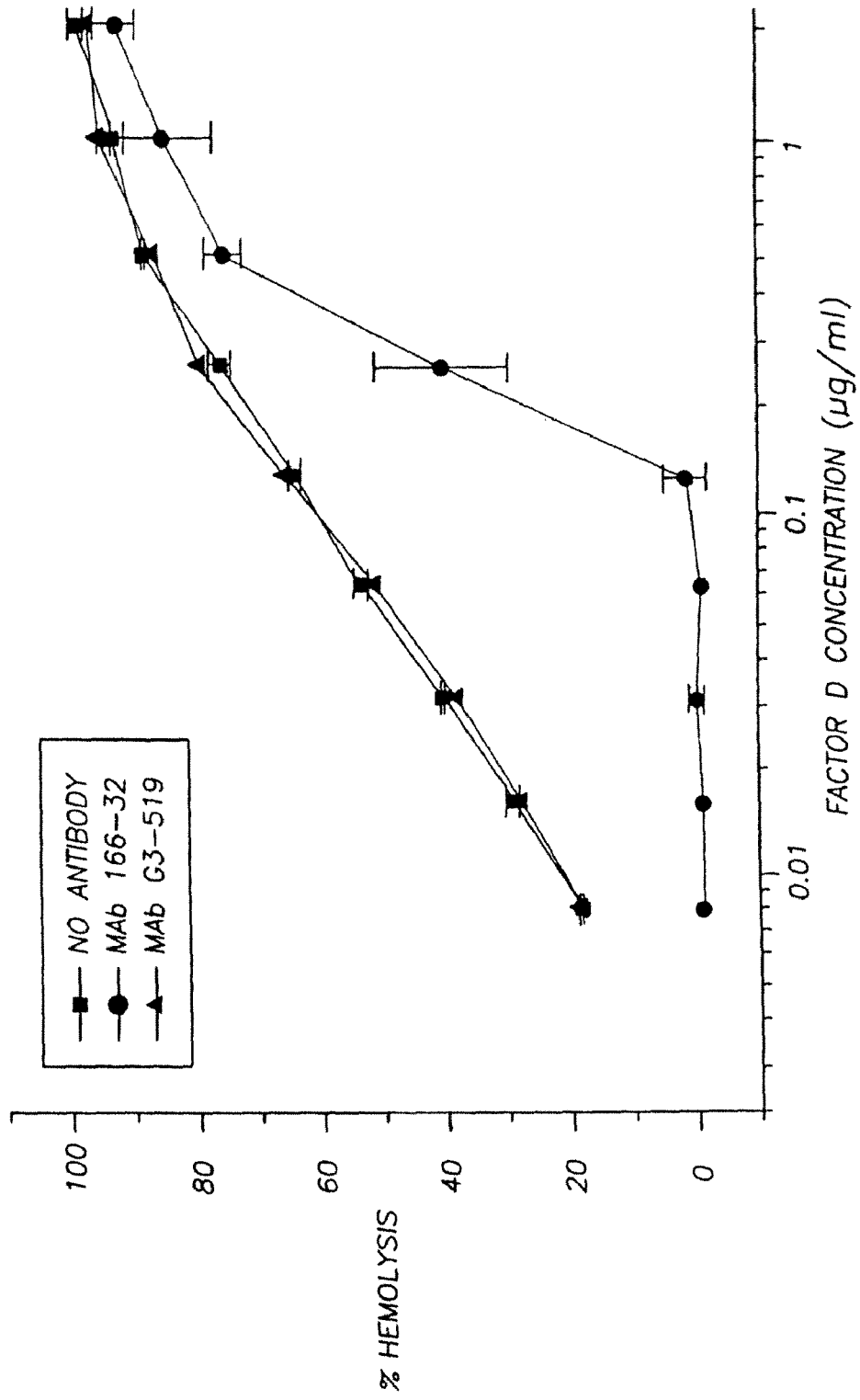
FIG. 5 shows the inhibition of alternative pathway (AP) hemolysis by MAb 166-32. Hemolysis was augmented by adding different concentrations of purified human factor D to a human serum depleted of its factor D by affinity chromatography using anti-factor D MAb 166-222. The assays were performed in the presence or absence of 0.3 μg/ml test MAbs. The line marked with filled squares represents no antibody added. The line marked with filled circles represents MAb 166-32. The line marked with filled triangles represents the irrelevant isotype-matched control MAb G3-519. The Y-axis represents the % hemolysis inhibition. The X-axis represents the concentration of factor D.

1. Inhibition of Factor D Dependent Hemolytic Assays Using Unsensitized Rabbit RBCs A human serum sample was first depleted of factor D by passing it through an affinity column packed with 3M Emphaze Biosupport Medium (Pierce, Rockford, Ill.) coupled with the anti-factor D MAb 166-222. The flow-through serum was tested to be inactive in triggering alternative pathway hemolysis due to the complete depletion of factor D. The procedure of this assay is similar to that described in Example 3 described above, except purified factor D of varying concentrations was added to the factor D depleted serum to reconstitute the hemolytic activity. Under these conditions, the hemolysis of rabbit RBCs was factor D dependent. It was shown that the reconstituted hemolytic activity is linearly proportional to the concentration of the supplemented factor D (from 0.01 μg/ml to 2 μg/ml (FIG. 5)). The data from FIG. 5 also shows that 0.3 μg/ml of MAb 166-32 can completely inhibit hemolysis of unsensitized rabbit RBCs in the presence of 0.1 μg/ml supplemented factor D, whereas the negative control MAb G3-519 has no effect on the factor D dependent hemolysis. These data suggest that MAb 166-32 can effectively inhibit the biological activity of human factor D at a molar ratio of 1:2 (MAb 166-32 to factor D). Therefore MAb 166-32 is a potent, high-affinity antibody to factor D. The antibody has the potential to be used clinically to treat diseases or indications caused by activation of the alternative complement pathway.

2. Inhibition of the Formation of Alternative C3 Convertase on EAC3b Cells

EAC3b cells are sheep RBCs coated with human C3b (purchased from the National Jewish Center of Immunology and Respiratory Medicine, Denver, Colo.). In this assay, the alternative C3 convertase was assembled on the surface of EAC3b cells by addition of factor B, factor P (properdin) and factor D. EAC3b cells ($5 \times 10^8$), which were then washed three times in DGVB$^{++}$ medium (50% veronal buffered saline, pH7.2, containing 0.075 mM CaCl$_2$, 0.25 mM MgCl$_2$, 0.1% gelatin, 2.5% (w/v) dextrose, and 0.01% sodium azide). The washed cells were then resuspended in 1.5 ml of DGVB$^{++}$, factor P (30 μg) and factor B (20 μg). The concentrations of factor P and factor B were pre-determined to be in excess. Fifty microliters of the cell suspension was added to each well of a round-bottom 96-well microtest plate. Then 50 μl of a mixture of factor D (1.2 ng/ml) and serially diluted MAb 166-32 or MAb G3-519 was added to the wells containing to the cells for incubation for 15 minutes at 30° C. The concentration of factor D (1.2 ng/ml) was pre-determined to give over 90% hemolysis under these conditions. After incubation, the cells were washed twice in GVB-EDTA medium (gelatin/veronal-buffered saline containing 10 mM EDTA). The cells were then resuspended in 30 μl of GVB-EDTA medium. To initiate hemolysis, 100 μl of guinea pig serum (Sigma) (diluted 1:10 in GVB-EDTA) were added to each well. The mixtures were then incubated at 37° C. for 30 minutes. The microtest plate was then centrifuged at 300×g for 3 minutes. The supernatant was collected for OD measurement at 405 nm.

Figure 6:
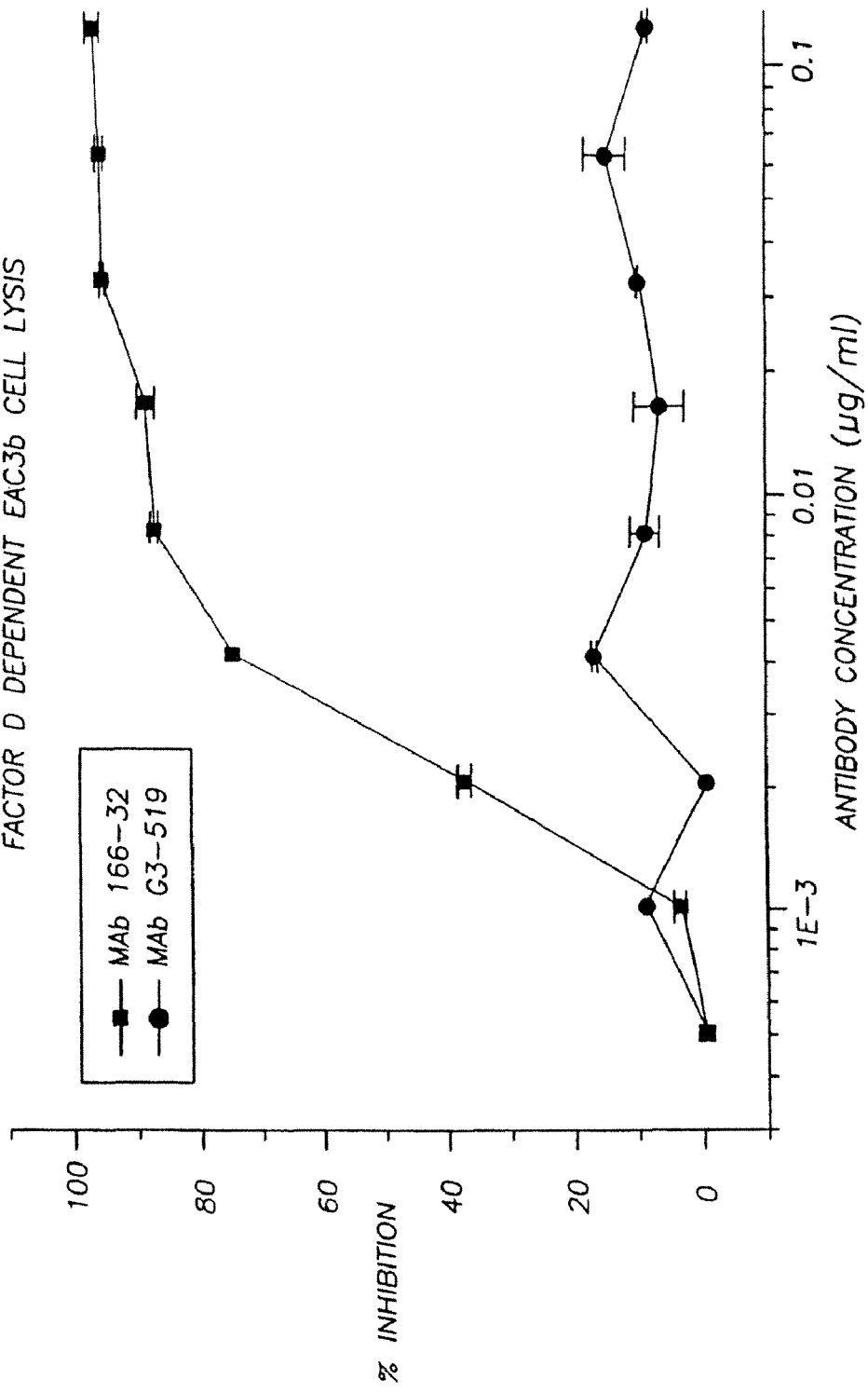
FIG. 6 shows the inhibition of factor-dependent EAC3b cell lysis by MAb 166-32. The alternative C3 convertase was assembled on EAC3b cells by incubation with factor B, factor P and factor D. Different concentrations of MAb 166-32 were added to the incubation buffer to inhibit the activity of factor D. The line marked with filled squares represents MAb 166-32. The line marked with filled circles represents MAb G3-519. The Y-axis represents the % hemolysis inhibition. The X-axis represents the concentration of the MAbs.

FIG. 6 shows the results of the experiments that MAb 166-32 inhibits the lysis of EAC3b cells, whereas the irrelevant MAb G3-519 does not. MAb 166-32 inhibits factor D from cleavage of factor B, therefore preventing the formation of C3 convertase on the surface of EAC3b cells.

Example 5

Inhibition of the Generation of C3a from Complement Activated Zymogen by MAb 166-32

To further ascertain the functional specificity of MAb 166-32 to factor D, the effect of the MAb on alternative complement activation on zymosan (activated yeast particles) was examined. Zymosan A (from *Saccharomyces cerevisiae*, Sigma) (1 mg/ml) was washed three times in GVB/Mg-EGTA and then resuspended in the same medium at 1 mg/ml. Twenty-five microliters of MAb 166-32 or G3-519 in different concentrations were mixed with 25 μl of human serum (diluted 1:5 in GVB/Mg-EGTA) in a microtube and incubated for 15 minutes at room temperature. The blank contained no antibody but the plain medium and the serum. After incubation, 50 μl of washed zymosan suspension were added to each tube for incubation for 30 minutes at 37° C. The microtubes were then centrifuged at 2000×g for 5 minutes, the supernatants were collected and mixed with equal volume of Specimen Stabilizing Solution (Quidel, San Diego, Calif.). The samples were frozen at −25° C. until being assayed. The concentration of C3a and sC5b-9 in the samples were measured by quantitative ELISA kits (Quidel) according to the procedures provided by the manufacturer.

Figure 7:
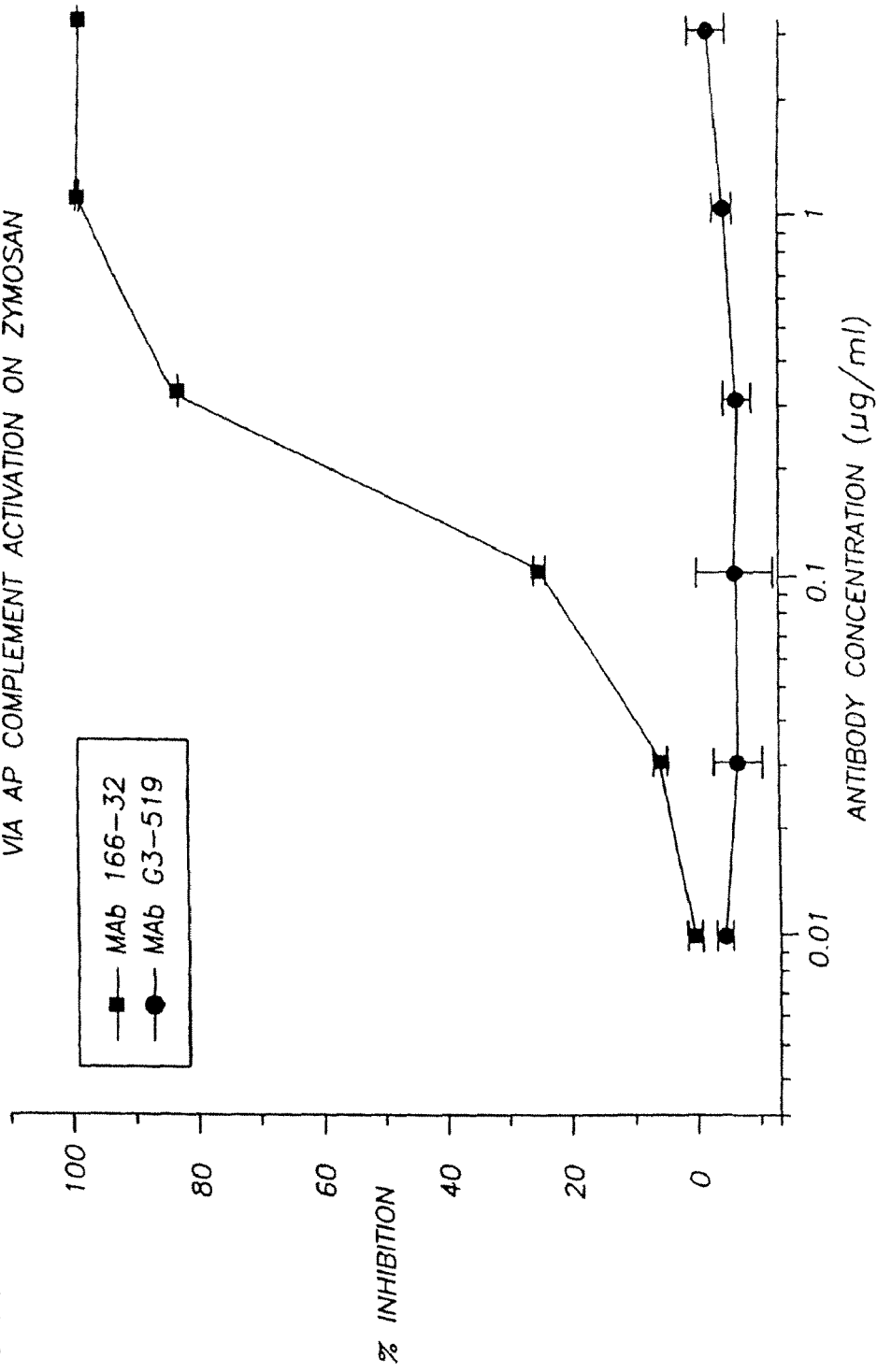
FIG. 7 shows the inhibition of C3a production from zymosan by MAb 166-32. Zymosan activated the alternative complement pathway in the presence of human serum. The production of C3a was measured by using an ELISA assay kit. The line marked with filled squares represents MAb 166-32. The line marked with filled circles represents the irrelevant isotype-control MAb G3-519. The Y-axis represents the % inhibition of C3a production. The X-axis represents the concentration of the MAbs.
Figure 8:
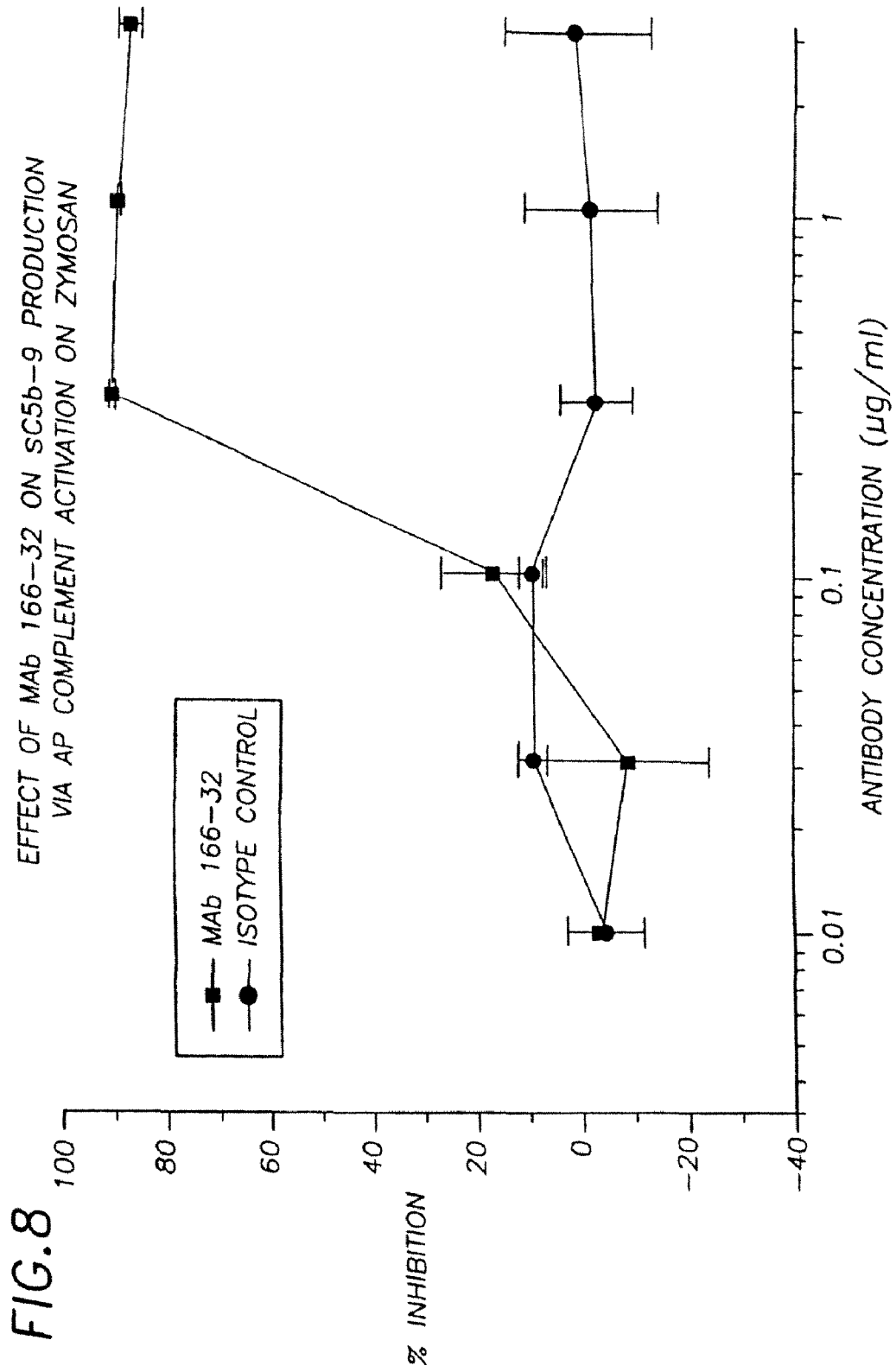
FIG. 8 shows the inhibition of sC5b-9 production from zymosan by MAb 166-32. Zymosan activated the alternative complement pathway in the presence of human serum. The production of sC5b-9 was measured by using an ELISA assay kit. The line marked with filled squares represents MAb 166-32. The line marked with filled circles represents the irrelevant isotype-control MAb G3-519. The Y-axis represents the % inhibition of sC5b-9 production. The X-axis represents the concentration of the MAbs.

FIG. 7 shows that MAb 166-32 inhibits the generation of C3a from complement-activated zymosan, whereas the irrelevant MAb G3-519 has no effect. These data suggest that MAb 166-32 inhibits the formation of C3 convertase by factor D. The complete inhibition of factor D by MAb 166-32 can effectively block the formation of C3 convertase as indicated by the inability to generate C3a. This will lead to the inhibition of C5 convertase in the subsequent steps of the complement cascade, as evidenced by the inhibition of sC5b-9 (MAC) formation (FIG. 8).

Example 6

Inhibition of Complement-Activated Hemolysis by the Fab of MAb 166-32

In order to examine whether monovalent form of MAb 166-32 is effective in inhibiting the alternative complement pathway as the parental bivalent MAb 166-32, the Fab of MAb 166-32 was prepared by papain digestion using a commercial reagent kit (Pierce). The Fab was then tested for inhibitory activity on the alternative pathway hemolysis using unsensitized rabbit RBCs as described above.

Figure 9:
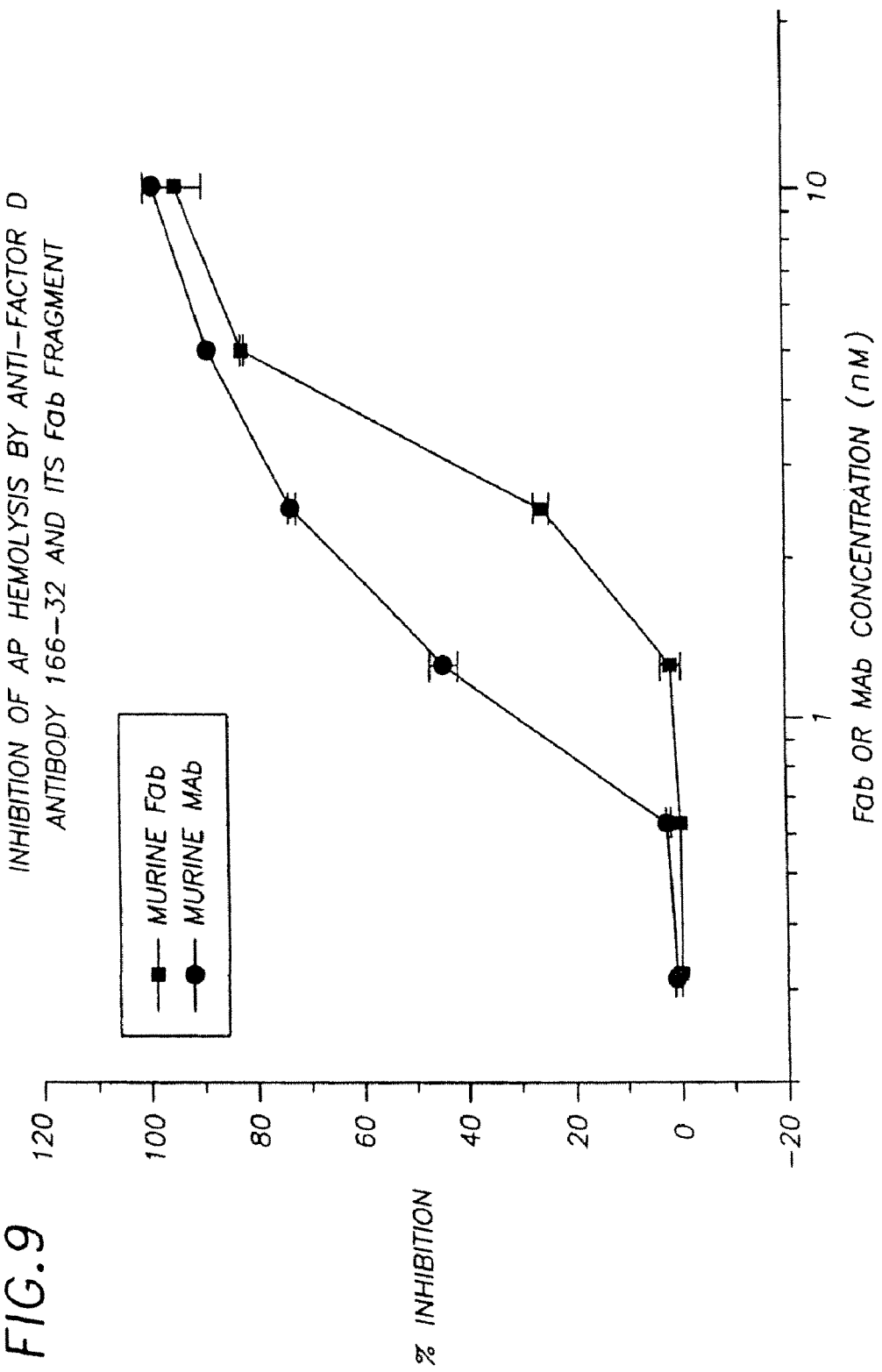
FIG. 9 shows the inhibition of alternative pathway hemolysis of unsensitized rabbit RBCs by MAb 166-32 and its Fab. The line marked with filled circles represents MAb 166-32 (whole IgG). The line marked with filled squares represents the Fab of the MAb 166-32. The Y-axis represents the % hemolysis inhibition. The X-axis represents the concentration of the MAbs.

FIG. 9 shows the data of the experiments that both the whole IgG and Fab show similar potency in blocking the alternative complement activation, taking into consideration that there are two binding sites per antibody molecule. These results suggest that monovalent form of MAb 166-32 is active and it retains the similar potency against factor D as its parental bivalent antibody. This property is important for the consideration of using Fab or single-chain Fv as the alternative products. One advantage of using the latter monovalent forms is that they will have better tissue penetration because of their smaller size. Inasmuch as the Fab of MAb 166-32 is active, it is likely that the binding epitope on factor D recognized by the MAb is functionally important.

Example 7

Effects of MAb 166-32 on Alternative Pathway Hemolysis Using Sera from Different Animal Species In order to study the cross-reactivity of MAb 166-32 with factor D from different animal species, alternative pathway hemolytic assays were performed using sera from different animal species. Fresh sera from different animal species (human, rhesus monkey, chimpanzee, baboon, cynomolgus monkey, sheep, dog, mouse, hamster, rat, rabbit, guinea pig and pig) were first tested for the CH50 values, which are defined as the dilution of the serum to achieve 50% lysis of unsensitized rabbit RBCs. The inhibitory activity of MAb 166-32 on the same hemolytic activity (CH50) of each serum was then tested and compared.

Figure 10:
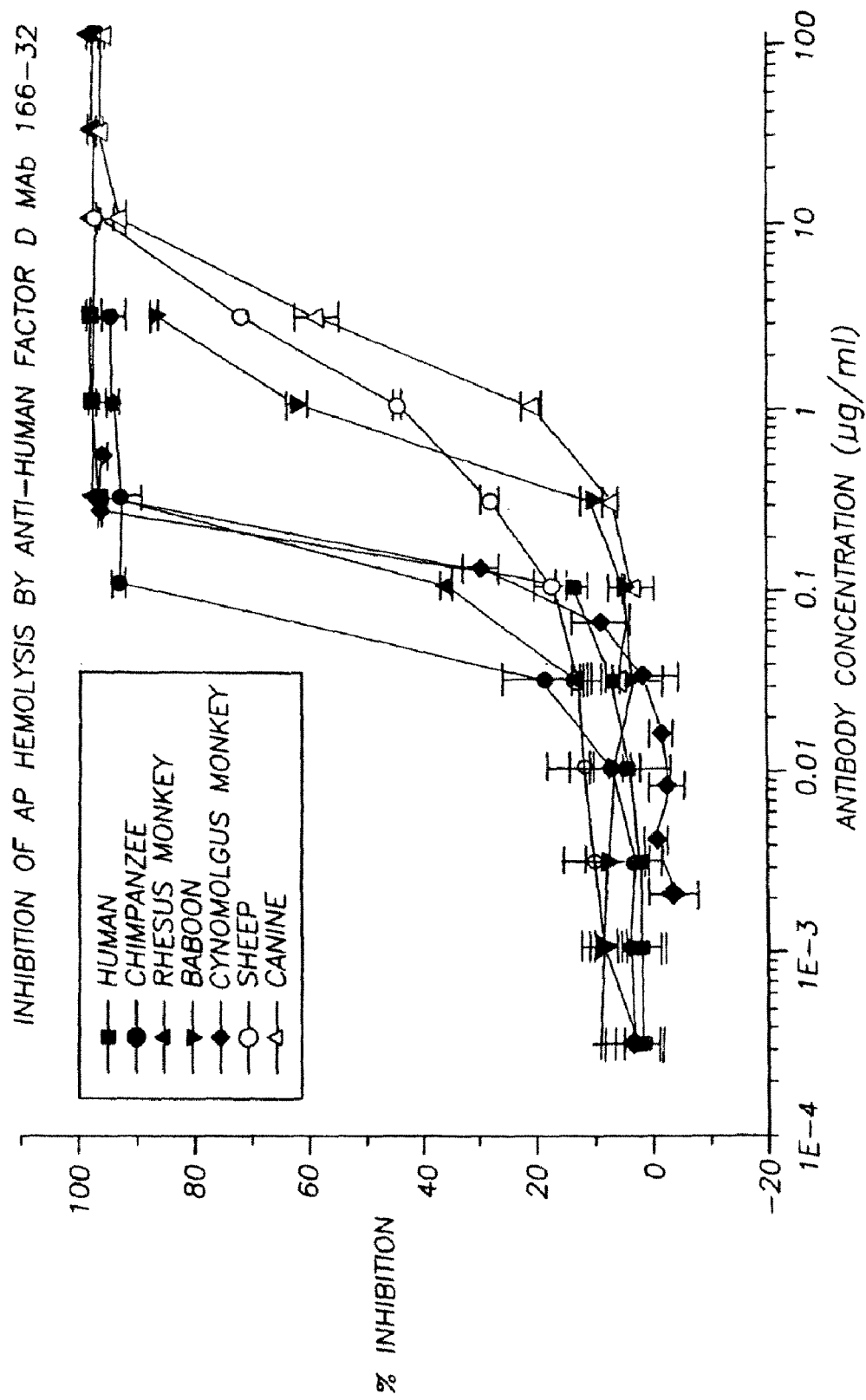
FIG. 10 shows the inhibitory effect of MAb 166-32 on factor D in sera from different animal species in alternative pathway hemolysis of unsensitized rabbit RBCs. The line marked with filled squares represents human serum. The line marked with filled circles represents chimpanzee serum. The line marked with filled triangles represents rhesus monkey serum. The line marked with filled, inverted triangles represents baboon serum. The line marked with filled diamonds represents cynomolgus monkey serum. The line marked with open circles represents sheep serum. The line marked with open triangles represents canine serum. The Y-axis represents the % hemolysis inhibition. The X-axis represents the concentration of MAb 166-32.

FIG. 10 shows that MAb 166-32 has strong inhibitory activity against sera from human, rhesus monkey, cynomolgus monkey and chimpanzee and moderate inhibitory activity against sera from baboon, sheep and dog. The antibody does not inhibit sera from mouse, hamster, rat, rabbit, guinea pig and pig. These data suggests that MAb 166-32 binds to an epitope on factor D shared by humans, rhesus monkeys, chimpanzees, baboons, cynomolgus monkeys, sheep and dogs.

Example 8

Construction of Human Factor D Mutants for Epitope Mapping of MAb 166-32

To delineate the binding epitope on human factor D recognized by MAb 166-32, the reactivity of the antibody with human factor D on Western blots was first tested. MAb 166-32 did not react with SDS-denatured human factor D (either reduced or non-reduced) immobilized on nitrocellulose membrane. This result indicates the MAb 166-32 binds native but not denatured factor D.

Since MAb 166-32 does not inhibit the hemolytic activity of mouse and pig factor D as described in Example 7, it is likely that MAb 166-32 binds to a site on human factor D that has a high degree of difference in the amino acid sequence from those of mouse and pig factor D. Based on this concept, various factor D mutants and hybrids were made by replacing amino acid residues in human factor D with the corresponding amino acid residues in the pig counterpart, for mapping the binding epitope of Mab 166-32, as described below.

1. Construction of Factor D Mutants and Hybrids

Human factor D gene segments were obtained by polymerase chain reaction (PCR) using human adipocyte cDNA (Clontech, San Francisco, Calif.) as the template and appropriate oligonucleotide primers. Amplified DNA fragments were digested with BamHI and EcoRI restriction enzymes and the digested product was inserted at the BamHI and EcoRI sites of the Baculovirus transfer vector pVL1393 (Pharmingen, San Diego, Calif.) to give the wild type pVL1393-factor D/Hu. The human factor D is designated as factor D/Hu. The nucleotide sequence and the deduced amino acid sequence of the mature human factor D protein are shown in SEQ ID NOS: 1 and 2 (R. T. White et al., *J. Biol. Chem.*, 1992; 267:9210-9213; GenBank accession number: M84526).

Pig factor D cDNA clone pMon24909 was obtained as a gift from J. L. Miner of University of Nebraska (GenBank accession number: U29948). The BamHI-EcoRI fragments of pMon24909 were cloned into pVL1393 to give pVL1393-factor D/Pig. The pig factor D is designated as factor D/Pig. The nucleotide sequence and the deduced amino acid sequence of the mature pig factor D protein are shown in SEQ ID NOS: 3 and 4.

Three human factor D mutants were constructed by using appropriate primers and overlapping PCR. The amino acid mutations were designed by replacing the amino acid residues in the human sequence with the corresponding amino acid residues of the pig sequence when the amino acid sequences of human and pig factor D are aligned for homology comparison. The first mutant, factor D/VDA, contained three amino acid mutations: V113E, D116E, and A118P. (This is a short-hand method of designating mutations in which, for example, V113E means that the valine at amino acid residue number 113 in human factor D was changed to glutamic acid in pig factor D). The second mutant, factor D/RH, contained two amino acid mutations: R156L and H159Y. The third mutant, factor D/L, contained a single mutation: L168M. DNA sequences encoding these mutants were confirmed by DNA sequencing. After digesting with appropriate enzymes, DNA fragments were inserted at the BamHI and EcoRI sites of the Baculovirus transfer vector pVL1393 to give pVL1393-factorD/VDA, pVL1393-factorD/RH and pVL1393-factorD/L, respectively.

Two chimeric human-pig factor D hybrids were also constructed by using appropriate primers and overlapping PCR. The first hybrid, factor D/Hupig, contained 52 human factor D-derived amino acids at the N-terminus, and the remaining amino acids were derived from the pig factor D. The other hybrid, factor D/Pighu, contained 52 pig factor D-derived amino acids at the N-terminus and the remaining amino acids were derived from the human factor D. The BamHI and EcoRI-digested DNA fragments were inserted at the BamHI and EcoRI sites of the Baculovirus transfer vector pVL1393 to give pVL1393-factorD/Hupig and pVL1393-factorD/Pighu.

2. Expression of Factor D Mutants and Hybrids

The procedures for transfection of the plasmids, generation of recombinant Baculoviruses, and production of the recombinant factor D proteins in insect cells Sf9 were done according to the manufacturer's manual (Baculovirus Expression Vector System, Pharmingen).

3. Purification of Factor D Mutants and Hybrids

Factor D mutant and hybrid proteins from the culture supernatants of infected Sf9 cells were purified by affinity chromatography using purified sheep anti-human factor D polyclonal antibodies (The Binding Site Limited, San Diego, Calif.). Three milliliters of sheep anti-human factor D antibodies (13.2 mg/ml) were equilibrated in a coupling buffer (0.1 M borate and 0.75 M $Na_2SO_4$, pH 9.0) and coupled with 4 ml of Ultralink Biosupport Medium (Pierce) for 2 hours at room temperature. The beads were washed first with 50 mM diethylamine, pH 11.5 to saturate all the remaining reactive sites and then with a buffer containing 10 mM Tris, 0.15 M NaCl, 5 mM EDTA, 1% Triton X-100, and 0.02% $NaN_3$, pH 8.0. The gel was stored in the buffer at 4° C.

Culture supernatant harvested from 100 ml spinner culture of Sf9 cells infected with the various Baculovirus mutants were passed through the sheep anti-factor D affinity column which was pre-equilibrated with PBS to remove the storage buffer. The bound factor D proteins were eluted with 50 mM diethylamine, pH 11.5. The collected fractions were immediately neutralized to pH 7.0 with 1 M Hepes buffer. Residual salts were removed by buffer exchange with PBS by Millipore membrane ultrafiltration (M.W. cut-off: 3,000) (Millipore Corp., Bedford, Mass.). Protein concentrations were determined by the BCA method (Pierce).

4. Factor D ELISA

The reactivity of MAb 166-32 with the various factor D mutants and hybrids was tested by ELISA. Different wells of 96-well microtest plates were coated with the proteins (factor D/Hu, factor D/Pig, factor D/Hupig, factor D/Pighu, factor D/VDH, factor D/RH, and factor D/L) by addition of 100 μl of each protein at 0.5 μg/ml in PBS. After overnight incubation at room temperature, the wells were treated with PBSTB (PBST containing 2% BSA) to saturate the remaining binding sites. The wells were then washed with PBST. One hundred microliters of serially diluted Mab 166-32 (1 μg/ml to 0.5 ng/ml) were added to the wells for 1 hour at room temperature. The wells were then washed with PBST. The bound antibody was detected by incubation with diluted HRP-goat anti-mouse IgG (Fc) (Jackson ImmunoResearch) for 1 hour at room temperature. Peroxidase substrate solution was then added for color development as described above. The OD was measured using an ELISA reader at 450 nm.

Figure 11:
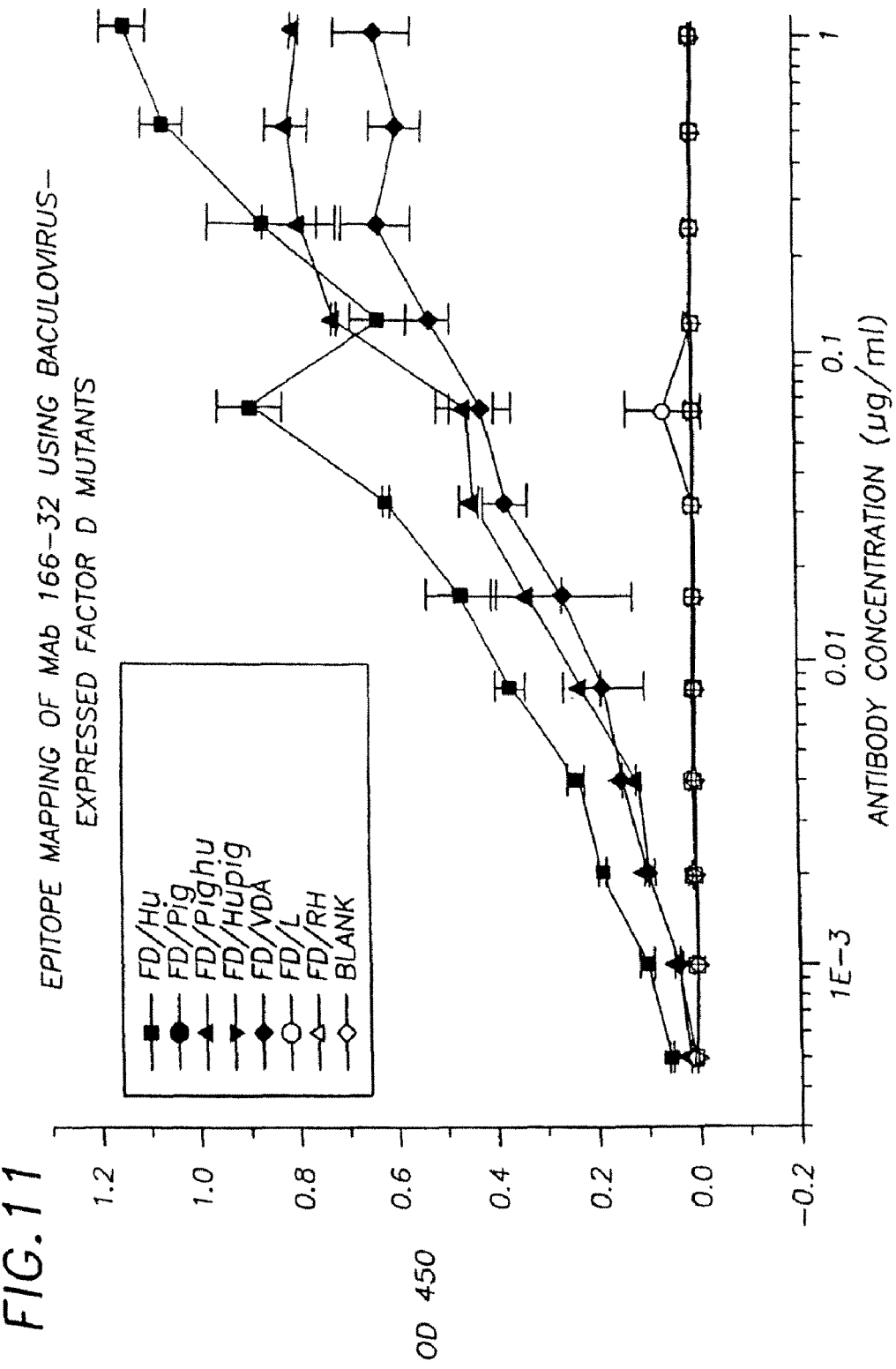
FIG. 11 shows the reactivity of MAb 166-32 with different Baculovirus expressed factor D ("FD") mutants and hybrids in ELISA. The line marked with filled squares represents human factor D, FD/Hu. The line marked with filled circles represents pig factor D, FD/Pig. The line marked with filled triangles represents FD/Pighu. The line marked with filled, inverted triangles represents the hybrid protein, FD/Hupig. The line marked with tilled diamonds represents the mutant protein, FD/VDA. The line marked with open circles represents the mutant protein, FD/L. The line marked with open triangles represents the mutant protein, FD/RH. The line marked with open diamonds represents the blank with no coating antigen. The recombinant proteins are further described in the text.

FIG. 11 shows that MAb 166-32 reacts with factor D/Hu, factor D/Pighu, and factor D/VDA, but not factor D/Pig, factor D/Hupig, factor D/RH, and factor D/L. The ELISA results indicate that amino acid residues Arg156, His159 and Leu168 of human factor D are essential for the binding of MAb 166-32. This is consistent with the fact that MAb 166-32 did not bind factor D/Hupig when the C-terminus portion of human factor D was replaced with that of pig. Amino acid residues Arg156, His159 and Leu168 are located in a so-called "methionine loop" constituted by a disulfide linkage between Cys154 and Cys170 with a methionine residue at position 169 (J. E. Volanakis et al., In: The Human Complement System in Health and Disease, J. E. Volanakis and M. M. Franks, eds., Marcel Dekker, 1998, pp. 49-81). Structurally, the "methionine loop" is a member of a rigid type 1 β turn. It is found to be exposed on the surface of the factor D molecule based on the data from X-ray crystallography studies (S. V. L. Narayana et al., J. Mol. Biol., 1994, 235: 695-708). However, the contribution of the "methionine loop" to substrate specificity and catalysis of factor D has never been studied (J. E. Volanakis et al., Protein Sci., 1996; 5: 553-564). The data here have demonstrated for the first time that the "methionine loop" plays an important role in the functional activity of factor D. MAb 166-32 and its Fab, when bound to this region on factor D, can effectively inhibit the catalysis of factor B.

Example 9

Cloning of Anti-Factor D MAb 166-32 Variable Region Genes and Construction and Expression of Chimeric 166-32 IgG and its Fab In order to reduce the immunogenicity of MAb 166-32 when used in humans, a chimeric form of MAb 166-32 was made by replacing the mouse constant regions with human constant regions of IgG1. Two forms of chimeric Fab of the antibody were also made by replacing the mouse constant regions with their human counterparts. The cloning of MAb 166-32 variable region genes and the construction and expression of the chimeric 166-32 antibody and its Fab are described below.

1. Cloning of Anti-Factor D MAb Variable Region Genes

Total RNA was isolated from the hybridoma cells secreting anti-Factor D MAb 166-32 using RNAzol following the manufacturer's protocol (Biotech, Houston, Tex.). First strand cDNA was synthesized from the total RNA using oligo dT as the primer. PCR was performed using the immunoglobulin constant (C) region-derived 3' primers and degenerate primer sets derived from the leader peptide or the first framework region of murine $V_H$ or $V_K$ genes as the 5' primers. Although amplified DNA was noted for $V_H$, no DNA fragment of expected lengths was amplified for $V_K$. Both $V_H$ and $V_K$ genes were cloned by anchored PCR.

Anchored PCR was carried out as described by Chen and Platsucas (*Scand. J. Immunol.*, 1992; 35: 539-549). For cloning the $V_K$ gene, double-stranded cDNA was prepared using the NotI-MAK1 primer (5'-TGCGGCCGCTGTAGGTGCT-GTCTTT-3' SEQ ID NO:5). Annealed adaptors AD1 (5'-GGAATTCACTCGTTATTCTCGGA-3' SEQ ID NO:6) and AD2 (5'-TCCGAGAATAACGAGTG-3' SEQ ID NO:7) were ligated to both 5' and 3' termini of the double-stranded cDNA. Adaptors at the 3' ends were removed by NotI digestion. The digested product was used as the template in PCR with the AD1 oligonucleotide as the 5' primer and MAK2 (5'-CAT-TGAAAGCTTTGGGGTAGAAGTTGTTC-3' SEQ ID NO:8) as the 3' primer. DNA fragments of approximately 500 bp were cloned into pUC19. Twelve clones were selected for further analysis. Seven clones were found to contain the CDR3 sequence specific for the Sp2/0 V message, and presumably were derived from the aberrant κ light chain messages of the fusion partner for the 166-32 hybridoma cell line. The NotI-MAK1 and MAK2 oligonucleotides were derived from the murine Cκ region, and were 182 and 84 bp, respectively, downstream from the first by of the Cκ gene. Three clones were analyzed by DNA sequencing, yielding sequences encompassing part of murine Cκ, the complete Vκ, and the leader peptide.

For cloning the $V_H$ gene, double-stranded cDNA was prepared using the NotI-MAG1 primer (5'-CGCGGCCG-CAGCTGCTCAGAGTGTAGA-3' SEQ ID NO:9). Annealed adaptors AD1 and AD2 were ligated to both 5' and 3' termini of the double-stranded cDNA. Adaptors at the 3' ends were removed by NotI digestion. The digested product was used as the template in PCR with the AD1 oligonucleotide and MAG2 (5'-CGGTAAGCTTCACTGGCTCAGGGAAATA-3' SEQ ID NO:10) as primers. DNA fragments of 500 to 600 bp in length were cloned into pUC19. The NotI-MAG1 and MAG2 oligonucleotides were derived from the murine Cγ 1 region, and were 180 and 93 bp, respectively, downstream from the first by of the murine Cγ 1 gene. Three clones were analyzed by DNA sequencing, yielding sequences encompassing part of murine Cγ 1, the complete $V_H$, and the leader peptide.

2. Construction of Expression Vectors for Chimeric 166-32 IgG and Fab

Figure 12:
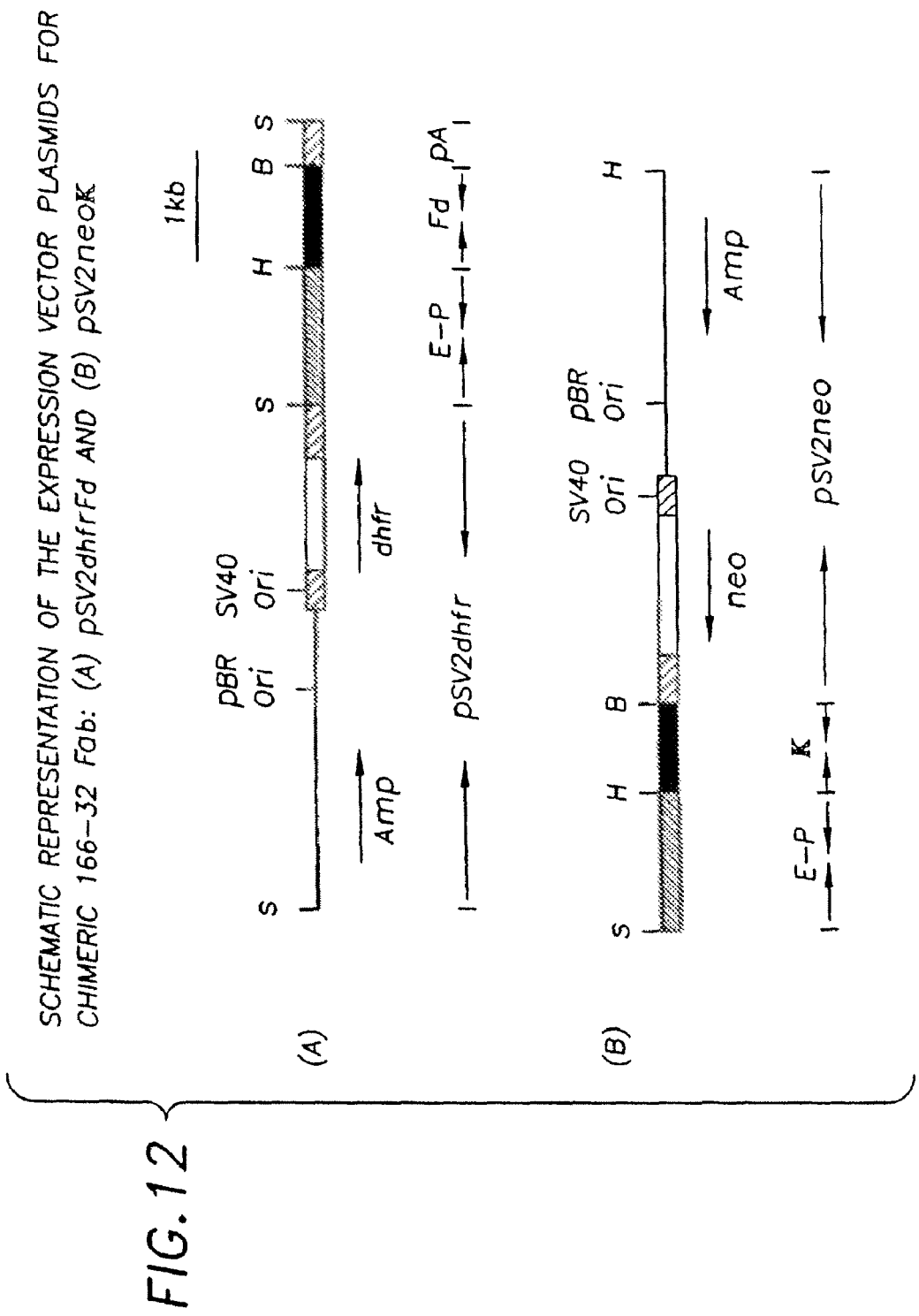
FIG. 12 shows the schematic representation of the expression vector plasmids for chimeric 166-32 Fab: (A) pSV2dhfrFd and (B) pSV2neok. Solid boxes represent the exons encoding the Fd or κ gene. Hatched segments represent the HCMV-derived enhancer and promoter elements (E-P), as indicated below. Open boxes are the dihydrofolate reductase (dhfr) and neo genes, as marked. The pSV2 plasmid consists of DNA segments from various sources: pBR322DNA (thin line) contains the pBR322 origin of DNA replication (pBR ori) and the lactamase ampicillin resistance gene (Amp); SV40 DNA, represented by wider hatching and marked, contains the SV40 origin of DNA replication (SV40 ori), early promoter (5' to the dhfr and neo genes), and polyadenylation signal (3' to the dhfr and neo genes). The SV40-derived polyadenylation signal (pA) is also placed at the 3' end of the Fd gene.

The $V_H$ and Vκ genes were used as templates in PCR for adding the Kozak sequence to the 5' end and the splice donor to the 3' end. After the sequences were analyzed to confirm the absence of PCR errors, the $V_H$ and Vκ genes were inserted into expression vector cassettes containing human Cγ 1 and Cκ respectively, to give pSV2neoV$_H$-huCγ1 and pSV2neoV-huCκ. CsCl gradient-purified plasmid DNAs of the heavy- and light-chain vectors were used to transfect COS cells by electroporation. After 48 hours, the culture supernatant was tested by ELISA to contain approximately 200 ng/ml of chimeric IgG. The cells were harvested and total RNA was prepared. First strand cDNA was synthesized from the total RNA using oligo dT as the primer. This cDNA was used as the template in PCR to generate the Fd and κ DNA fragments. For the Fd gene, PCR was carried out using (5'-AAGAAGCT-TGCCGCCACCATGGATTGGCTGTGGAACT-3' SEQ ID NO:11) as the 5' primer and a CH1-derived 3' primer (5'-CGGGATCCTCAAACTTTCTTGTCCACCTTGG-3' SEQ ID NO:12). DNA sequence was confirmed to contain the complete $V_H$ and the CH1 domain of human IgG1. After digestion with the proper enzymes, the Fd DNA fragments were inserted at the HindIII and BamHI restriction sites of the expression vector cassette pSV2dhfr-TUS to give pSV2dhfrFd (FIG. 12A).

For the κ gene, PCR was carried out using (5'-AAGAAAGCTTGCCGCCACCATGTTCTCACTAGCTCT-3' SEQ ID NO:13) as the 5' primer and a Cκ-derived 3' primer (5'-CGGGATCCTTCTCCCTCTAACACTCT-3' SEQ ID NO: 14). DNA sequence was confirmed to contain the complete Vκ and human Cκ regions. After digestion with proper restriction enzymes, the κ DNA fragments were inserted at the Hind III and BamHI restriction sites of the expression vector cassette pSV2neo-TUS to give pSV2neoκ (FIG. 12B). The expression of both Fd and κ genes are driven by the HCMV-derived enhancer and promoter elements. Since the Fd gene does not include the cysteine amino acid residue involved in the inter-chain disulfide bond, this recombinant chimeric Fab contains non-covalently linked heavy- and light-chains. This chimeric Fab is designated as cFab.

To obtain recombinant Fab with an inter-heavy and light chain disulfide bond, the above Fd gene was extended to include the coding sequence for additional 9 amino acids (EPKSCDKTH SEQ ID NO:15) from the hinge region of human IgG1. The BstEII-BamHI DNA segment encoding 30 amino acids at the 3' end of the Fd gene was replaced with DNA segments encoding the extended Fd. Sequence of the extended Fd with additional 9 amino acids from the hinge region of human IgG1 was confirmed by DNA sequencing. This Fd/9aa gene was inserted into the expression vector cassette pSV2dhfr-TUS to give pSV2dhfrFd/9aa. This chimeric Fab is designated as cFab/9aa.

3. Expression of Chimeric 166-32 IgG and Fab

To generate cell lines secreting chimeric 166-32 IgG, NS0 cells were transfected with purified plasmid DNAs of pSV2neoV$_H$-huCγ1 and pSV2neoV-huCκ by electroporation. Transfected cells were selected in the presence of 0.7 mg/ml G418. Cells were grown in a 250-ml spinner flask using serum-containing medium.

To generate cell lines secreting chimeric 166-32 Fab, CHO cells were transfected with purified plasmid DNAs of pSV2dhfrFd (or pSV2dhfrFd/9aa) and pSV2neoκ by electroporation. Transfected cells were selected in the presence of G418 and methotrexate. Selected cell lines were amplified in increasing concentrations of methotrexate. Cells were single-cell subcloned by limiting dilution. High-producing single-cell subcloned cell lines were then grown in 100-ml spinner culture using serum-free medium.

4. Purification of Chimeric 166-32 IgG

Culture supernatant of 100-ml spinner culture was loaded on a 10-ml PROSEP-A column (Bioprocessing, Inc., Princeton, N.J.). The column was washed with 10 bed volumes of PBS. The bound antibody was eluted with 50 mM citrate buffer, pH 3.0. Equal volume of 1M Hepes, pH 8.0 was added to the fraction containing the purified antibody to adjust the pH to 7.0. Residual salts were removed by buffer exchange with PBS by Millipore membrane ultrafiltration (M.W. cut-off: 3,000). The protein concentration of the purified antibody was determined by the BCA method (Pierce).

5. Purification of Chimeric 166-32 Fab

Chimeric 166-32 Fab was purified by affinity chromatography using a mouse anti-idiotypic MAb to MAb 166-32. The anti-idiotypic MAb is designated as MAb 172-25-3. It was made by immunizing mice with MAb 166-32 conjugated with keyhole limpet hemocyanin (KLH) and screening for specific MAb 166-32 binding could be competed with human factor D.

The affinity chromatography matrix was prepared by mixing 25 mg MAb 172-25-3 with 5 ml of dry azlactone beads (UltraLink Biosupport Medium, Pierce) in a coupling buffer (0.1 M borate and 0.75 M $Na_2SO_4$, pH 9.0) for 2 hours at room temperature. Then the residual reactive sites were blocked with 1 Methanolamine, pH 9.0 for 2.5 hours at room temperature. The beads were then washed in a buffer containing 10 mM Tris, 0.15 M NaCl, 5 mM EDTA, 1% Triton X-100 and 0.02% $NaN_3$, pH 8.0) and stored then at 4° C.

For purification, 100 ml of supernatant from spinner cultures of CHO cells producing cFab or cFab/9aa were loaded onto the affinity column coupled with MAb 172-25-3. The column was then washed thoroughly with PBS before the bound Fab was eluted 50 mM diethylamine, pH 11.5. Residual salts were removed by buffer exchange as described above. The protein concentration of the purified Fab was determined by the BCA method (Pierce).

6. SDS-PAGE of Chimeric 166-32 IgG, cFab and cFab/9aa

The purified chimeric 166-32 IgG, cFab and cFab/9aa were analyzed for purity and molecular size by SDS-PAGE. The proteins were treated with sample buffers with or without β-mercaptoethanol. The samples were then run on pre-cast gels (12.5%) (Amersham Pharmacia Biotech, Uppsala, Sweden) together with pre-stained molecular weight standard (low molecular weight range) (BIO-RAD Laboratories, Hercules, Calif.) using the PhastSystem (Amersham Pharmacia Biotech). The gels were then stained in Coomassie Brilliant Blue solution (BIO-RAD) for 5 minutes and then de-stained in an aqueous solution containing 40% methanol and 10% acetic acid.

The results of an SDS-PAGE of cFab, cFab/9aa and chimeric IgG treated under both non-reducing and reducing condition, showed chimeric IgG has a protein band of 150 kD, and two protein bands of heavy (HC) and light (LC) chains of approximately 50 kD and 29 kD, respectively. As expected, cFab/9aa had only 1 protein band of about 40 kD under non-reducing condition, indicating that the heavy and light chains are linked by an inter-chain disulfide bond. On the other hand, cFab showed two protein bands under non-reducing condition, indicating that the heavy and light chains are not linked by an inter-chain disulfide bond.

7. Determination of the Activities of Chimeric 166-32 IgG, cFab and cFab/9aa

Figure 13:
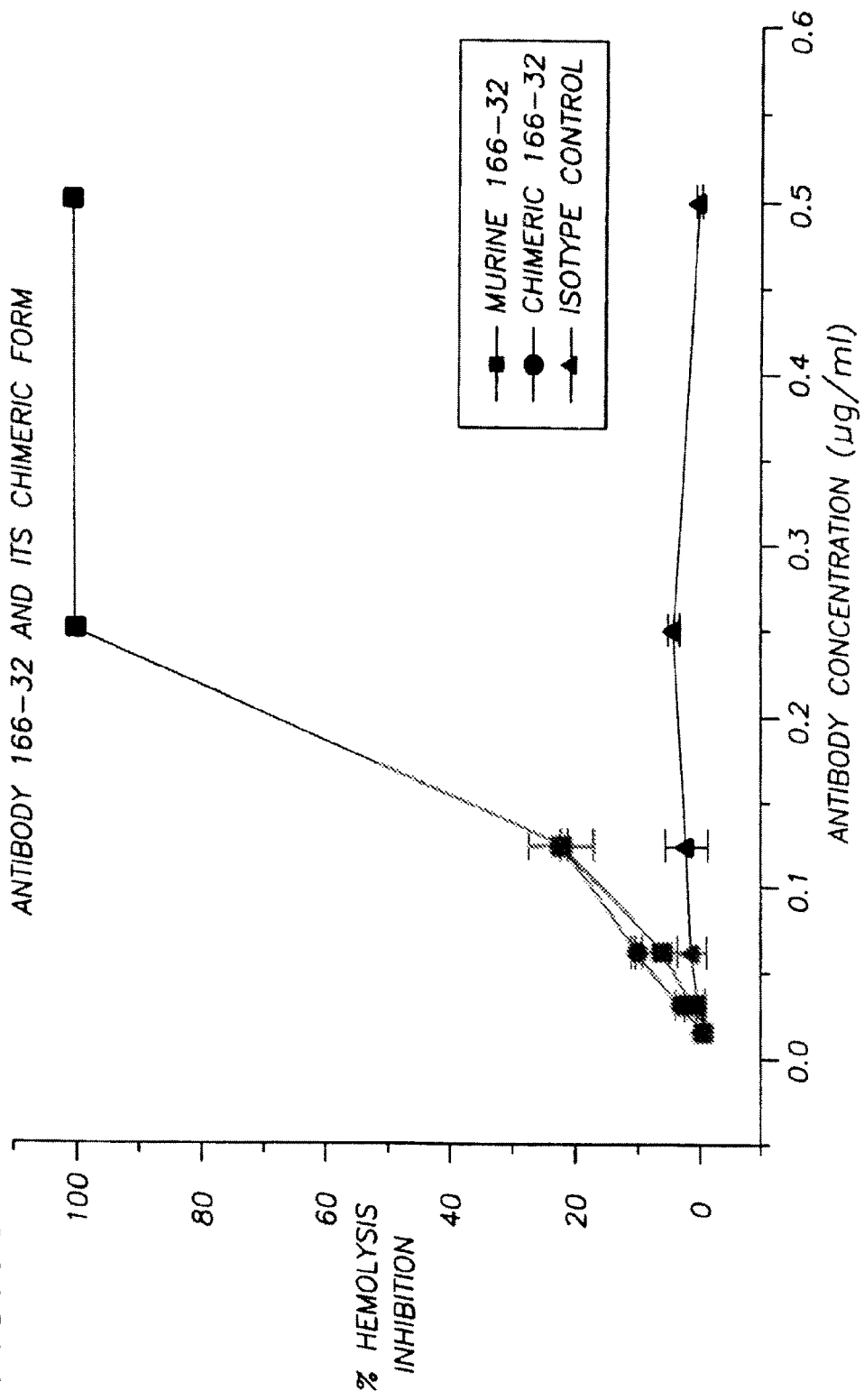
FIG. 13 shows the inhibition of alternative pathway (AP) hemolysis of unsensitized rabbit RBCs. The line marked with filled squares represents the murine MAb 166-32. The line marked with filled circles represents chimeric MAb 166-32. The line marked with filled triangles represents isotype-matched negative control antibody G3-519. The Y-axis represents % inhibition of hemolysis. The X-axis represents the antibody concentration.
Figure 14:
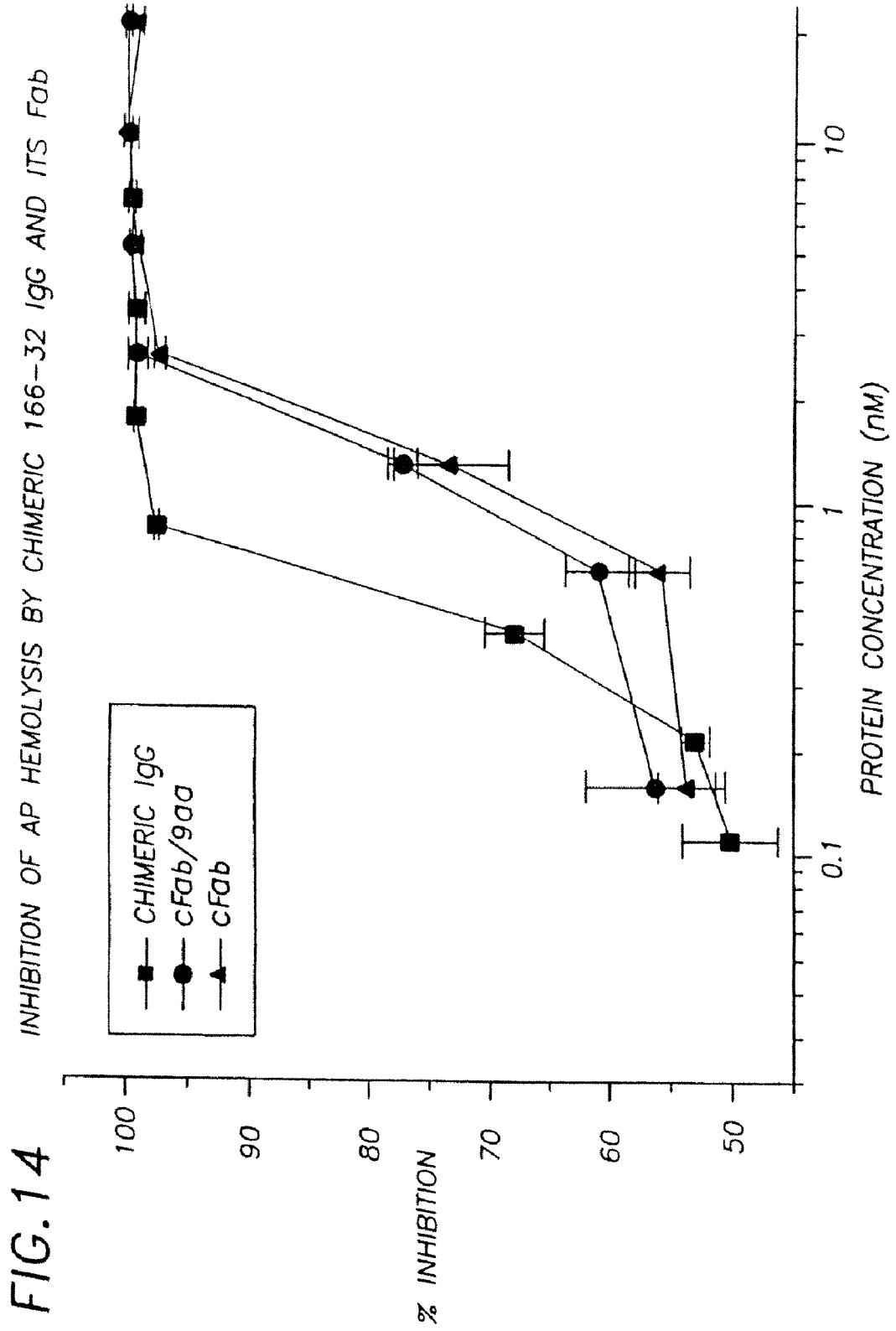
FIG. 14 shows the inhibition of alternative pathway (AP) hemolysis of unsensitized rabbit RBCs. The line marked with filled squares represents chimeric 166-32 IgG. The line marked with filled circles represents cFab/9aa. The line marked with filled triangles represents cFab. The Y-axis represents % inhibition of hemolysis. The X-axis represents the protein concentration of the IgG and Fab.

The activities of chimeric 166-32 IgG, cFab and cFab/9aa were determined by using the alternative complement hemolytic assay described above. FIG. 13 shows that the murine and chimeric forms of MAb 166-32 have identical potency in inhibiting factor D. FIG. 14 shows that cFab and cFab/9aa have almost identical potency in inhibiting factor D. Most importantly, the potency of the two forms of chimeric Fab is identical to that of the chimeric IgG, taking into consideration that there are two binding sites per IgG molecule. Together, the results demonstrate that chimeric IgG, cFab and cFab/9aa retain the potency of the parental murine MAb 166-32.

Example 10

Protection of Complement-Mediated Tissue Damage by Mab 166-32 in an Ex Vivo Model of Rabbit Hearts Perfused with Human Plasma Activation of the complement system contributes to hyperacute rejection of xenografts. It may occur as a result of binding of complement fixing antibodies, the direct activation of complement via the alternative pathway on foreign cell surfaces, and/or the failure of complement regulation by the foreign organ (J. L. Platt et al., *Transplantation*, 1991; 52: 937-947). Depending on the particular species-species interaction, complement activation through either the classical or alternative pathway predominates, though in some cases both pathways may be operative (T. Takahashi et al., *Immunol. Res.* 1997; 16: 273-297). Previous studies have shown that hyperacute rejection can occur in the absence of anti-donor antibodies via activation of the alternative pathway (P. S. Johnston et al., *Transplant. Proc.*, 1991; 23: 877-879).

To demonstrate the importance of the alternative complement pathway in tissue damage, the anti-factor D MAb 166-32 was tested using an ex vivo model in which isolated rabbit hearts were perfused with diluted human plasma. This model was previously shown to cause damage to the rabbit myocardium due to the activation of the alternative complement pathway (M. R. Gralinski et al., *Immunopharmacology*, 1996: 34:79-88).

1. Langendorff Perfused Rabbit Hearts:

Male, New Zealand White rabbits (2.2-2.4 kg) were euthanized by cervical dislocation. The hearts were removed rapidly and attached to a cannula for perfusion through the aorta. The perfusion medium consisted of a recirculating volume (250 ml) modified Krebs-Henseleit (K-H) buffer (pH 7.4, 37° C.) delivered at a constant rate of 20-25 ml/min. The composition of the buffer medium in millimoles per liter was as follows: NaCl, 117; KCl, 4.0; $CaCl_2.H_2O$, 2.4; $MgCl_2.6H_2O$, 1.2; $NaHCO_3$, 25; $KH_2PO_4$, 1.1; glucose, 5.0; monosodium L-glutamate, 5.0; sodium pyruvate, 2.0; and BSA, 0.25% (w/v). The K-H buffer passed through a gas porous "lung" consisting of Silastic™ Laboratory Grade Tubing (Dow Corning, Midland, Mich.), 55.49 meters in length, with an inner diameter of 1.47 mm and an outer diameter of 1.96 mm. The membranous "lung" was exposed continuously to a mixture of 95% $O_2$/5% $CO_2$ to obtain an oxygen partial pressure within the perfusion medium equal to 500 mm Hg. The hearts were paced throughout the protocol via electrodes attached to the right atrium. Pacing stimuli (3 Hz, 4 msec duration) were delivered from a laboratory square wave generator (Grass SD-5, Quincy, Mass.). The pulmonary artery was cannulated with polyethylene tubing to facilitate collection of the pulmonary artery effluent, representing the coronary venous return. The superior and inferior vena cava and the pulmonary veins were ligated to prevent exit of the perfusate from the severed vessels. A left ventricular drain, thermistor probe, and latex balloon were inserted via the left atrium and positioned in the left ventricle. The fluid-filled latex balloon was connected with rigid tubing to a pressure transducer to permit for measurement of left ventricular systolic and end-diastolic pressures. The left ventricular developed pressure is defined as the difference between the left ventricular systolic and end-diastolic pressures. The intraventricular balloon was expanded with distilled water to achieve an initial baseline left ventricular end-diastolic pressure of 5 mm Hg. Coronary perfusion pressure was measured with a pressure transducer connected to a side-arm of the aortic cannula. All hemodynamic variables were monitored continuously using a multichannel recorder (Grass Polygraph 79D, Quincy, Mass.). The isolated hearts were maintained at 37° C. throughout the experimental period by enclosing them in a temperature-regulated double-lumen glass chamber and passing the perfusion medium through a heated reservoir and delivery system.

2. Antibody Treatments:

Two treatment groups were used to determine the ability of anti-factor D MAb 166-32 to inhibit the effects of complement activation in isolated rabbit hearts perfused with human plasma. Group 1: Isotype-matched negative group, consisted of hearts perfused with 4% human plasma in the presence of 0.3 µg/ml of MAb G3-519 (n=6) specific to HIV-1 gp120. Group 2: Treatment group, consisted of hearts perfused with 4% human plasma in the presence of 0.3 µg/ml of MAb 166-32 (n=6). The human plasma was separated from freshly collected whole blood and stored at −80° C. until use. This percentage of human plasma was chosen because it severely impairs myocardial function over a reasonable length of time and allows one to assess the efficacy of a treatment regimen. Higher concentrations of human plasma in this system cause the heart to rapidly develop contracture, making it difficult to analyze the effects of a drug at a low concentration. Preliminary studies had determined that 0.3 µ/ml was the minimal effective concentration that could protect the isolated heart from the effects of complement activation. All hearts underwent 10-15 minutes of equilibration in the Langendorff apparatus before addition of either antibody to the perfusion medium. Ten minutes after the addition of antibody, 4% human plasma was added to the perfusion medium (250 ml, recirculating). Hemodynamic variables, including coronary perfusion pressure (CPP), left ventricular systolic pressure (LVSP), left ventricular end-diastolic pressure (LVEDP), and left ventricular developed pressure (LVDP) were recorded before the addition of antibody (baseline), before the addition of 4% human plasma, and every 10 minutes thereafter, for 60 minutes.

Figure 15:
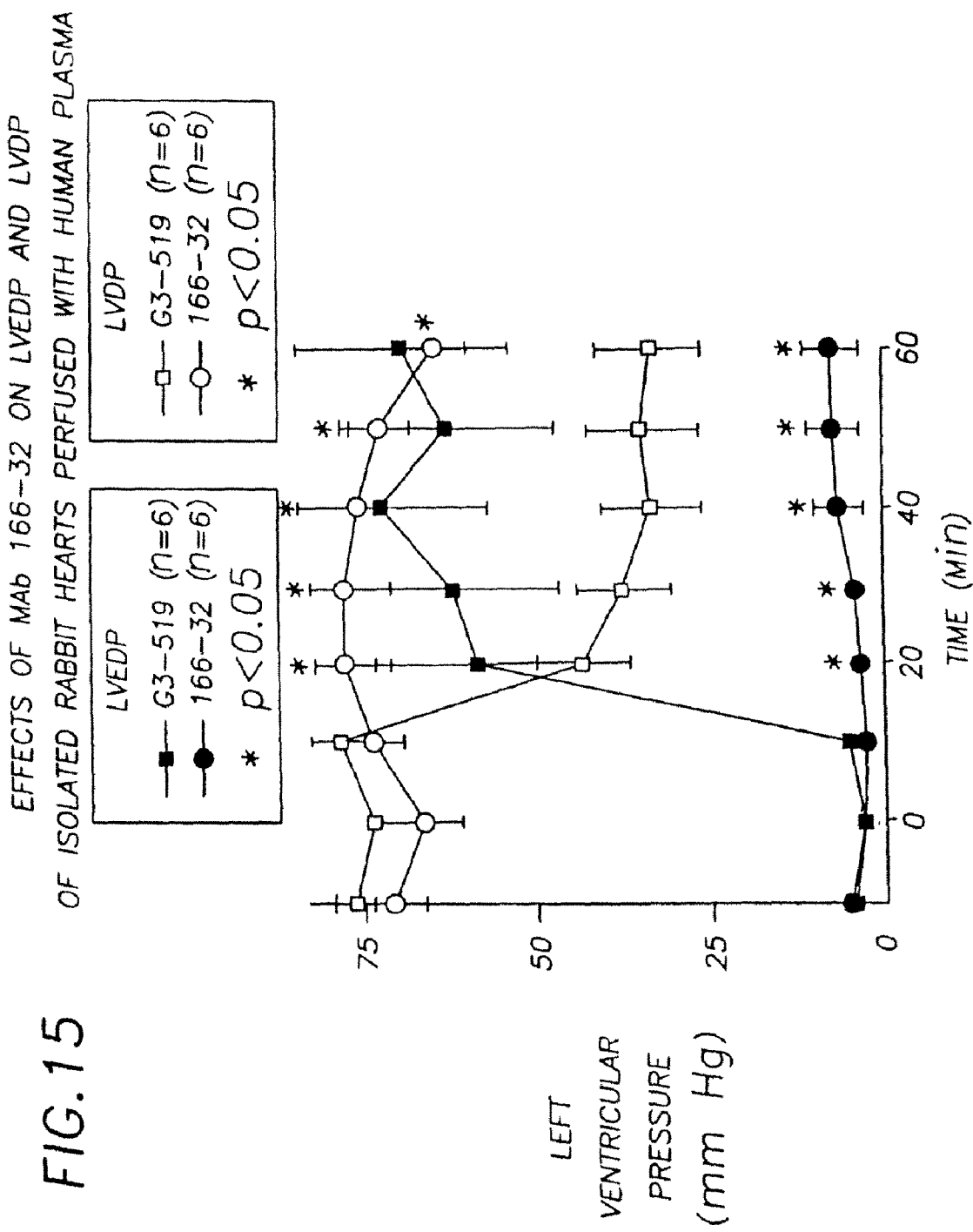
FIG. 15 shows the effects of anti-factor D MAb 166-32 treatment on the hemodynamic functions of isolated rabbit hearts perfused with human plasma. Left ventricular end-diastolic pressure (LVEDP) is represented by filled circles (for MAb 166-32) and filled squares (for MAb G3-519). Left ventricular developed pressure (LVDP) is represented by open circles (for MAb 166-32) and open squares (for MAb G3-519). MAb G3-519 is the isotype-matched irrelevant control.

MAb 166-32 (0.3 µg/ml) attenuated the increase in coronary perfusion pressure (CPP) when compared to hearts treated with MAb G3-519 (0.3 µg/ml) when exposed to 4% human plasma. A rise in CPP indicates coronary vascular resistance which is often associated with myocardial tissue damage. Isolated rabbit hearts perfused with MAb 166-32 maintained left ventricular end-diastolic pressure (LVEDP), in marked contrast to the results obtained with MAb G3-519 (FIG. 15). The latter group of hearts developed a progressive increase in LVEDP after exposure to 4% human plasma, indicating contracture or a failure of the ventricle to relax during diastole (FIG. 15). MAb 166-32 also attenuated the decrease in left ventricular developed pressure (LVDP) compared to the hearts treated with MAb G3-519 after exposure to diluted human plasma. (FIG. 15).

Figure 16:
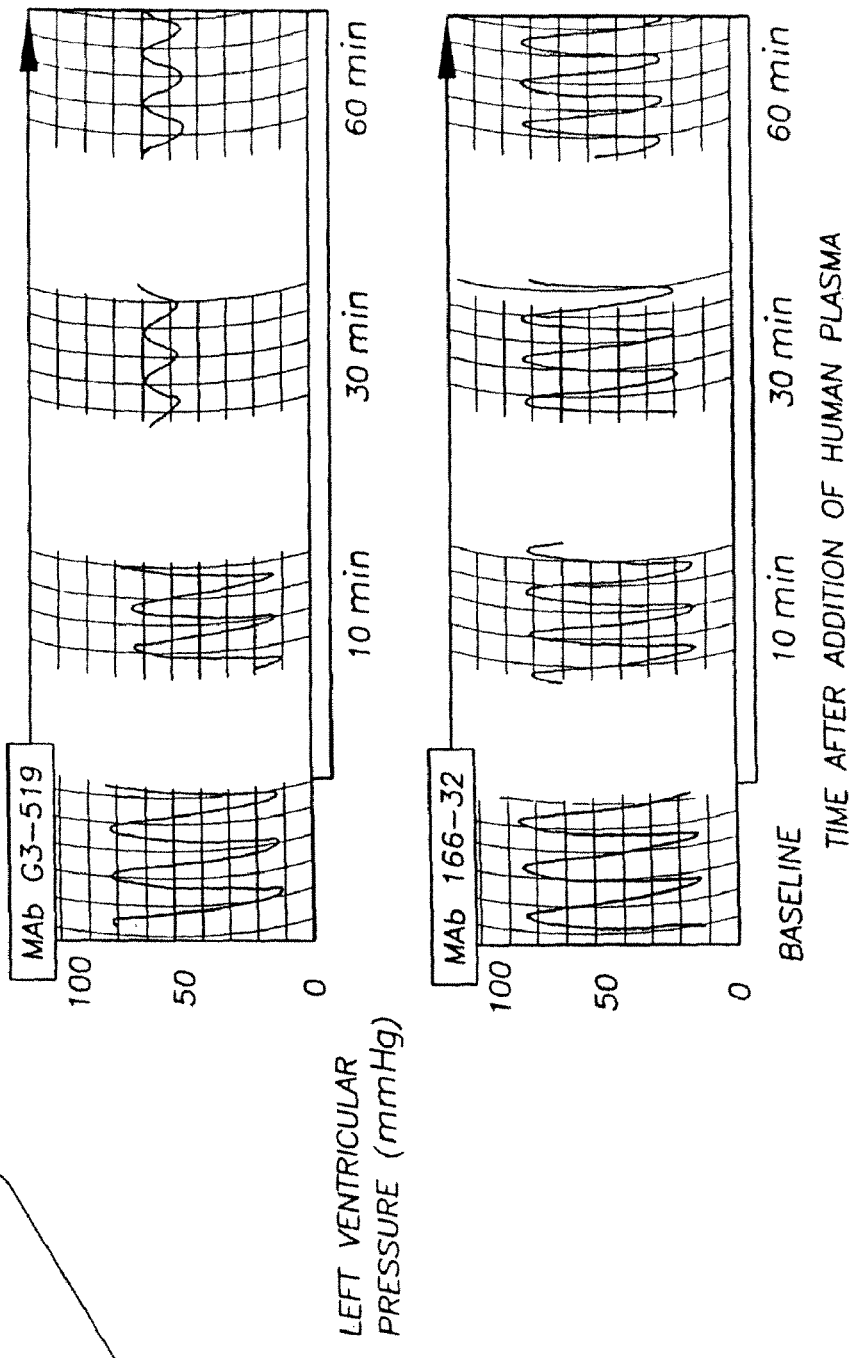
FIG. 16 is a typical representation of left ventricular developed pressure (LVDP) by the two antibody groups in an isolated rabbit heart study. The upper panel represents a heart treated with the negative control antibody, MAb G3-519, and the lower panel a heart treated with MAb 166-32. The MAb G3-519 treated heart was not able to maintain LVDP after challenge with 4% human plasma, while the MAb 166-32 treated heart retained almost baseline LVDP after 60 minutes of perfusion with 4% human plasma.

FIG. 16 depicts representative recordings of cardiac function obtained before and after 10, 30 and 60 minutes of perfusion in the presence of 4% human plasma. The progressive increase in the LVEDP and the decrease in the LVDP of a MAb G3-519 treated rabbit heart is obvious after 10 minutes with progressive deterioration of ventricular function over the subsequent 50 minutes. On the other hand, preservation of ventricular function of a heart treated with MAb 166-32 is evident over the period of 60 minutes.

Taken together, the hemodynamic data indicate that anti-factor D MAb 166-32 protects isolated rabbit hearts from human complement-mediated injury as manifested by an overall maintenance of myocardial function after challenge with human plasma.

3. Complement Bb ELISA:

Factor D catalyzes the cleavage of bound factor B, yielding the Ba and Bb fragments. The concentration of Bb present serves as an index of factor D activity. The concentrations of activated component Bb in the lymphatic fluid collected from the isolated rabbit hearts were measured using a commercially available ELISA kit (Quidel). The assays made use of a MAb directed against human complement Bb to measure the activation of human complement system during perfusion of rabbit hearts in the presence of human plasma. Lymphatic effluent from the severed lymphatic vessels was collected from the apex of the heart, snap-frozen in liquid nitrogen, and stored at $-70°$ C. until assayed. The flow rate of the lymphatic effluent was recorded and accounted for in order to normalize the Bb concentration.

Figure 17:
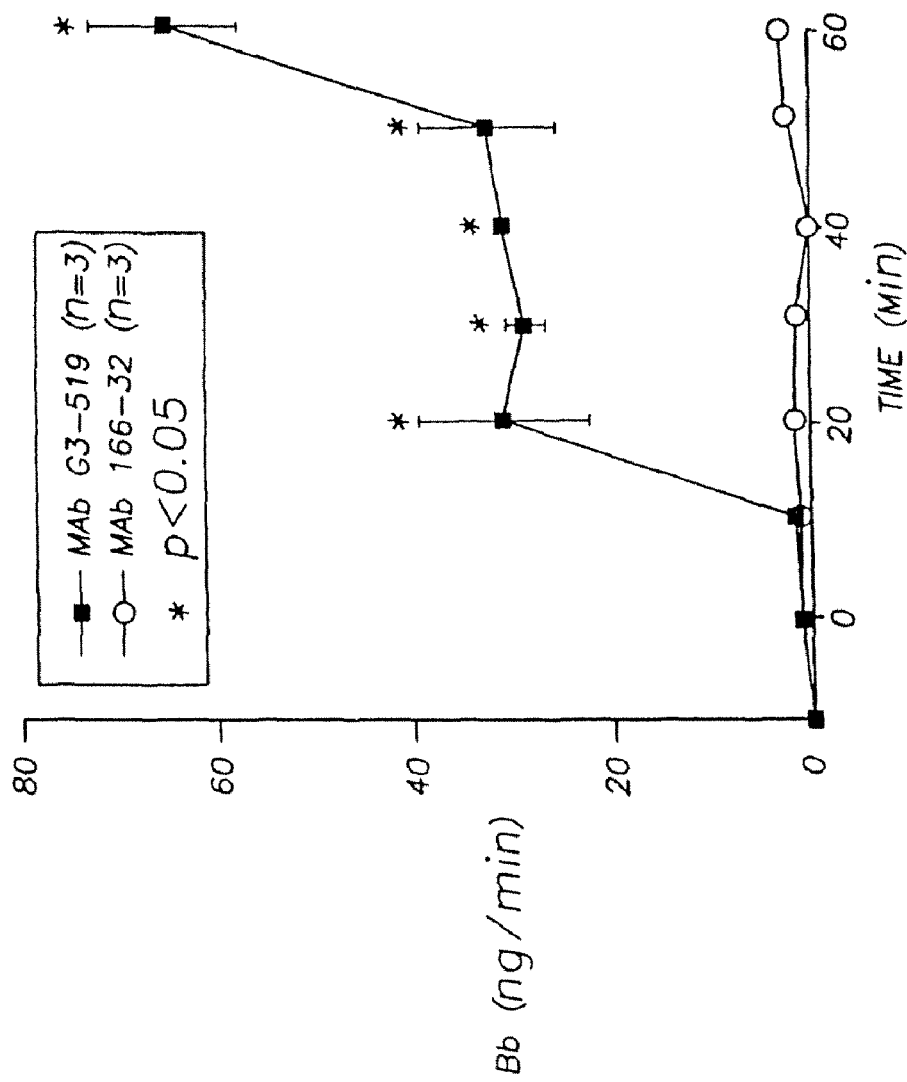
FIG. 17 shows the concentration of Bb in lymphatic effluents at selected timepoints from isolated rabbit hearts perfused with 4% human plasma. Samples from MAb 166-32 treated hearts (open circles) contained significantly less Bb than MAb G3-519 treated hearts (filled squares), p<0.05.

Ten minutes after perfusion with 4% human plasma and at every time point thereafter, a significantly ($p<0.05$) lower concentration of Bb was present in lymphatic effluents from hearts treated with MAb 166-32 as compared to hearts treated with MAb G3-519 (FIG. 17). The decrease in the production of the complement activation product Bb in the MAb 166-32 treated rabbit hearts confirms the inhibitory activity of the antibody on factor D.

4. Immunohistochemical Localization of C5b-9 Deposition:

At the completion of the protocol, hearts were removed from the Langendorff apparatus, cut into transverse sections, and frozen in liquid nitrogen. The apex and atrial tissues were discarded. Sections were embedded in O.C.T. compound embedding medium (Miles, Inc., Ekhart, Ind.), cut to 3 µm, and placed on poly-L-lysine coated slides. After rinsing with phosphate-buffered saline (PBS), sections were incubated with 4% paraformaldehyde in PBS at room temperature. Heart sections were rinsed with PBS and incubated with 1% BSA for 15 minutes to minimize non-specific staining. After rinsing with PBS, sections were incubated with a murine anti-human C5b-9 MAb (Quidel) at a 1:1,000 dilution at room temperature for 1 hour. Sections were rinsed with PBS again and then incubated at room temperature for 1 hour with a goat anti-murine FITC conjugated antibody (Sigma) at a 1:320 dilution. After a final rinse with PBS, sections were mounted with Fluoromount-G (Electron Microscopy Sciences, Fort Washington, Pa.) and protected with a coverslip. Controls included sections in which the primary antibody was omitted and sections in which an isotype-matched murine antibody IgG 1 (Sigma) was substituted for the anti-C5b-9 MAb.

Heart sections from MAb 166-32 and MAb G3-519 treated hearts were examined for human MAC (or C5b-9) deposition by immunofluorescence staining. MAb 166-32 treated hearts exhibited a reduction in MAC deposition as compared to MAb G3-519 treated hearts.

In all, the data from the ex vivo studies of rabbit hearts demonstrate the efficacy of MAb 166-32 in preventing cardiac tissue injury as a result of the inhibition of the alternative complement pathway. Inhibition of complement activation has been shown to prolong the survival of xenografts (S. C. Makrides, *Pharmacological Rev.*, 1998, 50: 59-87). Therefore, MAb 166-32 could potentially be used as a therapeutic agent to protect xenografts from destruction by human plasma.

Example 11

Inhibitory Effects of MAb 166-32 on Complement Activation and Inflammatory Reactions in an Extracorporeal Circulation Model of Cardiopulmonary Bypass (The First Pilot Study in which Human Whole Blood from Different Donors were Used for Each Individual Circuit)

Patients undergoing cardiopulmonary bypass (CPB) frequently manifest a generalized systemic inflammatory response syndrome. Clinically, these reactions are reflected in postoperative leukocytosis, fever, and extravascular fluid accumulation which may lead to prolonged recovery and occasionally with serious organ dysfunction (J. K. Kirklin et al., *J. Thorac. Cardiovasc. Surg.*, 1983; 86: 845-857; L. Nilsson et al., *Scand. J. Thorac. Cardiovasc. Surg.*, 1988; 22: 51-53; P. W. Weerwind et al., *J. Thorac. Cardiovasc. Surg.*, 1995; 110: 1633-1641). The inflammatory responses consist of humoral and cellular changes that contribute to both tissue injury and impaired hemostasis. Complement activation has been implicated as the important cause of the systemic inflammatory reaction (P. Haslam et al., *Anaesthesia*, 1980; 25: 22-26; A. Salama et al., *N. Eng. J. Med.*, 1980; 318: 408-414; J. Steinberg et al., *J. Thorac. Cardiovasc. Surg.*, 1993; 106: 1008-1016). Complement activation is attributed to the interaction between the blood and the surface of the extracorporeal circuit constituting CPB machines (D. Royston, *J. Cardiothorac. Vasc. Anesth.*, 1997; 11: 341-354). Primary inflammatory substances are generated after activation of the complement system, including the anaphylatoxins C3a and C5a, the opsonin C3b, and the membrane attack complex C5b-9. C5a has been shown to upregulate CD11b (integrin) and CD 18 (integrin) of MAC-1 complex in polymorphonuclear cells PMN (comprising mainly neutrophils) in vitro (M. P. Fletcher et al., *Am. J. Physiol.*, 1993; 265: H1750-H1761) and to induce lysosomal enzyme release by PMN. C5b-9 can induce the expression of P-selectin (CD62P) on platelets (T. Wiedmer et al., *Blood*, 1991; 78: 2880-2886), and both C5a and C5b-9 induce surface expression of P-selectin on endothelial cells (K. E. Foreman et al., *J. Clin. Invest.*, 1994; 94: 1147-1155). C3a and C5a stimulate chemotaxis of human mast cells (K. Hartmann et al., *Blood*, 1997; 89: 2868-2870) and trigger the release of histamine (Y. Kubota, *J. Dermatol.*, 1992; 19: 19-26) which induces vascular permeability (T. J. Williams, *Agents Actions*, 1983; 13: 451-455).

In vitro recirculation of whole blood in an extracorporeal bypass circuit has been used extensively as a model to simulate leukocyte (J. Kappelamyer et al., *Circ. Res.*, 1993; 72: 1075-1081; N. Moat et al., *Ann. Thorac. Surg.*, 1993; 56: 1509-1514; C. S. Rinder et al., *J. Clin. Invest.* 1995;96:1564-1572) and platelet (V. L. Jr. Hennesy et al., *Am. J. Physiol.*

1977: 2132: H622-H628; Y. Wachtfogel et al., *J. Lab. Clin. Med.*, 1985; 105: 601-607: C. S. Rinder et al., ibid) changes and complement activation (P. G. Loubser, *Perfusion.* 1987; 2: 219-222; C. S. Rinder et al., ibid; S. T. Baksaas et al., *Perfusion*, 1998; 13: 429-436) in CPB. The effectiveness of the anti-factor D MAb 166-32 to inhibit the cellular and complement activation in human whole blood was studied using this extracorporeal circulation model for CPB.

1. Extracorporeal Circuit Preparation:

Extracorporeal circuits were assembled using a hollow-fiber pediatric membrane oxygenator with an integrated heat exchanger module (D 901 LILLPUT 1; DIDECO, Mirandola (MO), Italy), a pediatric venous reservoir with an integrated cardiotomy filter (D 752 Venomidicard; DIDECO), a perfusion tubing set (Sorin Biomedical, Inc., Irvine, Calif.) and a multiflow roller pump (Stockert Instruments GmbH, Munich, Germany). Oxygenator and circuitry were primed with Plasma-Lyte 148 solution (Baxter Healthcare Corp., Deerfield, Ill.). The prime was warmed to 32° C. with a cooler-heater (Sarns; 3M Health Care, Ann Arbor, Mich.) and circulated at 500 ml/min, while the sweep gas flow was maintained at 0.25 liters per min using 100% oxygen. The sweep gas was changed to a mixture of oxygen (95%) and carbon dioxide (5%) after the blood was added to the circuit. The pH, $PCO_2$, $PO_2$, and perfusate temperature were continuously monitored throughout the recirculation period. Sodium bicarbonate was added as required to maintain pH in the range of 7.25-7.40.

2. Extracorporeal Circuit Operation and Sampling:

450 ml of blood were drawn over 5-10 minutes from healthy volunteers on no medications into a transfer pack (Haemo-Pak; Chartermed, Inc., Lakewood, N.J.) containing porcine heparin (5 units/ml, final concentration; Elkins-Sinn, Chemy Hill, N.J.) and the anti-factor D MAb 166-32 or the isotype-matched negative control MAb G3-519 (18 μg/ml final concentration). This concentration of antibody is equivalent to about 1.5 times the molar concentration of factor D in the blood. Prior to the addition of the blood to the extracorporeal circuit, a blood sample was taken from the transfer pack as the "pre-circuit" sample, designated the "−10 minute sample". The blood was then added to the reservoir via the prime port. Prime fluid was simultaneously withdrawn distal to the oxygenator outlet to yield a final circuit volume of 600 ml and a final hematocrit of 25-28%. Blood was circulated with prime, and complete mixing was accomplished within 3 minutes: a baseline sample was drawn and designated as time 0. To mimic usual procedures of surgical operation under hypothermia, the circuit was then cooled to 27° C. for 70 minutes after which it was rewarmed to 37° C. for another 50 minutes (for a total of 120 minutes of recirculation).

Blood samples were also drawn at 10, 25, 40, 55, 70, 80 and 120 minutes during the recirculation. Plasma samples were prepared by immediate centrifugation at 2,000×g at 4° C. Aliquots for the alternative pathway hemolytic assays and neutrophil-specific myeloperoxidase assays were snap-frozen on dry ice and then stored at −80° C. Aliquots for measurement of complements C3a, C4d, sC5b-9, and Bb by ELISA were immediately mixed with equal volume of a Specimen Stabilizing Medium (Quidel), snap-frozen on dry ice, and then stored at −80° C. Samples of whole blood were also collected for immunostaining of the activation cell surface markers CD11b and CD62P on neutrophils and platelets, respectively. To prevent subsequent complement activation of the whole blood samples during the staining procedure, 10 μl of 1 M EDTA were added to every ml of whole blood to give a final concentration of 10 mM.

3. Alternative Pathway Hemolytic Assays:

The alternative complement activity in the plasma samples at different time points from the MAb 166-32 treated and the MAb G3-519 treated circuits were tested using rabbit red blood cells as described above. Fifty microliters of each sample (20%) were mixed with 50 μl of GVB/Mg-EGTA buffer before addition of 30 μl of rabbit red blood cells (1.7× $10^8$ cells/ml). After incubation at 37° C. for 30 minutes, the supernatants were collected and OD read at 405 nm using an ELISA plate reader.

Figure 18:
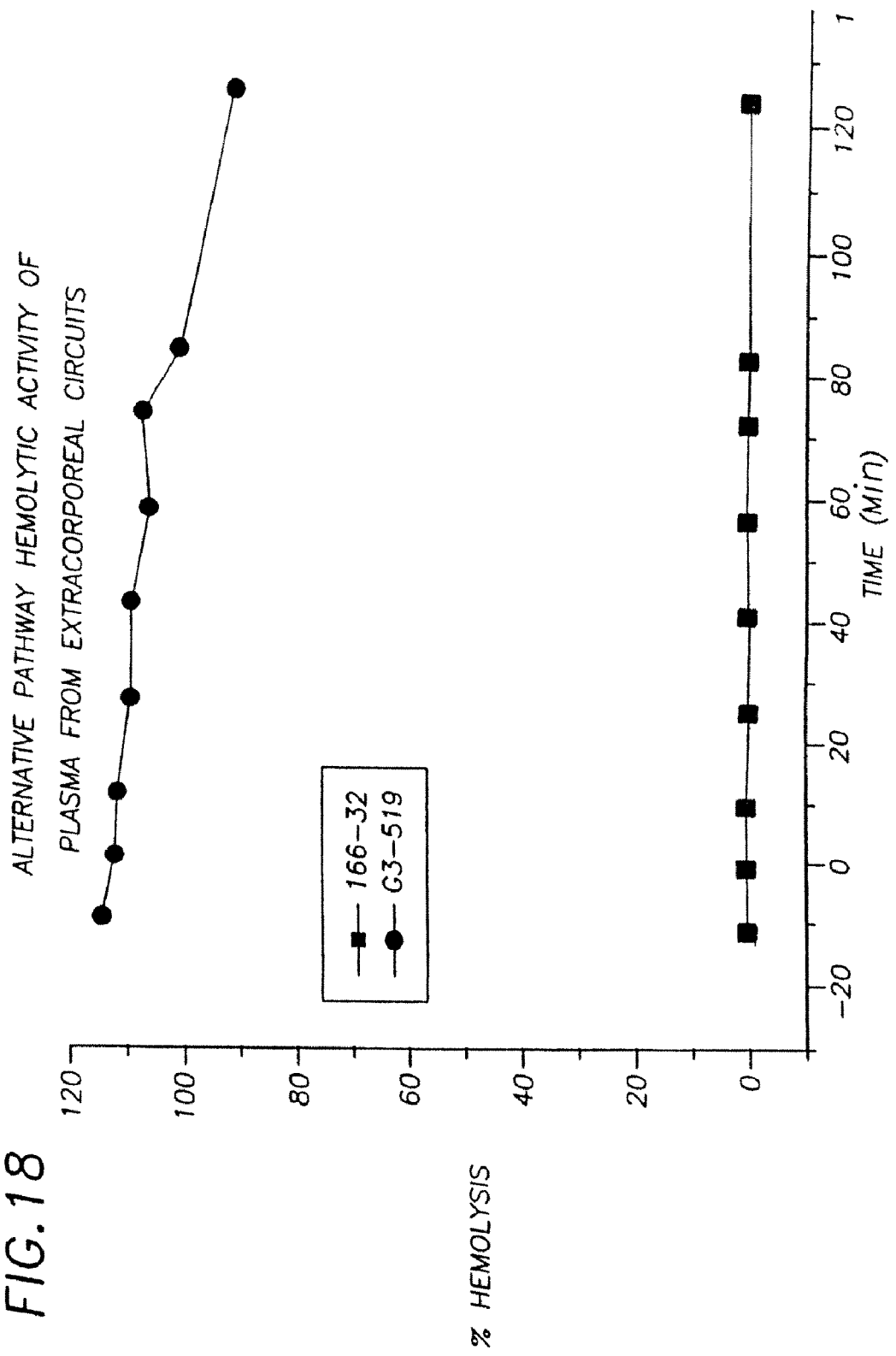
FIG. 18 shows the alternative pathway hemolytic activity of plasma samples collected at different time points from the extracorporeal circuits treated with MAb 166-32 (filled squares) or MAb G3-519 (filled circles).

FIG. 18 shows that the alternative complement activity in the MAb 166-32 treated circuit was completely inhibited by the antibody, whereas MAb G3-519 had no effect on the complement activity when used in the corresponding circuit. The results indicate MAb 166-32 is a potent inhibitor of the alternative complement pathway. Even at a molar ratio of only 1.5:1 (MAb:factor D), MAb 166-32 can completely inhibit the alternative complement activity.

4. Assays of Complement Activation Products:

In addition to the hemolytic assays described above, the plasma samples from the two extracorporeal circuits were tested for the levels of C3a, sC5b-9, Bb, and C4d. These substances were quantitated using commercially available ELISA kits (Quidel) according to the manufacturer's manuals. Like C5a, sC5b-9 is an alternative marker for C5 convertase activity in the complement cascade. Both C5a and sC5b-9 are produced as a result of cleavage of C5 by C5 convertase. Complement Bb is a specific marker for the activation of the alternative complement pathway, whereas C4d a specific marker for the activation of the classical pathway.

Figure 19:
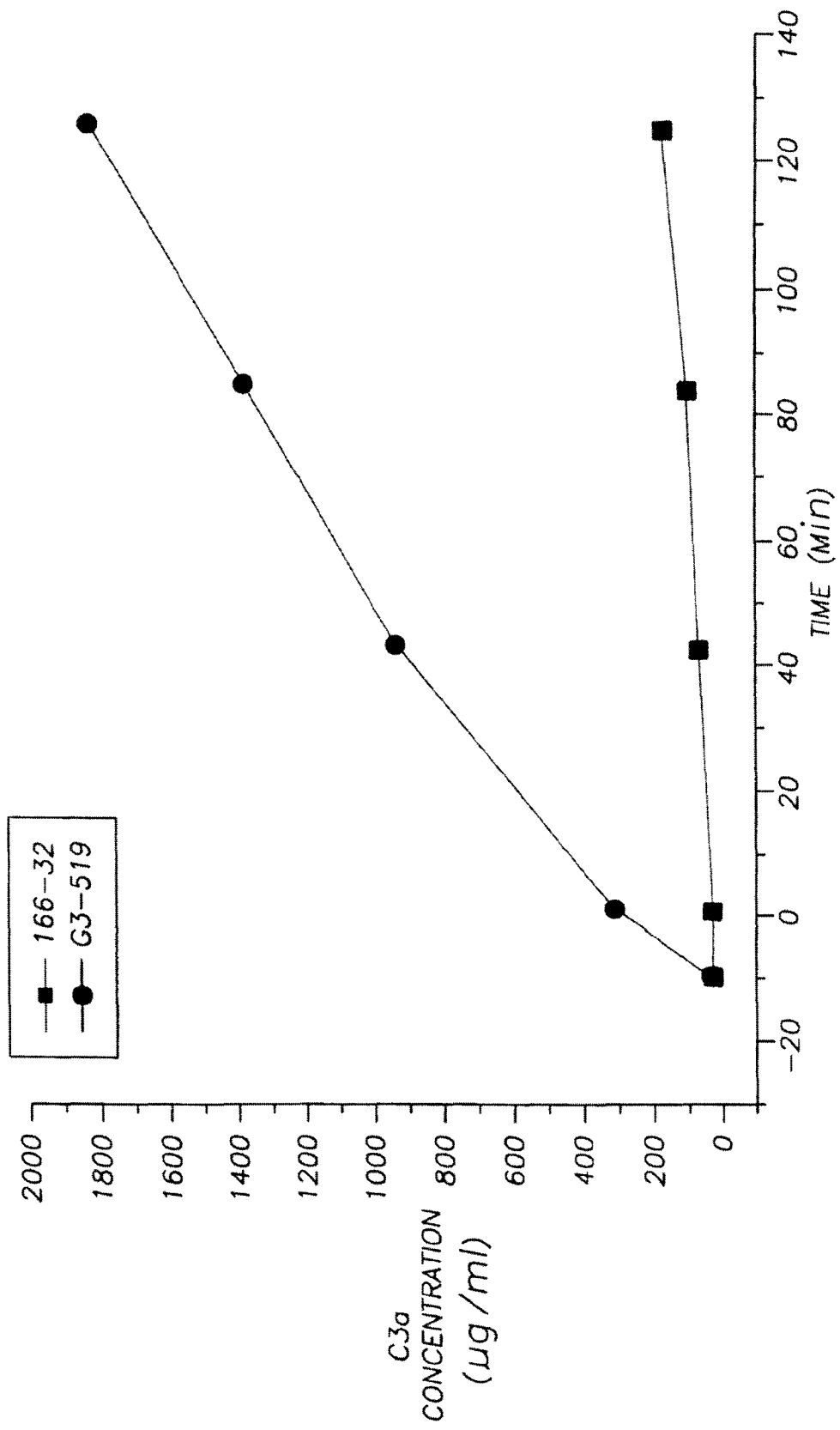
FIG. 19 shows the concentration of C3a in plasma samples collected at different time points from the extracorporeal circuits treated with MAb 166-32 (filled squares) or MAb G3-519 (filled circles).
Figure 20:
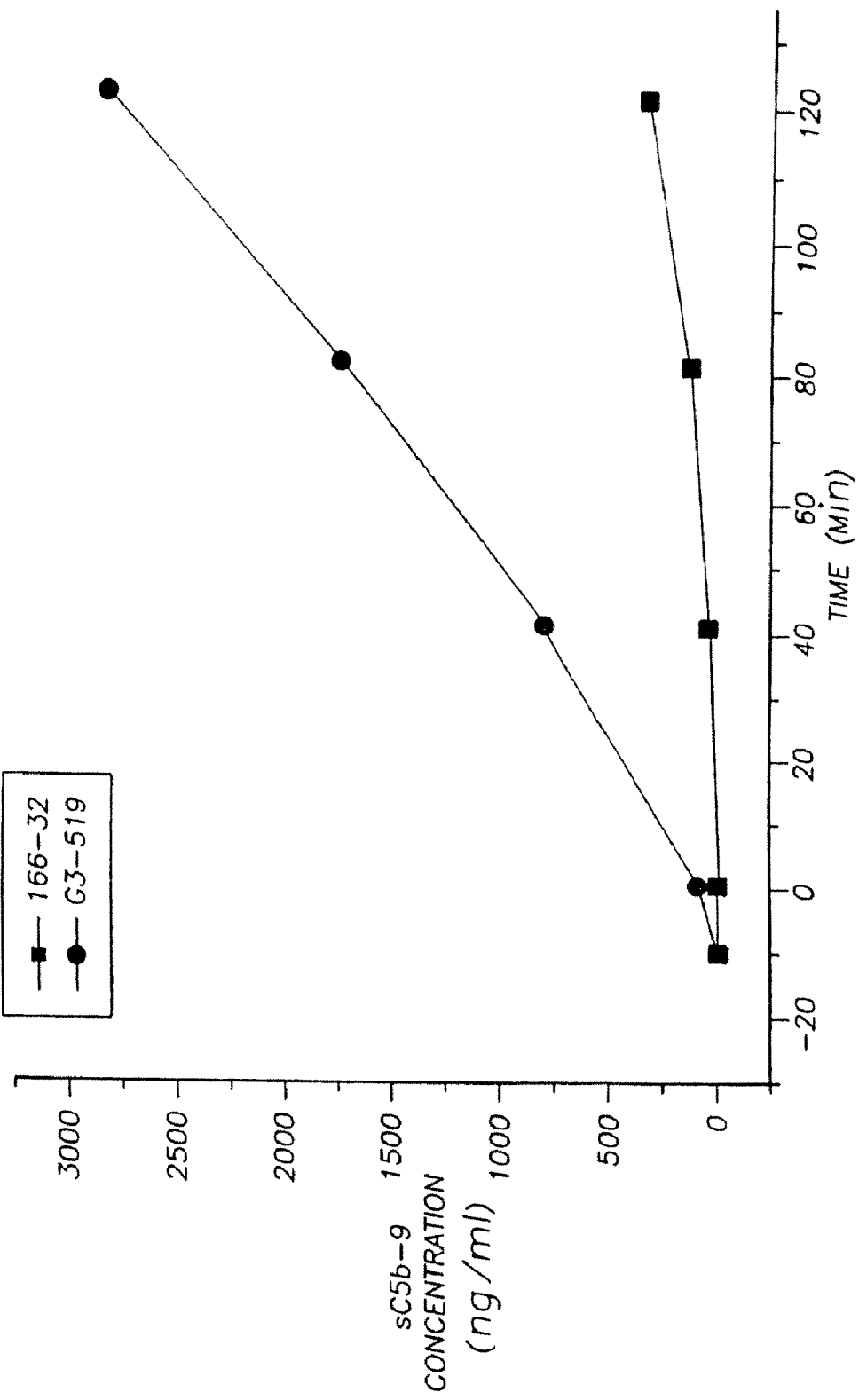
FIG. 20 shows the concentration of sC5b-9 in plasma samples collected at different time points from the extracorporeal circuits treated with MAb 166-32 (filled squares) or MAb G3-519 (filled circles).
Figure 21:
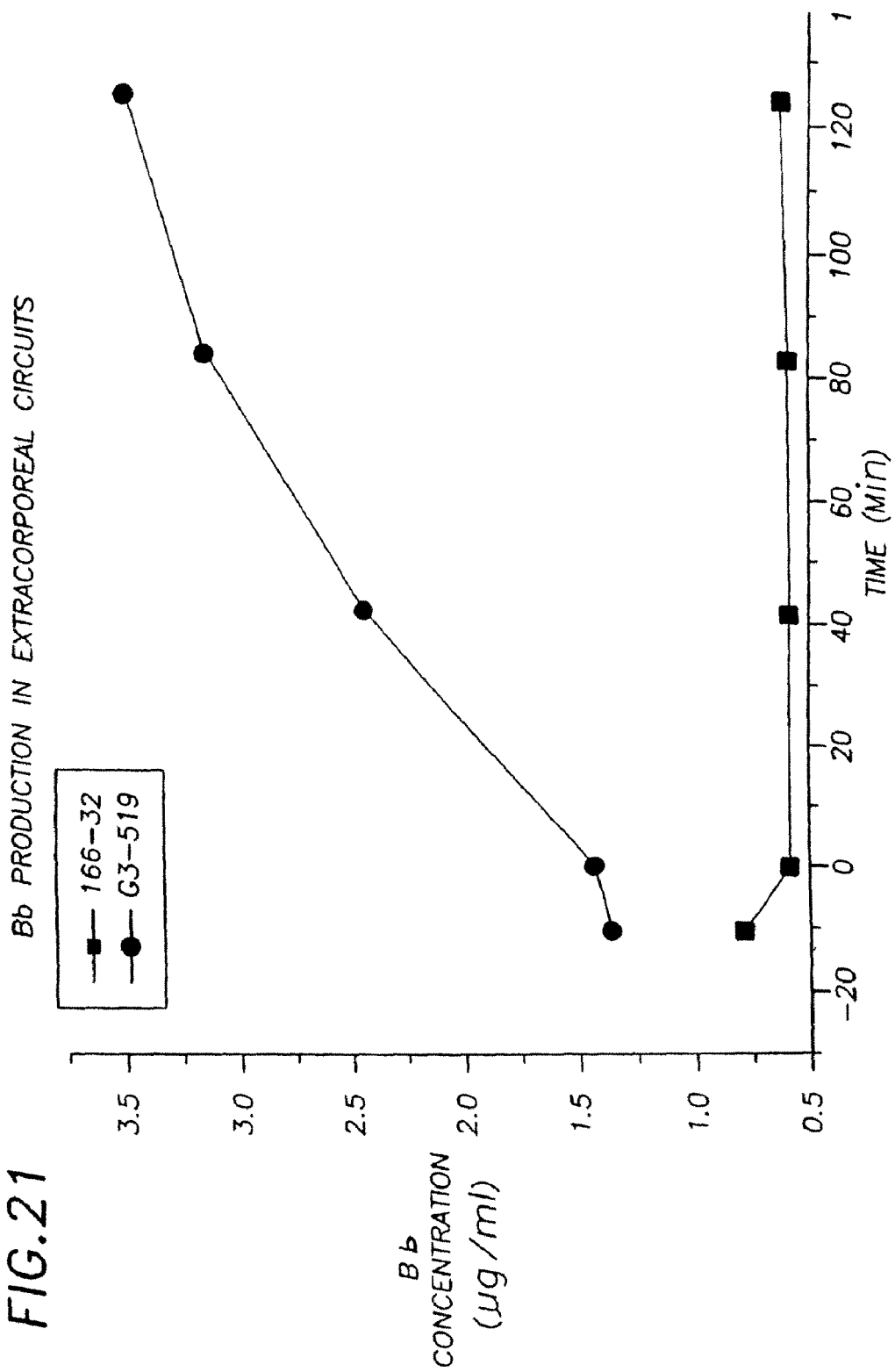
FIG. 21 shows the concentration of Bb in plasma samples collected at different time points from the extracorporeal circuits treated with MAb 166-32 (filled squares) or MAb G3-519 (filled circles).
Figure 22:
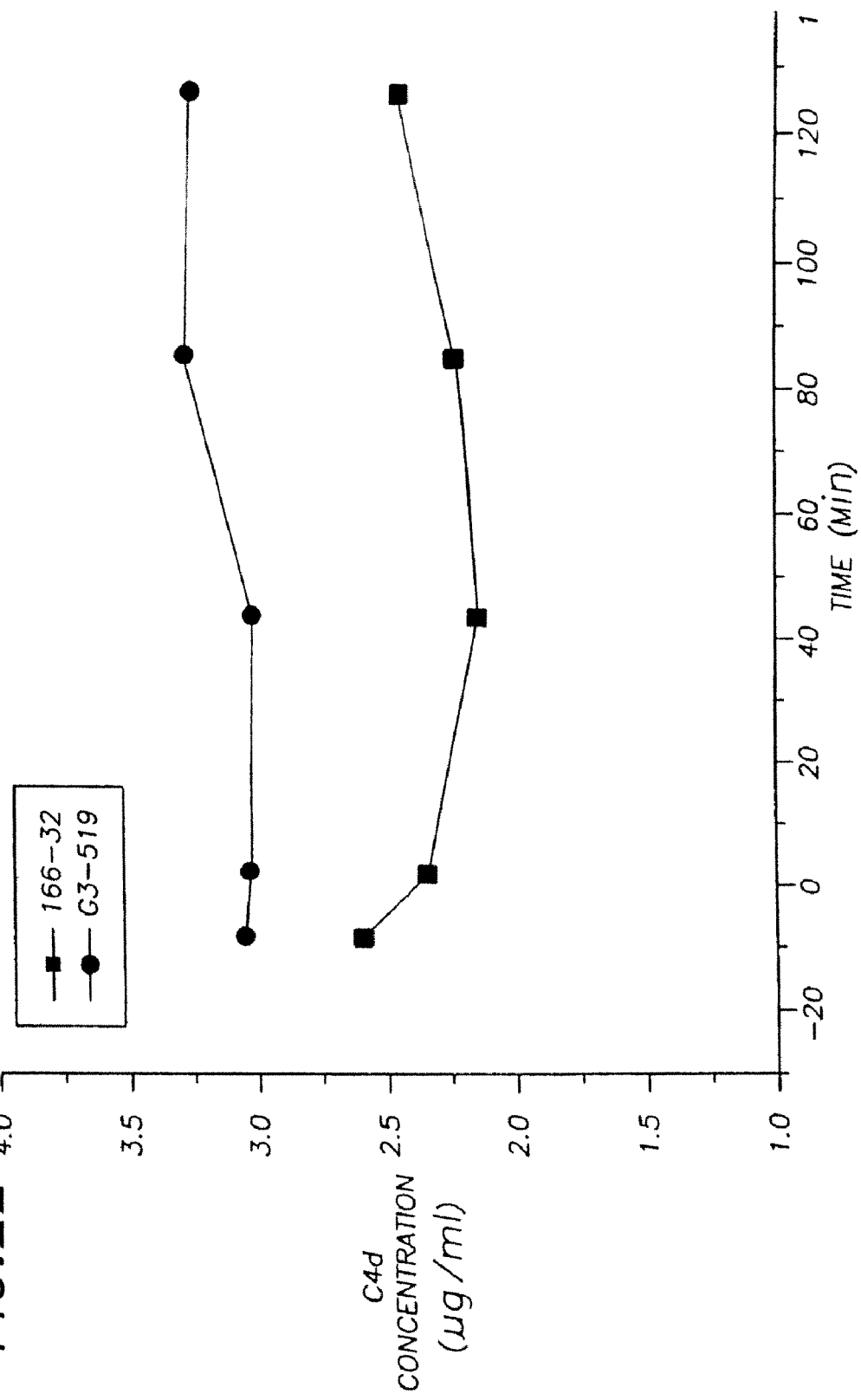
FIG. 22 shows the concentration of C4d in plasma samples collected at different time points from the extracorporeal circuits treated with MAb 166-32 (filled squares) or MAb G3-519 (filled circles).

FIGS. 19 and 20 show that MAb 166-32 inhibited effectively the production of C3a and sC5b-9 respectively, whereas the isotype-matched negative control MAb G3-519 did not. The specificity and potency of MAb 166-32 are further elucidated in FIGS. 21 and 22. The production of Bb by the alternative complement pathway was completely inhibited by MAb 166-32, whereas the levels of Bb in the G3-519 circuit increase over time during the recirculation. Interestingly, the levels of C4d in both MAb 166-32 and G3-519 circuit did not vary significantly over time. The latter results on Bb and C4d levels strongly indicate that the complement activation in extracorporeal circulation is mediated mainly via the alternative pathway.

In sum, the results indicate that MAb 166-32 is a potent inhibitor of the alternative complement pathway. Inhibition of factor D can abolish the complement activation in the subsequent steps of the cascade as manifested by the reduction in C3a and sC5b-9 formation.

5. Assays for the Activation of Neutrophils and Platelets:

The activation of neutrophils and platelets were quantitated by measuring the levels of the cell-surface expression of CD11b and CD62P on neutrophils and platelets, respectively. For CD11b labeling of neutrophils, 100 μl of whole blood collected from the circuits were immediately incubated with 20 μl of phycoerythrin (PE)-anti-CD11b antibody (clone D12, Becton Dickinson, San Jose, Calif.) for 10 minutes at room temperature in a microcentrifuge tube. Then 1.4 ml of FACS Lysing Solution (Becton Dickinson) was added for 10 minutes at room temperature to lyse red blood cells and to fix leukocytes. The microcentrifuge tubes were centrifuged at 300×g for 5 minutes. The supernatant was aspirated and the cells resuspended in PBS for washing. The microcentrifuge tubes were spun again, the supernatant aspirated, and the cells finally resuspended in 0.5 ml of 1% paraformaldehyde overnight prior to analysis using an EPIC-XL flow cytometer (Coulter Corp. Miami, Fla.). For double labeling to concomitantly identify the neutrophil population, 5 μl of fluorescein isothiocyanate (FITC)-anti-CD15 antibody (clone MMA, Becton Dickinson) were added for incubation together with PE-anti-CD11b antibody.

For CD62P labeling of platelets, 40 µl of whole blood collected from the circuits were immediately incubated with 20 µl of PE-anti-CD62P antibody (clone AC1.2, Becton Dickinson) for 10 minutes at room temperature in a microcentrifuge tube. Then the mixture was treated with FACS Lysing Solution as described above. The microcentrifuge tubes were centrifuged at 2,000×g for 5 minutes. The platelets were washed in PBS, fixed in 1% paraformaldehyde and then analyzed as described above. For double labeling to concomitantly identify the platelet population, 5 µl of FITC-anti-CD42a antibody were added for incubation together with PE-anti-CD62P antibody.

For flow cytometric measurement, the PMN (containing mainly neutrophils) and platelet populations were identified by live-gating based on forward-versus side-scatter parameters and specific staining with FITC-anti-CD15 antibody and FITC-anti-CD42a antibody, respectively. The background staining was gated using isotype-matched labeled antibodies. The intensity of expression of CD11b and CD62P was represented by mean fluorescence intensity (MFI).

Figure 23:
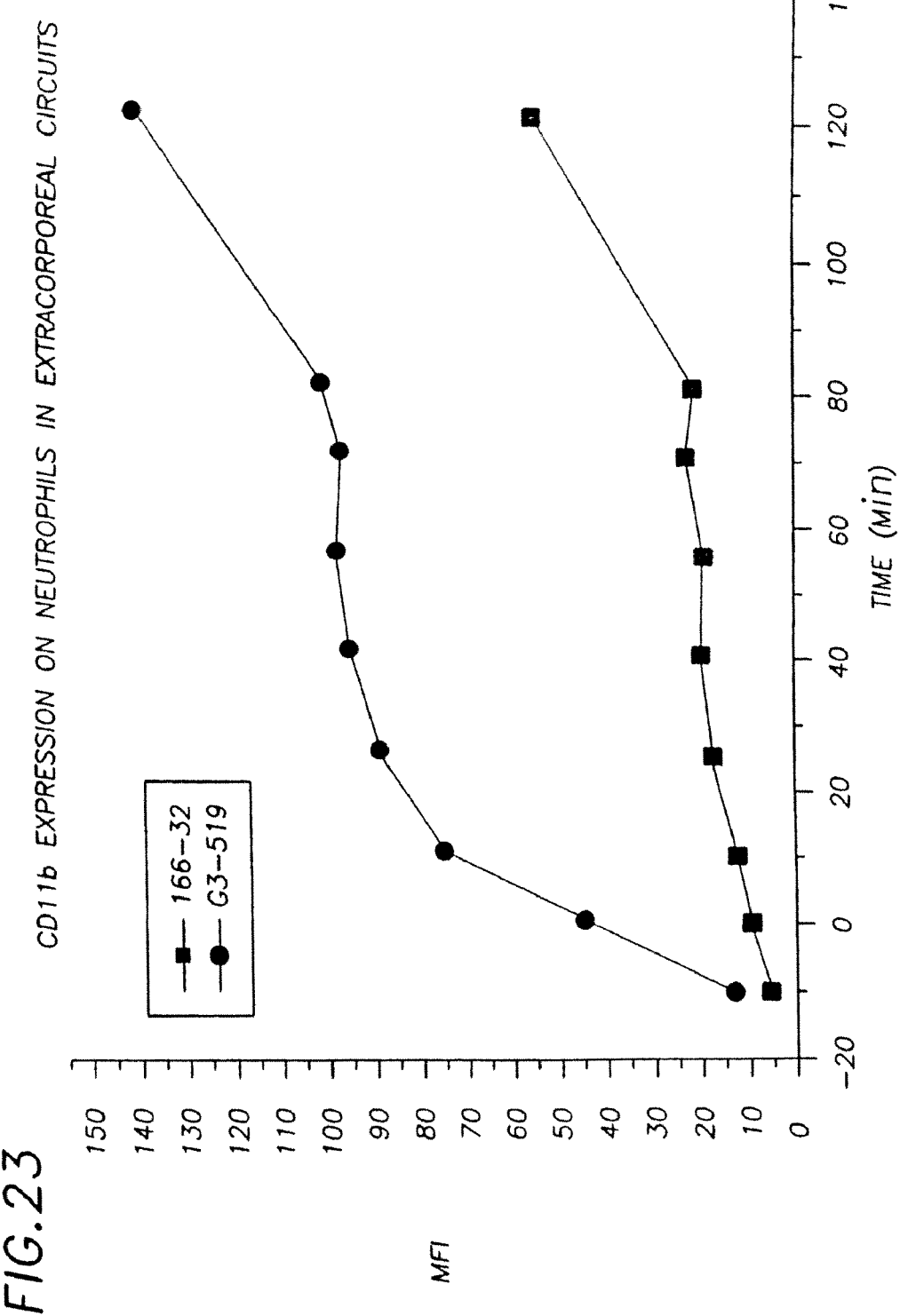
FIG. 23 shows the level of expression of CD11b on the surface of neutrophils obtained at different time points from the extracorporeal circuits treated with MAb 166-32 (filled squares) or MAb G3-519 (filled circles). The level of expression of CD11b is represented by mean fluorescence intensity (MFI) obtained by immunocytofluorometic analyses.

FIG. 23 shows that neutrophils from the MAb 166-32 treated extracorporeal circuit showed substantially lower expression of CD11b as compared to those from the MAb G3-519 treated circuit. These data together with the others above indicate that inhibition of the alternative complement activation by MAb 166-32 can prevent activation of neutrophils.

Figure 24:
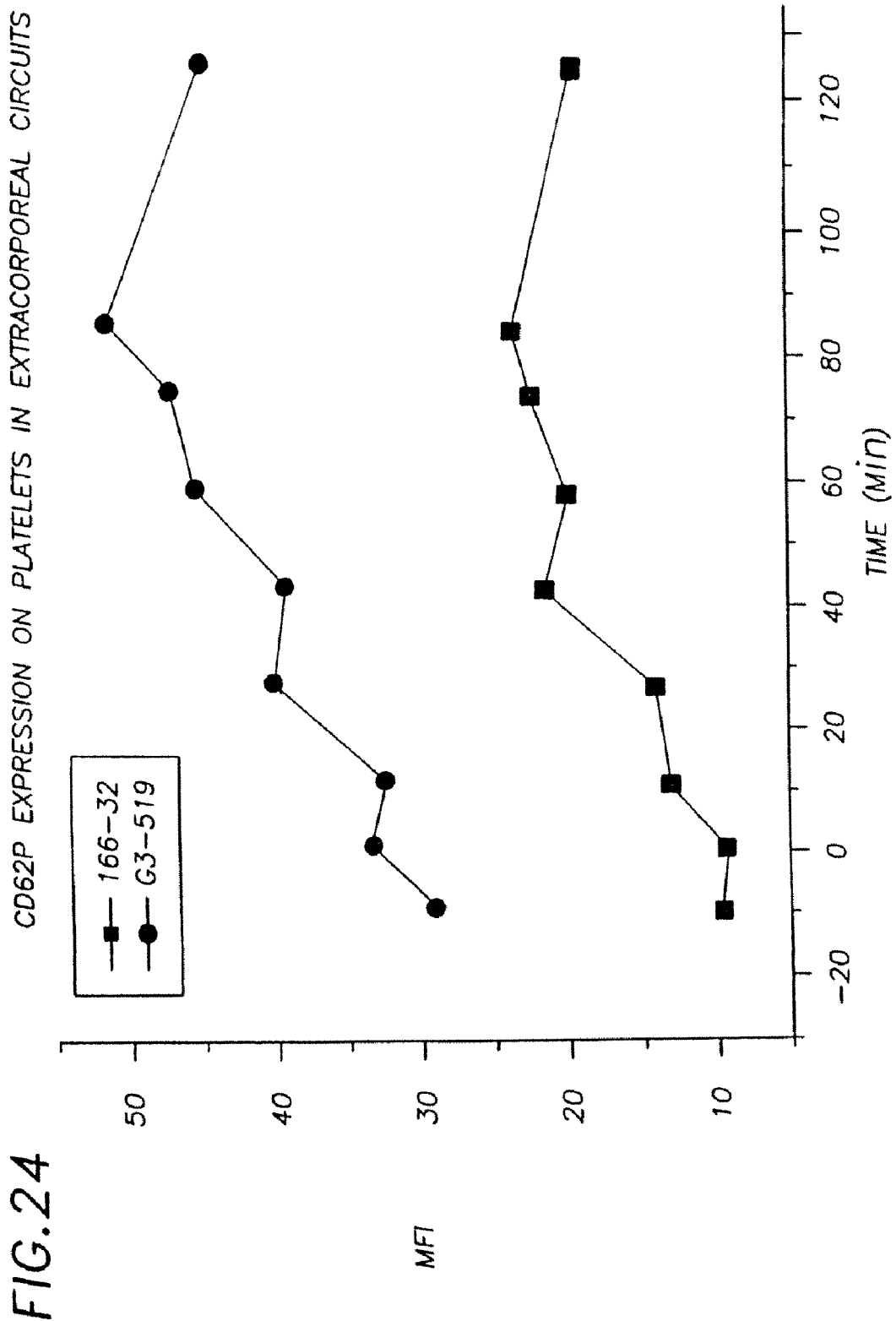
FIG. 24 shows the level of expression of CD62P on the surface of platelets obtained at different time points from the extracorporeal circuits treated with MAb 166-32 (filled squares) or MAb G3-519 (filled circles). The level of expression of CD62P is represented by mean fluorescence intensity (MFI) obtained by immunocytofluorometric analyses.

Similarly, FIG. 24 shows that platelets from the MAb 166-32 treated extracorporeal circuit showed substantially lower expression of CD62P as compared to those from the MAb G3-519 treated circuit. Again these data together with those above indicate that inhibition of the alternative complement activation by MAb 166-32 can prevent activation of platelets.

6. Assay of Neutrophil-Specific Myeloperoxidase (MPO)

The degree of activation of neutrophils was also measured using a commercial ELISA kit (R & D Systems, Inc., Minneapolis, Minn.) to quantitate the amount of neutrophil-specific myeloperoxidase (MPO) in the plasma samples from the extracorporeal circuits. MPO is stored in primary granules (azurophilic) of neutrophils. It is released when neutrophils undergo de-granulation during activation. Therefore MPO is a soluble marker for neutrophil activation. The assays were performed according to the manufacturer's manual. Briefly, samples were incubated in the cells of a microplate, which have been coated with a first MAb to MPO. The MPO-MAb complex is labeled with a biotin-linked polyclonal antibody prepared from goat MPO-antisera. The final step of the assay is based on a biotin-avidin coupling in which avidin has been covalently linked to alkaline phosphatase.

The amount of MPO in each sample is enzymatically measured upon addition of the substrate 4-nitrophenyl-phosphate (pNPP), by reading OD at 405 nm.

Figure 25:
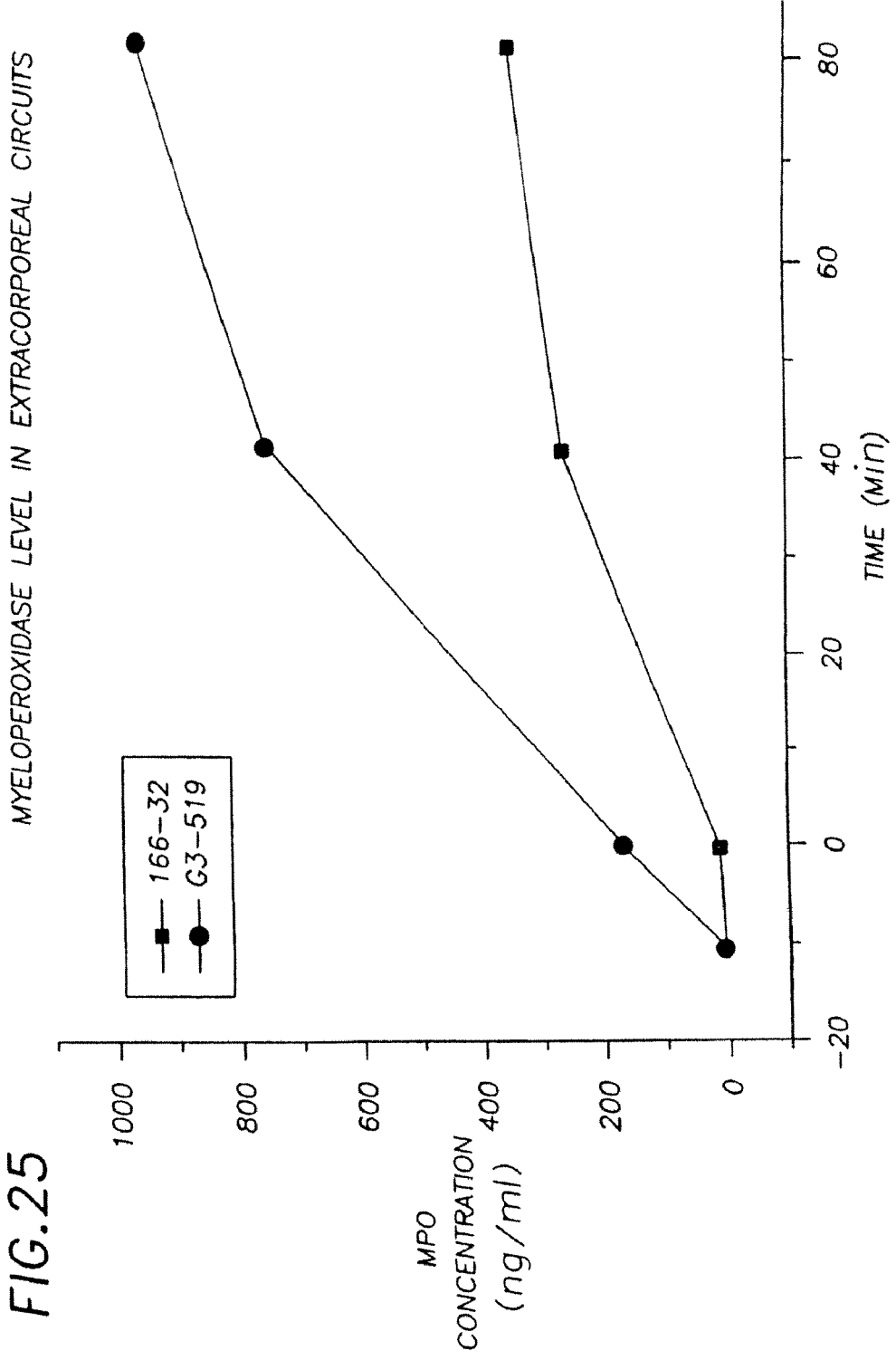
FIG. 25 shows the concentration of neutrophil-specific myeloperoxidase (MPO) in plasma samples collected at different time points from the extracorporeal circuits treated with MAb 166-32 (filled squares) or MAb G3-519 (filled circles).

FIG. 25 shows that the levels of MPO in the MAb 166-32 treated circuit were substantially lower than those in the MAb G3-519 circuit. The results corroborate with those on the expression of CD11b in the immunofluorometric studies described above.

Taken together, the data on complement, neutrophils and platelets support the notion that effective inhibition of the alternative complement activation in extracorporeal circulation by the anti-factor D MAb 166-32 can abolish the formation of inflammatory substances C3a, C5a and sC5b-9 and thus reduce the activation of neutrophils and platelets. It is anticipated that MAb 166-32, as well as its fragments, homologues, analogues and small molecule counterparts thereof, will be effective in preventing or reducing clinical inflammatory reactions caused by CPB.

Example 12

Inhibitory Effects of Mab 166-32 on Complement Activation and Inflammatory Reactions in an Extracorporeal Circulation Model of Cardiopulmonary Bypass (A Modified Study in which Whole Blood from the Same Donor was Used in Both Mab 166-32 and Mab G3-519 (Negative Control) Circuits on the Same Day)

1. Experimental Design and Methods

In order to avoid any variations in complement activity in the blood from different donor, we modified the study design described in Example 11. In this modified protocol, whole blood from the same donor was used in both MAb 166-32 and MAb G3-519 circuits on the same day.

In the study, whole blood was obtained from 5 healthy for five paired (test and control) circuits. Anti-factor D MAb 166-32 (4.5 mg) was added to 250 ml of freshly collected, heparinized human whole blood to give a final concentration of 18 µg/ml (equivalent to about 1.5 times the molar concentration of human factor D in the blood). MAb G3-519 was added at the same final concentration to another 250 ml of heparinized whole blood from the same donor on the same day for a parallel circuit. The blood was then added to an extracorporeal circuit consisting of a hollow-fiber pediatric membrane oxygenator. The circuit was primed with lactated Ringer's solution which was circulated at 500 ml/minute. The initial volume of the diluted blood in the circuit was 350 ml. The hematocrit was maintained at 26-28%. To simulate hypothermic CPB commonly performed in open-heart surgery, the re-circulated blood was maintained at 27° C. for the initial 70 minutes; the circuits were re-warmed to 37° C. at 80 minutes. The temperature was maintained until 120 min.

Blood samples were collected at different time points during the re-circulation. Complement activation products (Bb, C4d, C3a, and sC5b-9), CD11b expression on neutrophils, CD62P expression on platelets, and neutrophil-specific myeloperoxidase were measured by the methods described in Example 11.

C5a was also measured quantitatively by an ELISA. Briefly, eight microliters of 1 M EDTA was added to eighty microliters of human plasma in an Eppendorf microfuge tube to prevent complement activation. Then 88 µl of a precipitating reagent (Amersham, Arlington Heights, Ill.) was added to the sample for incubation at room temperature for 30 minute. This procedure would precipitate high molecular weight proteins including C5. The mixture was then centrifuged at 15,000×g for 15 minutes at 4° C. For the C5a ELISA, protein A purified rabbit anti-C5a polyclonal antibodies (Calbiochem, La Jolla, Calif.) was used to coat wells of 96-well microtest plates to capture C5a in plasma, whereas purified sheep anti-C5 polyclonal antibodies (Biodesign, Kennebunk, Me.) was used for detection. The bound sheep antibodies were detected by HRP-conjugated rabbit anti-sheep IgG (Fc) antibodies (Jackson ImmunoResearch). Purified C5a (Advanced Research Technologies) was used as standard for calibration. In the assays, each well of 96-well microtest plates was incubated with 100 µl of rabbit anti-C5a antibodies (2 µg/ml) overnight at room temperature. After the solution was removed, the remaining binding sites in the wells of the plastic plates were saturated by incubation with 200 µl of PBSTB for 1 hour as described above. The wells were then washed with PBST. Treated plasma at serial dilutions was added to the wells in duplicates for 1 hour at room temperature. The wells were then washed again. One hundred µl of sheep anti-human C5 antibodies at 5 µg/ml was added to the well for 1 hour at room temperature. The wells were then washed again. Then 100 µl of diluted HRP-rabbit anti-sheep IgG(Fc) antibodies were added for 1 hour at room temperature. After the wells were washed, peroxidase substrate solution was added for color development and $OD_{450}$ was measured as described above.

A quantitative ELISA developed at Tanox was used to measure neutrophil specific elastase-α1-antitrypsin complex. Upon activation, neutrophil release elastase which is immediately complexed with α1-antitrypsin inhibitor in the blood. The assay used sheep anti-human neutrophil elastase polyclonal antibodies (Biodesign) to immobilize the complex and HRP-conjugated sheep anti-α1-antitrypsin inhibitor polyclonal antibodies (Biodesign) for detection. For a calibration standard, the elastase/a1-antitrypsin inhibitor complexes were made by mixing neutrophil-specific elastase (Elastin Products Company, Inc., Owensville, Mo.) with α1-antitrypsin inhibitor (Calbiochem) at a ratio of 1:1 (w/w). In the ELISA, 100 µl of sheep anti-human neutrophil elastase (5 µg/ml) was added to each well of 96-well microtest plates for incubation overnight at room temperature. After the solution was removed, the remaining binding sites on the plastic wells were saturated by incubation with 200 µl of PBSTB for one hour at room temperature. The wells were then washed. One hundred µl of serially diluted plasma samples was added to each in duplicate for incubation for µl hour at room temperature. After the wells were washed, 100 µl of HRP-conjugated sheep anti-a1-antitrypsin inhibitor antibodies (diluted at 1:2, 000) were added to each well for 1 hour at room temperature. The wells were then washed and peroxidase substrate solution was added to the well for color development. $OD_{450}$ was then measured as described previously.

A quantitative ELISA was used to measure platelet thrombospondin which is a soluble marker for platelet de-granulation upon activation. In the assay, thrombospondin was captured by monoclonal anti-thrombospondin (clone P12) (Coulter) and then detected by biotinylated monoclonal anti-thrombospondin (clone 10) (Coulter) as described (A. E. Fiane et al. *Immunopharmacol.*, 1999; 42: 231-243). Briefly, 100 µl of monoclonal anti-thrombospondin (clone P12) at 2 µg/ml was added to each well of 96-well microtest plates for overnight at room temperature. After the solution was removed, non-specific binding sites on the plastic wells were saturated by incubation with 200 µl of PBSTB for 1 hour at room temperature. After the wells were washed, 100 µl of serially diluted plasma were added to each well in duplicate. The wells were then washed. One hundred µl biotinylated monoclonal anti-thrombospondin (clone P10) at 1 mg/ml were added to each well for 1 hour at room temperature. The wells were then washed. One hundred µl of streptavidin-conjugated HRP (Jackson ImmunoResearch) was added to each well for 1 hour at room temperature. After the wells were washed, peroxidase substrate solution was added for color development and OD450 was measured as described above. Purified thrombospondin (Calbiochem) was used as for a calibration standard in the assay.

IL-8 was measured by an ELISA kit (R & D Systems). IL-8, a proinflammatory cytokine, is produced by neutrophils, monocytes/macrophages, and T cells upon activation by anaphylatoxins.

The data from 5 paired circuits were statistically analyzed using 2-factor ANOVA of factorial, randomized block design. The data were represented as mean±standard error.

2. Results and Conclusions

MAb 166-32 at 18 µg/ml inhibited completely the alternative complement activity measured by a hemolytic assay using unsensitized rabbit RBCs, whereas the negative control Mab G3-519 had no effect (FIG. 26). On the other hand, MAb 166-32 did not inhibit the classical pathway hemolysis of sensitized sheep RBCs. The selective inhibition of the alternative complement pathway is in agreement with the complete inhibition of the production of Bb (FIG. 27). Bb is the enzymatic product of factor B activation specific to the alternative complement pathway. On the other hand, there was an increase in the plasma concentration of C4d in both circuits treated with either MAb 166-32 or G3-519 (FIG. 28). C4d is a specific marker for activation of the classical complement pathway.

The plasma concentrations of C3a, sC5b-9 and C5a in the extracorporeal circuits were also measured. MAb 166-32 strongly inhibited the production of these substances (FIGS. 29, 30 and 31). Since the alternative complement activity of the plasma in the test circuits was completely inhibited by MAb 166-32. the production of C3a, sC5b-9 and C5a in these circuits could be attributed to some activation of the classical pathway as indicated by the elevation of plasma C4d (FIG. 28). Activation of the classical pathway in extracorporeal circuits could be triggered by contact activation of the intrinsic coagulation pathway (T. E. Mollnes, *Vox. Sang.*, 1998; 74 Suppl.2: 303-307). As a result, factor X11a is released and binds C1-INH, an endogenous inhibitor of C1. When the plasma concentration of C1-INH is reduced, C1 is more susceptible to activation and thus augments the classical complement pathway. Inasmuch as the production of C5a and sC5b-9 were substantially inhibited as compared to C3a, the moderate activation of the classical pathway as described above did not seem to effectively activate C5 in this system. This is in agreement with the findings that the alternative complement pathway is predominantly activated in CPB (J. K. Kirklin et al., *J. Thorac. Cardiovasc. Surg.*, 1983; 86: 845-857). Similarly although protamine neutralization of heparin after CPB causes activation of the classical complement pathway, the activation of C5 by protamine/heparin complexes is not very effective (J. K. Kirklin et al., *Ann. Thorac. Surg.*, 1986:41: 193-199).

Activation of neutrophils as manifested by upregulation of surface expression of CD11b was measured by immunocytofluorometric analyses. The expression of CD11b on neutrophils in circuits treated with MAb 166-32 was significantly reduced as compared to the negative control MAb G3-519 (FIG. 32). Reduction of CD11b expression on neutrophils will prevent the adhesion of neutrophils to platelets and endothelial cells via the interaction with CD62P(P-selectin), an important hallmark of neutrophil-mediated inflammation (C. Rinder et al., *Blood,* 1992; 79: 1201-1205).

The activation of neutrophils was also studied by measuring the levels of neutrophil-specific myeloperoxidase and elastase in plasma. Myeloperoxidase is stored in primary granules (azurophilic) of neutrophils and released upon de-granulation of activated neutrophils. Myeloperoxidase is responsible for production of hypochlorous acid (HOCl), a powerful oxidant that could cause tissue damage. Neutrophil-specific elastase is also released upon de-granulation of activated neutrophils. The elastase could cause tissue injury as a result of hydrolysis of elastin in extracellular matrices. Consistent with the inhibition of neutrophil activation (FIG. 32), the release of both myeloperoxidase and elastase was also significantly inhibited by MAb 166-32 in the extracorporeal circuits (FIGS. 33 and 34).

The activation of platelets was inhibited by MAb 166-32 treatment of the extracorporeal circuits. The number of platelets expressing CD62P and the level of CD62P expression level on platelets were significantly reduced, respectively (FIGS. 35 and 36). The inhibition of platelet activation in MAb 166-32 treated circuits is also manifested by the reduction in thrombospondin release from activated platelets (FIG. 37).

To further study the relationship between complement activation and inflammatory responses in whole blood, we examined the plasma levels of pro-inflammatory cytokine IL-8 in the circuits. The treatment of human whole blood with MAb 166-32 reduced IL-8 production (FIG. 38). IL-8 is produced predominantly by activated neutrophils, monocytes/macrophages and T cells. IL-8 is closely associated with inflammatory diseases and CPB (M. C. Diago et al., *Acta Anaesthesiol. Scand.*, 1997; 41: 725-730; S. S. Ashraf et al., *J. Cardiothorac. Vasco. Anesthes.*, 1997; 11: 718-722). IL-8 causes chemotaxis of neutrophils, T cells and basophils, degranulation of neutrophils, and adhesion of neutrophils to endothelial cells.

Taken together, the results of the extracorporeal circulation studies both in Examples 11 and 12 show that complement activation plays important roles in inducing a plethora of cellular and humoral inflammatory responses. Anti-factor D MAb 166-32 is effective in inhibiting these inflammatory responses in our study. Therefore complete inhibition of the alternative pathway complement by Mab 166-32 could be beneficial to patients undergoing CPB.

Example 13

Study of the Effects of MAb 166-32 in a Dog Model of Ischemia and Reperfusion Injury A study was designed to examine whether MAb 166-32 would protect myocardial tissues from injury due to ischemia and reperfusion in dogs, although it was recognized at the outset that dog might not be a desirable animal model to study this indication for MAb 166-32. The ability of MAb 166-32 to neutralize dog factor D in hemolytic assays was at least 10 times less effective as compared to human factor D (see Example 7). Because of the limited amount of MAb 166-32 available at the time, MAb 166-32 was administered into the heart via the intracoronary blood vessel. It was hoped that the antibody would build up a concentration of at least 60 µg/ml in the coronary blood in order to inhibit completely dog factor D in the heart. The dosage was calculated to be 3.15 mg/kg/ infusion for 6 infusions. MAb G3-519 was used as the isotype-matched control in the study.

Briefly, purpose-bred hound dogs were anaesthetized. A left thoracotomy was performed at the fourth intercostal space to expose the heart. The proximal left circumflex coronary artery was isolated and ligated for 90 minutes for induction of ischemia that was followed by 6 hours of reperfusion. The antibody was given 6 times at 30 minutes before ischemia, 10 minutes before reperfusion, and then 75, 150, 225, 300 minutes during reperfusion. Radioactive microspheres were injected at different time points to measure regional blood flow. At the end of the experiments, hearts were perfused with Evans blue dye and triphenyltetrazolium for measurement of area at risk and infarct size, respectively. Coronary lymph and whole blood from the jugular vein were collected before ischemia and at the end of the experiment. These samples were used to measure the concentration of the injected antibodies and alternative pathway hemolytic activity.

The results show that the highest achievable concentration of MAb 166-32 in the coronary lymph was about 30 µg/ml, which is well below the concentration required for complete inhibition of dog factor D in the coronary circulation. The antibody was also detected in the systemic circulation, suggesting that the injected antibody dissipated outside of the heart. The data from the hemolytic assays show that alternative complement activity was not reduced; as is consistent with the fact that the concentration of the antibody was low. Therefore, it is not possible to draw a conclusion on the effect of MAb 166-32 in reperfusion from these experiments in dogs.

The foregoing description, terms, expressions and examples are exemplary only and not limiting. The invention includes all equivalents of the foregoing embodiments, both known and unknown. The invention is limited only by the claims which follow and not by any statement in any other portion of this document or in any other source.

Example 14

Effects of Mab 166-32 in Baboons Undergoing Cardiopulmonary Bypass

Anti-factor D Mab 166-32 (murine antibody) was studied in a baboon model of hypothermic cardiopulmonary bypass (CPB) for pharmacokinetics and for its inhibitory effects on complement, neutrophils, monocytes, platelets, and tissue injury. Baboons was selected as the animal model because they have been extensively used as a non-human primate model in CPB studies (Hiramatsu Y et al., J. Lab. Clin. Med. 1997; 130: 412-420; Gikakis N et al., J. Thorac. Cardiovasc. Surg. 1998; 116: 1043-1051) and Mab 166-32 is equally effective at inhibiting baboon factor D and human factor D.

Fourteen healthy adult baboons (ca. 15 kg of body weight) were used in the study. The baboons were pre-screened for negative serological reactivity with Mab 166-32 by ELISA. The baboons were assigned to two groups: 7 in the Mab 166-32-treated group and 7 in a saline-control group. Baboons in the treatment group received a single intravenous bolus injection of Mab 166-32 at 5 mg/kg, whereas baboons in the control group received an equal volume of saline. This dosage of Mab 166-32 was chosen because it was estimated to be adequate to completely neutralize the factor D for about 7 hours, based on previously obtained data that Mab 166-32 at 1 mg/kg completely inhibited factor D in rhesus monkeys for at least 1.5 hours. Mab 166-32 inhibited baboon, monkey and human factor D equally well.

Baboons were sedated with an intramuscular injection of 10 mg/kg of ketamine hydrochloride, and anesthesia was induced with 5 mg/kg of thiopental sodium. The animals were then intubated, and general anesthesia was maintained with inhaled isoflurane.

Heparin (300 units/kg) was administered for anti-coagulation. After a median sternotomy was performed, the ascending aorta and the right atrium were cannulated with a 14-French aortic cannular (DLP, Inc. Grand Rapids, Mich., USA) and a 26-French single-stage venous cannula (Polystan A/S, Varlose, Denmark), respectively. Lactated Ringer's solution was then used to prime the extracorporeal circuit. The priming volume for the whole circuit was approximately 600 ml. This particular low-prime circuit was used to avoid the need for donor blood. During the CPB, the hematocrit was maintained at 26% to 28%. Pulmonary artery flow was assessed with a 12-mm perivascular flow probe (Transonic Systems, Ithaca, N.Y., USA), before and after CPB, for cardiac output measurements.

The CPB circuit consisted of a conventional non-pulsatile roller pump (Stockert, Irvine, Calif., USA), a hollow-fiber membrane oxygenator (Capiorx SX10; Terumo Corp., Tokyo, Japan), an arterial filter (Terumo Corp.), and silicone elastomer tubing (Dow Corning, Inc., Midland, Mich., USA). The pump flow rate was maintained at 80 ml/kg/min. During CPB, the mean arterial pressure was maintained at 50-60 mm Hg by adding isoflurane through the oxygenator inflow conduit. At the end of CPB, protamine (1 mg/100 units of heparin) was administered for heparin neutralization. The heart rate, systemic arterial pressure, central venous pressure, and pulmonary arterial pressure was continuously monitored. At the end of the experiment, each animal was euthanized with intravenous boluses of Beuthanasia-D (0.22 mg/kg).

Blood samples were taken from the animals for assays at different time points: Before injection of Mab 166-32 or saline (at 0 hour), after injection of Mab 166-32 or saline (at 45 minutes), before CPB (at 1 hour), 10 minutes in CPB at 37° C., 25 minutes in CPB at 27° C., 85 minutes in CPB at 27° C., 105 minutes in CPB at 37° C. after re-warming, 135 minutes in CPB at 37° C. prior to protamine administration (at 3.25 hours), 30 minutes after CPB at 37° C., 1 hour after CPB at 37° C., 2 hours after CPB at 37° C., 6 hours after CPB at 37° C. (at 9.25 hours), and finally 18 hours after CPB at 37° C. (at 21.25 hours). Experiments with 8 of the 14 baboons (4 in the treatment group and 4 in the control group) were terminated at 6 hours after CPB, whereas the remaining animals (3 in the treatment group and 3 in the control group) were terminated 18 hours after CPB.

Plasma and whole blood samples were used in different assays to measure:
  a. Plasma concentration of free Mab 166-32 by ELISA using factor D as the coating antigen;
  b. Functional activity of factor D in baboon plasma as determined by two hemolytic assays: rabbit red blood cells for the alternative complement pathway and sensitized chicken red blood cells for the classical complement pathway;
  c. Plasma concentration of complement Bb, C4d, and C3a by ELISA (Quidel Corp., San Diego, Calif., USA);
  d. Expression level of CD11b on neutrophils and monocytes by immunofluorocytometric methods;
  e. Expression level of CD62P on platelets by immunofluorocytometric methods;
  f. Plasma concentration of IL-6 by ELISA (BioSource International, Inc., Camarillo, Calif., USA); and
  g. Plasma concentration of lactate dehydrogenase (LDH), creatine kinase (CK), creatine kinase MB isoenzymes (CK-MB), and creatinine.

The data were analyzed statistically by student's T-test (for C4d) and 2-way ANOVA of repeated measurements (for other parameters) (significant at $p<0.05$). The data were represented as mean±SEM.

Results and Discussion

In this study, baboons were treated with a single intravenous bolus injection of 5 mg/kg of Mab 166-32. The plasma concentrations of the free antibody were measured by an ELISA using human factor D as coating antigen (FIG. 39). At 45 minutes after the antibody injection, the plasma concentration of free Mab 166-32 was 68.3±9.9 µg/ml. The antibody concentration then decreased to 23.4±4.4 µg/ml at 10 minutes after CPB, as a result of hemodilution upon the initiation of CPB. The antibody concentration remained at 10-13 µg/ml until 3 hours after CPB. The antibody concentration reduced to 6.2±2.3 µg/ml at 6 hours after CPB and to 1.7±3.9 µg/ml at 18 hours after CPB.

Using an alternative complement hemolytic assay with rabbit red blood cells, the functional activity of factor D in the plasma samples from the Mab166-32 treated animals was measured (FIG. 40). The alternative complement hemolytic activity of the baboon plasma samples was completely inhibited at 6 hours after CPB. At 18 hours after CPB, the inhibition was reduced to 79.3±10%. The data are consistent with the presence of free Mab 166-32 in the circulation until 18 hours after CPB (FIG. 39). In hemolytic assays using sensitized chicken red blood cells to measure the classical complement activity, the corresponding plasma samples from the Mab 166-32 treated animals did not show any reduction in the classical complement activity by the antibody (FIG. 40). These results confirm that Mab 166-32 is a specific inhibitor of the alternative complement pathway.

The specificity of Mab 166-32 in inhibiting the alternative complement pathway was also demonstrated by the complete inhibition of Bb formation (FIG. 41). Bb is the activation product of factor B upon proteolytic cleavage by factor D. The increase in Bb formation in the control animals is attributed to the activation of the alternative complement pathway during CPB. The reduction of plasma Bb concentration below the baseline in the Mab 166-32 treated animals could be due to the inhibition of the physiological activation of the alternative complement in the animals.

Activation of the classical complement pathway was determined by measuring C4d, which is a specific marker for the activation of C4 in the classical complement pathway. In the study, the plasma levels of C4d in both the Mab 166-32 treated and control animals were relatively stable with reference to the baseline (FIG. 42). However, there was an increase of C4d in both animal groups after neutralization of heparin with protamine at the end of the CPB, indicating the activation of the classical pathway as reported earlier in other studies (Kirklin J K et al., Ann. Thorac. Surg. 1986; 41: 193-199; Carr J A et al., J. Cardiovasc. Surg. (Torino) 1999; 40: 659-666).

Activation of complement is shown by an increase in plasma C3a in the control animals (FIG. 43). In contrast, animals treated with Mab 166-32 show almost complete inhibition of C3a production. A slight increase of C3a level is observed in the Mab 166-32 treated animals after neutralization of heparin with protamine. Together, the results from FIGS. 41, 42 and 43 support the notion that complement activation during CPB is predominantly via the alternative complement pathway. Due to the lack of cross-reactivity of the reagents in the commercial ELISA kits for baboon C5a and sC5b-9 (Quidel and Becton Dickinson, respectively), their concentrations were not determined.

Activation of neutrophils and monocytes in the baboons was examined by measuring CD11b (α-integrin) expression using immunofluorcytometric methods. In the control animals, the CD11b expression on neutrophils increased rapidly and reached the maximum at about 85 minutes after the start of CPB (209±42.9% of the baseline) (FIG. 44). It then declined slowly back to around the baseline. In contrast, the increase of CD11b expression on neutrophils in the Mab 166-32 treated animals was delayed and smaller in magnitude (FIG. 44). The maximum level of CD11b expression was 129.3%±5.5% of the baseline. Inhibition of the increase in CD11b expression on monocytes from the Mab 166-32 treated animals was also observed (FIG. 45).

Activation of platelets in the baboons was examined by measuring CD62P (P-selectin) expression using immunofluorocytometric methods. Both the control and Mab 166-32 treated animals show a similar pattern of inhibition of CD62P expression (FIG. 46). The exact cause of the inhibition of CD62P expression is unclear.

The effect of Mab 166-32 treatment on pro-inflammatory cytokines was also examined. Baboons treated with Mab 166-32 had a significantly smaller increase in plasma IL-6 concentration as compared to the control animals (FIG. 47).

The effects of Mab 166-32 treatment on tissue injury of various organs were also studied. The increase of plasma LDH levels was significantly reduced in the Mab 166-32 treated animals at 3 and 6 hours after CPB (FIG. 48). This indicates protection against tissue injury. Specifically for myocardial injury, the increase of both plasma CK and CK-MB levels at 6 and 18 hours after CPB was significantly lower in the Mab 166-32 treated animals as compared to the control animals (FIGS. 49 and 50).

As for pulmonary functions, the dynamic lung compliance of the Mab 166-32 treated animals was higher than that of the control animals during the early phase of the open-chest surgery (FIG. 51). However, there was no significant difference in the lung compliance between the two groups of animals during and after CPB. The initial increase of the dynamic lung compliance in the control animals is probably attributed to the open-chest procedure. The higher dynamic lung compliance in the Mab 166-32 treated animals could be due to the protection against surgical trauma which was shown to be associated with complement activation via the alternative complement pathway. (Gu Y J et al., Chest 1999; 116: 892-898).

The renal function of the baboons was also examined. A reduction in the increase of plasma creatinine was found in the baboons treated with Mab 166-32 as compared to the control animals at 18 hours after CPB (FIG. 52).

In conclusion, anti-factor D Mab 166-32 is effective in inhibiting the activation of the alternative complement pathway in a baboon model of CPB. Inhibition of the alternative complement pathway by Mab 166-32 effectively reduces the activation of neutrophils and monocytes, as well as the production of IL6. Treatment with Mab 166-32 confers protection against myocardial and renal injury. The alternative complement pathway may play a predominant role in the inflammation and tissue injury caused by extracorporeal circulation, surgical trauma and ischemiaireperfusion. Therefore Mab 166-32 could be potentially useful for the treatment of systemic inflammatory response syndromes in CPB.

The foregoing description, terms, expressions and examples are exemplary only and not limiting. The invention includes all equivalents of the foregoing embodiments, both known and unknown. The invention is limited only by the claims which follow and not by any statement in any other portion of this document or in any other source.

The invention claimed is:

1. An isolated nucleic acid consisting of the polynucleotide insert of the hybridoma cell line deposited under ATCC Accession Number HB-12476, wherein the polynucleotide insert encodes monoclonal antibody 166-32.

2. An isolated nucleic acid consisting of a subsequence of the polynucleotide insert of the hybridoma cell line deposited under ATCC Accession Number HB-12476, wherein the subsequence encodes a Fab, F(ab')$_2$, Fv or single chain Fv fragment of monoclonal antibody 166-32.

3. An isolated nucleic acid encoding an antibody or an antibody fragment thereof that specifically binds to Factor D, wherein the antibody comprises the variable regions of monoclonal antibody 166-32 produced by the hybridoma cell line deposited under ATCC Accession Number HB-12476 and human constant regions.

4. The nucleic acid of claim 3, wherein the antibody fragment is a Fab, F(ab')$_2$, Fv or single chain Fv fragment.

5. A vector comprising the nucleic acid of any one of claims 1-4.

6. An isolated host cell comprising the vector of claim 5.

7. The host cell of claim 6, which is a NS0 or CHO cell.

8. A method of making an antibody or an antibody fragment thereof that specifically binds to Factor D, comprising culturing the host cell of claim 6 in a medium and obtaining the antibody or antibody fragment expressed therein.

* * * * *